United States Patent
Woods et al.

(10) Patent No.: US 9,796,676 B2
(45) Date of Patent: *Oct. 24, 2017

(54) HONEYBEE REPELLENTS AND USES THEREOF

(71) Applicant: Inscent, Inc., Irvine, CA (US)

(72) Inventors: Daniel F. Woods, Irvine, CA (US); Spiros Dimitratos, Ontario, CA (US); Robin W. Justice, Laguna Niguel, CA (US)

(73) Assignee: Inscent, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/156,313

(22) Filed: May 16, 2016

(65) Prior Publication Data

US 2016/0251312 A1    Sep. 1, 2016

Related U.S. Application Data

(63) Continuation of application No. 14/269,112, filed on May 3, 2014, now Pat. No. 9,357,781.

(60) Provisional application No. 61/819,428, filed on May 3, 2013.

(51) Int. Cl.
| | |
|---|---|
| *A01N 35/10* | (2006.01) |
| *A01N 43/10* | (2006.01) |
| *A01N 43/40* | (2006.01) |
| *A01N 43/56* | (2006.01) |
| *A01N 43/64* | (2006.01) |
| *A01N 43/84* | (2006.01) |
| *C07D 213/74* | (2006.01) |
| *A01N 43/90* | (2006.01) |
| *A01N 43/66* | (2006.01) |
| *A01N 43/78* | (2006.01) |
| *A01N 43/38* | (2006.01) |
| *A01N 43/653* | (2006.01) |
| *C07D 251/10* | (2006.01) |
| *C07D 403/04* | (2006.01) |
| *C07D 417/10* | (2006.01) |
| *A01N 35/04* | (2006.01) |
| *A01N 43/12* | (2006.01) |
| *A01N 43/32* | (2006.01) |
| *A01N 47/44* | (2006.01) |

(52) U.S. Cl.
CPC ........... *C07D 213/74* (2013.01); *A01N 35/04* (2013.01); *A01N 35/10* (2013.01); *A01N 43/10* (2013.01); *A01N 43/12* (2013.01); *A01N 43/32* (2013.01); *A01N 43/38* (2013.01); *A01N 43/40* (2013.01); *A01N 43/56* (2013.01); *A01N 43/64* (2013.01); *A01N 43/653* (2013.01); *A01N 43/66* (2013.01); *A01N 43/78* (2013.01); *A01N 43/84* (2013.01); *A01N 43/90* (2013.01); *A01N 47/44* (2013.01); *C07D 251/10* (2013.01); *C07D 403/04* (2013.01); *C07D 417/10* (2013.01)

(58) Field of Classification Search
CPC ........ A01N 35/10; A01N 43/10; A01N 43/40; A01N 43/56; A01N 43/64; A01N 43/84; A01N 43/86; A01N 51/00
See application file for complete search history.

(56) References Cited

U.S. PATENT DOCUMENTS

| | | | |
|---|---|---|---|
| 4,443,454 A | 4/1984 | Worthington | |
| 2003/0119844 A1 | 6/2003 | Huang et al. | |
| 2007/0015768 A1* | 1/2007 | Alroy .................... | A61K 31/13 514/255.03 |

FOREIGN PATENT DOCUMENTS

| | | |
|---|---|---|
| DE | 4012224 A1 | 10/1991 |
| WO | 2006026619 A2 | 3/2006 |
| WO | 2012151556 A2 | 11/2012 |

OTHER PUBLICATIONS

Alena Fedarovich, Kevin A. Djordjevic, Shauna M. Swanson, Yuri K. Peterson, Robert A. Nicholas and Christopher Davies, "High-Throughput Screening for Novel Inhibitors of Neisseria gonorrhoeae Penicillin-Binding Protein 2", PLoS One, 2012, 7(9), e44918, 1-9.*

F. H. Pollard, G. Nickless and R. G. Anderson, "Some New Heterocyclic Compounds as Analytical Reagents", Talanta, 1966, vol. 13, pp. 725-730.*

Murat Gündüz, Sevim Bilgiç, Orhan Bilgiç, and Devrim Özöğüt, "Novel electrophilic aromatic iodine substitution of some naphtholic Schiff bases", ARKIVOC 2008 (xiii) 115-121.*

Atkins, et al., "Repellent Additives to Reduce Pesticide Hazards to Honey Bees," American Bee Journal, Jul. 1977, vol. 117, No. 7, pp. 438-439, 457.

Atkins, et al., "Repellent Additives to Reduce Pesticide Hazards to Honey Bees: Field Tests," Environmental Entomology, 1975, vol. 4, No. 2, pp. 207-210.

Detzel, et al., "Attraction, Deterrence or Intoxication of Bees (*Apis mellifera*) by Plant Allelochemicals," Chemoecology, 1993, vol. 4, pp. 8-18.

Gupta, et al., "Efficacy of Ketones on the Foraging Behaviour of *Apis florea* F. in Field Conditions," Apidologie, 1987, vol. 18, No. 2, pp. 121-128.

(Continued)

*Primary Examiner* — John Pak
*Assistant Examiner* — Nathan W Schlientz
(74) *Attorney, Agent, or Firm* — UltimatEdge IP Law Group, P.C.; Dean G. Stathakis

(57) ABSTRACT

The present specification discloses honeybee repellents exhibiting repellent properties similar to 2-heptanone, compositions comprising such repellents, uses to repel a honeybee from a mammal, location, plant, structure treated of such repellents, and methods of treating a mammal, location, plant, structure by applying such repellents.

19 Claims, No Drawings

(56) References Cited

OTHER PUBLICATIONS

International Search Report and Written Option PCT/US2014/036713, dated Sep. 23, 2014.
Baker, et al "Evaluation of the Iron Chelation Potential of Hydrazones of Pyridoxal, Salicylaldehyde and 2-Hydroxy-1Naphthylaldehyde using the Hepatocyte in Culture," Hepatology, 1992, vol. 15, No. 3, pp. 492-501.
Clausen, et al., "Studies on organophpsphorus compounds. XXX. Synthesis of ethyl 2-(thioacylamino)-5-ethyl-3-thiophenecarboxylates and 2-substituted 6-ethylthieno[2,3-d][1,3]thiazine-4-thiones," Nouveau Journal de Chimie, 1980, 4(1) 43-46 (Abstract only).
International Search Report and Written Option PCT/US2014/036714, dated Sep. 23, 2014.
Link, et al., "Effects of combined chelation treatment with pyridoxal isonicotinoyl hydrazone analogs and deferoxamine in hypertransfused rats and in iron-loaded rat heart cells," Blood, 2003 101 (10), pp. 4172-4179.
Salman, et al., "Infa-Red Study Tautomerism in Some Schiff Bases," Spectroscopy Letters: An International Journal for Rapid Communication, 1997, 30(7), pp. 1289-1300, (Abstract only).
Taracad, et al., "Structural investigation on phenyl and pyridin-2-ylamino(methylene)naphthalen-2(3H)-one. Substituent effects on the NMR chemical shifts," Magnetic Resonance in Chemistry, 2010, 48(8), pp. 585-592, (Abstract only).

\* cited by examiner

SEQUENCE LISTING

<160> NUMBER OF SEQ ID NOS: 2

<210> SEQ ID NO 1
<211> LENGTH: 142
<212> TYPE: PRT
<213> ORGANISM: Apis mellifera

<400> SEQUENCE: 1

```
Met Asn Thr Leu Val Thr Val Thr Cys Leu Leu Ala Ala Leu Thr Val
1               5                   10                  15

Val Arg Gly Ile Asp Gln Asp Thr Val Val Ala Lys Tyr Met Glu Tyr
            20                  25                  30

Leu Met Pro Asp Ile Met Pro Cys Ala Asp Glu Leu His Ile Ser Glu
            35                  40                  45

Asp Ile Ala Thr Asn Ile Gln Ala Ala Lys Asn Gly Ala Asp Met Ser
        50                  55                  60

Gln Leu Gly Cys Leu Lys Ala Cys Val Met Lys Arg Ile Glu Met Leu
65                  70                  75                  80

Lys Gly Thr Glu Leu Tyr Val Glu Pro Val Tyr Lys Met Ile Glu Val
                85                  90                  95

Val His Ala Gly Asn Ala Asp Asp Ile Gln Leu Val Lys Gly Ile Ala
                100                 105                 110

Asn Glu Cys Ile Glu Asn Ala Lys Gly Glu Thr Asp Glu Cys Asn Ile
            115                 120                 125

Gly Asn Lys Tyr Thr Asp Cys Tyr Ile Glu Lys Leu Phe Ser
        130                 135                 140
```

<210> SEQ ID NO 2
<211> LENGTH: 142
<212> TYPE: PRT
<213> ORGANISM: Apis cerana

<400> SEQUENCE: 2

```
Met Asn Thr Leu Val Thr Val Thr Cys Leu Leu Ala Ala Leu Thr Val
1               5                   10                  15

Val Arg Gly Ile Asp Gln Asp Thr Val Val Ala Lys Tyr Met Glu Tyr
            20                  25                  30

Leu Met Pro Asp Ile Met Pro Cys Ala Asp Glu Leu His Ile Ser Glu
            35                  40                  45

Asp Ile Ala Thr Asn Ile Gln Ala Ala Lys Asn Gly Ala Asp Met Ser
        50                  55                  60

Gln Leu Gly Cys Leu Lys Ala Cys Val Met Lys Arg Ile Glu Met Leu
65                  70                  75                  80

Lys Gly Thr Glu Leu Tyr Val Glu Pro Val Tyr Lys Lys Ile Glu Val
                85                  90                  95

Val His Ala Gly Asn Ala Asp Asp Ile Gln Leu Val Lys Gly Ile Ala
                100                 105                 110

Asn Glu Cys Ile Glu Asn Ala Glu Gly Glu Thr Asp Glu Cys Asn Ile
            115                 120                 125

Gly Asn Lys Tyr Thr Asp Cys Tyr Ile Glu Lys Leu Phe Ser
        130                 135                 140
```

HONEYBEE REPELLENTS AND USES THEREOF

This patent application claims priority pursuant to 35 U.S.C. §120 35 U.S.C. to U.S. Non-Provisional patent application Ser. No. 14/269,112, filed May 3, 2014, a patent application that claims priority pursuant to 35 U.S.C. §119 (e) to U.S. Provisional Patent Application 61/819,428, filed May 3, 2013, each of which is hereby incorporated by reference in its entirety.

Portions of the work described herein were supported by Small Business Innovation Research (SBIR) grant numbers 0611005, 0810785, and 0956877 awarded by the National Science Foundation (NSF). The government of the United States of America may retain certain rights to this patent.

Honeybees use scent marks while foraging. When collecting nectar and/or pollen, foraging honeybees scent mark nectar-producing flower by depositing attractive pheromones to signal to other honeybees of a nearby rewarding food source. Honeybees also use a short-lived repellent scent mark that identifies exhausted and recently visited rewarding flowers not yet replenished with nectar. Subsequently visiting honeybees detect and avoid these nectar-depleted flowers. Over time, as nectar replenishes in the flower, the repellent scent mark fades until gone and the flower is eventually revisited by another foraging honeybee. It is presumed that the use of repellent scent marks increases foraging efficiency by reducing the time spent probing nectar-depleted flowers.

The repellent scent mark used by honeybees is 2-heptanone. Produced and secreted by the mandibular glands of adult worker honey bees, 2-heptanone is known as the alarm pheromone because under certain circumstances elicits aggressive behavior in honeybees when detected. Honeybees detect 2-heptanone using an olfactory pathway mediated by a specific odorant-binding protein called OBP2. By taking advantage of its properties, repellent formulation of 2-heptanone have been produced and used in agricultural settings. For example, 2-heptanone has been applied to crops in order to repel honeybees away from areas where toxic insecticides have also been applied, thereby reducing honeybee mortality and avoiding potential insecticide contamination of the colony and the hive products obtained thereof. However, such uses have had very limited success primarily because 2-heptanone is a considerably volatile compound, having an effective half-life of only a few hours. As such, 2-heptanone is impractical and cost-ineffective for agricultural uses because of the extensive efforts necessary to apply and maintain an effective amount of this repellent in the treated area.

Therefore, what are needed are more effective honeybee repellents that exhibit repellent properties similar to 2-heptanone, but are less volatile. The present specification discloses such honeybee repellents and uses and methods for such compounds. The disclosed honeybee repellents will benefit apiculture since honeybees are a crucial, domesticated species that is threatened by routine agricultural practices such as the use of insecticides.

Thus, aspects of the present specification disclose honeybee repellents exhibiting repellent properties similar to 2-heptanone, but are less volatile than 2-heptanone.

Other aspects of the present specification disclose a use of a honeybee repellent disclosed herein to repel a honeybee from a location treated with the honeybee repellent. In one embodiment, the disclosed use is a use of a honeybee repellent disclosed herein to repel a honeybee from foraging and/or collecting nectar from a flower of a plant treated with the honeybee repellent. In another embodiment, the disclosed use is a use of a honeybee repellent disclosed herein to repel a honeybee from a structure treated with the honeybee repellent.

Yet other aspects of the present specification disclose a method of treating a location by applying a honeybee repellent disclosed herein, wherein the application repels a honeybee from the treated location. In one embodiment, the disclosed method is a method of treating a plant by applying a honeybee repellent disclosed herein, wherein such application repels a honeybee from foraging and/or collecting nectar from a flower of the treated plant. In another embodiment, the disclosed method is a method of treating a structure by applying a honeybee repellent disclosed herein, wherein such application repels a honeybee from the treated structure.

DESCRIPTION

Honeybees are maintained by humans in order to harvest honey, beeswax, and other hive products produced by these insects for commercial markets. In the United States, for example, honeybees produce $270 million worth of honey, beeswax, and other hive products. Besides the economic importance of hive products, honeybees are critically necessary to pollinate many important agricultural crops produced worldwide. For example, honeybees pollinate over $14 billion worth of crops annually in the United States. As such, promoting and maintaining honeybee survival is of great economic importance.

Insecticides are widely used to increase the yields of agricultural crops and their use is one of the major factors behind the increase in agricultural productivity in the 20th century. However, there is an inherent tension between the use of insecticides on crop plants to control invading pest insects and the necessity of honeybees to pollinate these same plants and the economic importance of hive products. One commonly used method is to delay the use of insecticides until the honeybees pollination has occurred, and then apply the insecticide. However, foraging for nectar occurs throughout the growing season, and as such, foraging honeybees are still exposed to the insecticide. Furthermore, recent evidence suggests that commonly used nicotine-based insecticides like Clothianidin and Imidacloprid may be a causal factor in colony collapse disorder, a phenomenon in which worker honeybees from a colony abruptly disappear. As such, it would be extremely beneficial to develop and use compounds and methods of insect control that minimize honeybee mortality.

Although of significant value, honeybee pollination can also cause economic harm to certain agricultural crops. For example, certain seedless citrus fruits like seedless tangerines, grapefruit, and mandarin oranges are of great economic value due to consumer preference. These seedless fruits are self-pollinating. However, if honeybees cross-pollinate the crop plants with the pollen of a seeded citrus fruit, then these citrus fruits will develop seeds and become undesirable to the consumer. As such, citrus fruit growers employ insecticides in order to prevent honeybee cross-pollination. The most common insecticides used for this application are neonicotinoids like Clothianidin and Imidacloprid, which as discussed above, appears to be a causal factor in colony collapse disorder. One problem with this approach is that the nectar collected by honeybees from the flowers of citrus trees produces a flavorful and economically desirable honey. As such, beekeepers have historically kept colonies near citrus orchards. Thus, there is another inherent tension between the economic importances of hive products produced by honeybees versus the financial harm caused by honeybee pollination in certain agricultural crops like citrus trees. As such, it would be extremely beneficial to develop and use compounds and methods that could repel honeybees from crop plants where pollination is undesired without causing significant honeybee mortality.

Insect chemosensory proteins (CSPs) regulate or control crucial behaviors. The chemosensory system consists of several chemosensory protein (CSP) classes. Chemosensory protein classes that are important in the design of novel insect control products include soluble proteins found in the antennal hemolymph and the maxillary palps, such as odorant binding proteins (OBPs) and sensory appendage proteins (SAPs). OBPs and SAPs are carrier proteins that facilitate the transport of external stimuli such as odor molecules through the aqueous hemolymph of sensory appendages to the surfaces of neuronal cells. There, the protein/odorant molecule complexes bind G-protein coupled receptors (GPCRs) and initiate a signaling cascade that results in a behavioral response to the external odor or stimulus. Insects use chemosensory cues from the environment to control critical behaviors, such as feeding and mating. Thus, insect chemosensory proteins are promising targets for the discovery of novel insect control products based on manipulating insect behavior.

The present specification discloses improved honeybee repellents and uses and methods for such repellents. By exploiting the OBP2 olfactory pathway used by 2-heptanone, more effective repellent compounds have been identified and isolated. As such, the repellents disclosed herein manipulate the honeybees' chemosensory system by eliciting an avoidance response similar to the one initiated by 2-heptanone. The repellents disclosed herein are intended for agricultural, commercial, and consumer use. For example, the honeybee repellents disclosed herein are useful to repel honeybees from areas where insecticides have also been applied in order to reduce honeybee mortality and avoid insecticide contamination of honey, beeswax, and other hive products. As another non-limiting example, the honeybee repellents disclosed herein are useful to prevent unwanted pollination of plants by honeybees in crops where such pollination reduces the market value due to the resulting seeded fruits. As yet another non-limiting example, the honeybee repellents disclosed herein are useful to keep away honeybees from outdoor areas where human activities are occurring and would be disrupted by honeybee presence, such as, e.g., an outdoor activity like a sporting event or picnic. Similarly, the honeybee repellents disclosed herein are useful to keep away honeybees from man-made structures in order to prevent infestation of a colony, such as, e.g., a commercial building, a house, a shed, or other structure. Other uses of the honeybee repellents disclosed herein are discussed below and are readily apparent to a person of ordinary skill.

Aspects of the present specification disclose a honeybee repellent. As used herein, the term "honeybee repellent" is synonymous with "repellent compound" and refers to a compound that mimics a 2heptanone-specific response. 2-Heptanone, $CH_3(CH_2)_4COCH_3$, CAS Registry No. 110-43-0, also known as methyl n-amyl ketone and methyl pentyl ketone, is a colorless, liquid with a banana-like, fruity odor. It is a volatile liquid at room temperature [d415 0.8197; b.p.$_{760}$ 151.5° C.] and soluble in alcohol or ether and very slightly soluble in water. 2-Heptanone is available commercially.

Bees are insects of the Order Hymenoptera, Superfamily Apoidea, and comprise a group of about 20,000 species that live throughout the world. Examples of common bees are honeybees (*Apis*), bumble bees (*Bomzbus*), small carpenter bees (*Ceratina*), large carpenter bees (*Xylocopa*), paper wasps (*Polistes*), yellow jackets (*Vespula*), and baldfaced hornets (*Vespula*). At least seven species of honeybee are commonly recognized with a total of 44 subspecies and various strains, varieties, and hybrids thereof. As used herein, the term "honeybee" refers to any member of the Order Hymeoptera, Family Apidae, and includes, without limitation, *Apis andreniformis, Apis cerana, Apis dorsata, Apis florae, Apis koschevnikovi, Apis laboriosa, Apis mellifera, Apis nigrocincta, Apis rorea*, subspecies thereof, and strains, varieties, and hybrids thereof.

In one embodiment, a honeybee repellent disclosed herein substantially mimics the attractant chemosensory cues of a natural compound produced by a plant or plant part like a flower. In an aspect of this embodiment, a honeybee repellent disclosed herein substantially mimics a repellent chemosensory cue of 2-heptanone.

In aspects of this embodiment, a honeybee repellent disclosed herein has a repellent chemosensory cue that is, e.g., about 75%, about 80%, about 85%, about 90%, about 95%, about 97%, or about 100% that of the repellent chemosensory cue of 2-heptanone. In other aspects of this embodiment, a honeybee repellent disclosed herein has a repellent chemosensory cue that is, e.g., at least 75%, at least 80%, at least 85%, at least 90%, at least 95%, or at least 97% that of the repellent chemosensory cue of 2-heptanone. In other aspects of this embodiment, a honeybee repellent disclosed herein has a repellent chemosensory cue that is between, e.g., about 75% to about 97%, about 80% to about 97%, about 85% to about 97%, about 90% to about 97%, about 75% to about 100%, about 80% to about 100%, about 85% to about 100%, or about 90% to about 100% that of the repellent chemosensory of 2-heptanone.

In an embodiment, a honeybee repellent disclosed herein has a repellent chemosensory cue that is, e.g., at least one-fold, at least two-fold, at least three-fold, at least four fold, at least five-fold, at least six-fold, at least seven-fold, at least eight-fold, at least nine-fold, at least 10-fold, at least 20-fold, at least 30-fold, at least 40-fold, at least 50-fold, at least 60-fold, at least 70-fold, at least 80-fold, at least 90-fold, at least 100-fold, at least 125-fold, at least 150-fold, at least 175-fold, or at least 200-fold that of the repellent chemosensory cue of 2-heptanone.

In an embodiment, a honeybee repellent disclosed herein has a honeybee repellency activity. In aspects of this embodiment, presence of a honeybee repellent repels honeybees by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%, as compared to not having the honeybee repellent present. In other aspects of this embodiment, presence of a honeybee repellent repels honeybees by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%, as compared to not having the honeybee repellent present.

In an embodiment, a honeybee repellent disclosed herein reduces a honeybee interaction with a mammal, a plant, structure, and/or location. In aspects of this embodiment, a honeybee repellent reduces honeybee interaction with a mammal, plant, structure, and/or location by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In other aspects of this embodiment, a honeybee repellent reduces honeybee interaction with a mammal, a plant, structure, and/or location by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a honeybee repellent disclosed herein reduces an ability of a honeybee to obtain a meal and/or nectar from a plant. In aspects of this embodiment, a honeybee repellent reduces an ability of a honeybee to obtain a meal from a plant by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In other aspects of this embodiment, a honeybee repellent reduces an ability of a honeybee to obtain a meal and/or nectar from a plant by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A honeybee repellant disclosed herein may be more stable (or less volatile) than 2-heptanone. In aspects of this embodiment, a honeybee repellant disclosed herein has a half-life of, e.g., about one day, about three days, about five days, about one week, about two weeks, about three weeks, about one month, about two months, or about three months. In other aspects of this embodiment, a honeybee repellant disclosed herein has a half-life of, e.g., at least one day, at least three days, at least five days, at least one week, at least two weeks, at least three weeks, at least one month, at least two months, or at least three months. In yet other aspects of this embodiment, a honeybee repellant disclosed herein has a half-life of between, e.g., about one day to about seven days, about three days to about seven days, about five days to about seven days, about one week to about four weeks, about two weeks to about four weeks, about three weeks to about four weeks, about one month to about four months, about two months to about four months, or about three months to about four months.

A honeybee repellent may preferentially bind, without limitation, an odorant Binding Protein 2 (OBP2). OBP2, also known as ASP2, refers to a soluble, acidic protein of about 13-16 kDa that is expressed in sensory tissues of honeybees. This protein binds 2-heptanone and escorts this compound across the hydrophilic extracellular matrix to the cell surface, where odorant receptors are located. Exemplary honeybee OBP2s include, without limitation, *Apis mellifera* OBP2 (SEQ ID NO: 1) and *Apis cerana* OBP2 (SEQ ID NO: 2). For a general review see, e.g., Dani, et al., Mapping the Expression of Soluble Olfactory Proteins in the Honeybee, J. Proteome Res. 9(4): 1822-1833 (2010); Pelosi, et al., Soluble Proteins in Insect Chemical Communication, Cell. Mol. Life Sci. 63(14): 1658-1676 (2006); Calvello, et al., Expression of Odorant-Binding Proteins and Chemosensory Proteins in Some Hymenoptera, Insect Biochem. Mol. Biol. 35(4): 297-307 (2005), each of which is hereby incorporated by reference in its entirety.

A honeybee repellent disclosed herein may be characterized by it binding affinity. Binding affinity can be described by an equilibrium dissociation constant (KD), which is defined as the ratio Kd/Ka at equilibrium; where Ka is the association rate constant of the repellent compound and kd is the dissociation rate constant of the repellent compound. Binding affinity is determined by both the association and the dissociation and alone neither high association or low dissociation can ensure high affinity. The association rate constant (Ka), or on-rate constant (Kon), measures the number of binding events per unit time, or the propensity of the repellent compound and the honeybee OBP to associate reversibly into its repellent-OBP complex. The association rate constant is expressed in $M^{-1} s^{-1}$. The larger the association rate constant, the more rapidly the repellent compound binds to its honeybee OBP, or the higher the binding affinity between repellent compound and honeybee OBP. The dissociation rate constant (Kd), or off-rate constant (Koff), measures the number of dissociation events per unit time propensity of a repellent-OBP complex to separate (dissociate) reversibly into its component molecules, namely the repellent compound and the honeybee OBP. The dissociation rate constant is expressed in $s^{-1}$. The smaller the dissociation rate constant, the more tightly bound the repellent compound is to its honeybee OBP, or the higher the binding affinity between repellent compound and honeybee OBP. The equilibrium dissociation constant (KD) measures the rate at which new repellent-OBP complexes formed equals the rate at which repellent-OBP complexes dissociate at equilibrium. The equilibrium dissociation constant is expressed in M, and is defined as Koff/Kon=[L]×[R]/[L+R], where [L] is the molar concentration of the repellent compound, [R] is the molar concentration of the honeybee OBP, and [L+R] is the molar concentration of the repellent-OBP complex, where all concentrations are of such components when the system is at equilibrium. The smaller the equilibrium dissociation constant, the more tightly bound the repellent compound is to its honeybee OBP, or the higher the binding affinity between repellent compound and honeybee OBP.

In an embodiment, a honeybee repellent disclosed herein has a binding affinity that is substantially the same as the binding affinity of the natural ligand for that honeybee OBP. In aspects of this embodiment, a honeybee repellent disclosed herein has a binding affinity for a honeybee OBP that is, e.g., about 75%, about 80%, about 85%, about 90%, about 95%, about 97%, or about 100% that of the binding affinity of the natural ligand for that honeybee OBP. In other aspects of this embodiment, a honeybee repellent disclosed herein has a binding affinity for a honeybee OBP that is, e.g., at least 75%, at least 80%, at least 85%, at least 90%, at least 95%, or at least 97% that of the binding affinity of the natural ligand for that honeybee OBP. In other aspects of this embodiment, a honeybee repellent disclosed herein has a binding affinity for a honeybee OBP that is between, e.g., about 75% to about 97%, about 80% to about 97%, about 85% to about 97%, about 90% to about 97%, about 75% to about 100%, about 80% to about 100%, about 85% to about 100%, or about 90% to about 100% that of the binding affinity of the natural ligand for that honeybee OBP.

In an embodiment, the binding affinity of a honeybee repellent that binds to a honeybee OBP has a dissociation equilibrium constant that is greater than the dissociation equilibrium constant of the natural ligand for that honeybee OBP. In aspects of this embodiment, the binding affinity of a honeybee repellent that binds to a honeybee OBP has a dissociation equilibrium constant that is greater than the dissociation equilibrium constant of the natural ligand for that honeybee OBP by, e.g., at least one-fold, at least two-fold, at least three-fold, at least four fold, at least five-fold, at least six-fold, at least seven-fold, at least eight-fold, at least nine-fold, at least 10-fold, at least 20-fold, at least 30-fold, at least 40-fold, at least 50-fold, at least 60-fold, at least 70-fold, at least 80-fold, at least 90-fold, at least 100-fold, at least 125-fold, at least 150-fold, at least 175-fold, or at least 200-fold.

In another embodiment, a honeybee repellent disclosed herein binds to a honeybee OBP with binding affinity having an association rate constant of, e.g., less than $1 \times 10^5$ $M^{-1}$ $s^{-1}$, less than $1 \times 10^6$ $M^{-1}$ $s^{-1}$, less than $1 \times 10^7$ $M^{-1}$ $s^{-1}$, or less than $1 \times 10^8$ $M^{-1}$ $s^{-1}$. In another embodiment, a honeybee repellent disclosed herein binds to a honeybee OBP with binding affinity having an association rate constant of, e.g., more than $1 \times 10^5$ $M^{-1}$ $s^{-1}$, more than $1 \times 10^6$ $M^{-1}$ $s^{-1}$, more than $1 \times 10^7$ $M^{-1}$ $s^{-1}$, or more than $1 \times 10^8$ $M^{-1}$ $s^{-1}$. In another embodiment, a honeybee repellent disclosed herein binds to a honeybee OBP with binding affinity having an association rate constant between $1 \times 10^5$ $M^{-1}$ $s^{-1}$ to $1 \times 10^8$ $M^{-1}$ $s^{-1}$, $1 \times 10^6$ $M^{-1}$ $s^{-1}$ to $1 \times 10^8$ $M^{-1}$ $s^{-1}$, $1 \times 10^5$ $M^{-1}$ $s^{-1}$ to $1 \times 10^7$ $M^{-1}$ $s^{-1}$, or $1 \times 10^6$ $M^{-1}$ $s^{-1}$ to $1 \times 10^7$ $M^{-1}$ $s^{-1}$.

In another embodiment, a honeybee repellent disclosed herein binds to a honeybee OBP with binding affinity having a disassociation rate constant of less than $1 \times 10^{-3}$ $s^{-1}$, less than $1 \times 10^{-4}$ $s^{-1}$, or less than $1 \times 10^{-5}$ $s^{-1}$. In another embodiment, a honeybee repellent disclosed herein binds to a honeybee OBP with binding affinity having a disassociation rate constant of, e.g., less than $1.0 \times 10^{-4}$ $s^{-1}$, less than $2.0 \times 10^{-4}$ $s^{-1}$, less than $3.0 \times 10^{-4}$ $s^{-1}$, less than $4.0 \times 10^{-4}$ $s^{-1}$, less than $5.0 \times 10^{-4}$ $s^{-1}$, less than $6.0 \times 10^{-4}$ $s^{-1}$, less than $7.0 \times 10^{-4}$ $s^{-1}$, less than $8.0 \times 10^{-4}$ $s^{-1}$, or less than $9.0 \times 10^{-4}$ $s^{-1}$. In another embodiment, a honeybee repellent disclosed herein binds to a honeybee OBP with binding affinity having a disassociation rate constant of, e.g., more than $1 \times 10^{-3}$ $s^{-1}$, more than $1 \times 10^{-4}$ $s^{-1}$, or more than $1 \times 10^{-5}$ $s^{-1}$. In another embodiment, a honeybee repellent disclosed herein binds to a honeybee OBP with binding affinity having a disassociation rate constant of, e.g., more than $1.0 \times 10^{-4}$ $s^{-1}$, more than $2.0 \times 10^{-4}$ $s^{-1}$, more than $3.0 \times 10^{-4}$ $s^{-1}$, more than $4.0 \times 10^{-4}$ $s^{-1}$, more than $5.0 \times 10^{-4}$ $s^{-1}$, more than $6.0 \times 10^{-4}$ $s^{-1}$, more than $7.0 \times 10^{-4}$ $s^{-1}$, more than $8.0 \times 10^{-4}$ $s^{-1}$, or more than $9.0 \times 10^{-4}$ $s^{-1}$.

In another embodiment, a honeybee repellent disclosed herein binds to a honeybee OBP with binding affinity having an equilibrium disassociation constant of less than 0.500 nM. In aspects of this embodiment, a honeybee repellent disclosed herein binds to a honeybee OBP with binding affinity having an equilibrium disassociation constant of, e.g., less than 0.500 nM, less than 0.450 nM, less than 0.400 nM, less than 0.350 nM, less than 0.300 nM, less than 0.250 nM, less than 0.200 nM, less than 0.150 nM, less than 0.100 nM, or less than 0.050 nM. In another embodiment, a honeybee repellent disclosed herein binds to a honeybee OBP with binding affinity having an equilibrium disassociation constant of more than 0.500 nM. In aspects of this embodiment, a honeybee repellent disclosed herein binds to a honeybee OBP with binding affinity having an equilibrium disassociation constant of, e.g., more than 0.500 nM, more than 0.450 nM, more than 0.400 nM, more than 0.350 nM, more than 0.300 nM, more than 0.250 nM, more than 0.200 nM, more than 0.150 nM, more than 0.100 nM, or more than 0.050 nM.

In another embodiment, a honeybee repellent disclosed herein has a binding affinity that is substantially the same as the binding affinity of 2-heptanone for that honeybee OBP. In aspects of this embodiment, a honeybee repellent disclosed herein has a binding affinity for a honeybee OBP that is, e.g., about 75%, about 80%, about 85%, about 90%, about 95%, about 97%, or about 100% that of the binding affinity of 2-heptanone for that honeybee OBP. In other aspects of this embodiment, a honeybee repellent disclosed herein has a binding affinity for a honeybee OBP that is, e.g., at least 75%, at least 80%, at least 85%, at least 90%, at least 95%, or at least 97% that of the binding affinity of 2-heptanone for that honeybee OBP. In other aspects of this embodiment, a honeybee repellent disclosed herein has a binding affinity for a honeybee OBP that is between, e.g., about 75% to about 97%, about 80% to about 97%, about 85% to about 97%, about 90% to about 97%, about 75% to about 100%, about 80% to about 100%, about 85% to about 100%, or about 90% to about 100% that of the binding affinity of (R)-(+)-Limonene for that honeybee OBP.

In an embodiment, the binding affinity of a honeybee repellent that binds to a honeybee OBP has a dissociation equilibrium constant that is greater than the dissociation equilibrium constant of 2-heptanone for that honeybee OBP by, e.g., at least one-fold, at least two-fold, at least three-fold, at least four fold, at least five-fold, at least six-fold, at least seven-fold, at least eight-fold, at least nine-fold, at least 10-fold, at least 20-fold, at least 30-fold, at least 40-fold, at least 50-fold, at least 60-fold, at least 70-fold, at least 80-fold, at least 90-fold, at least 100-fold, at least 125-fold, at least 150-fold, at least 175-fold, or at least 200-fold.

For convenience, the term "molecular weight" is used with respect to a moiety or part of a molecule to indicate the sum of the atomic masses of the atoms in the moiety or part of a molecule, even though it may not be a complete molecule.

As used herein, the term "acid anhydride" group refers to a molecule with two acyl groups attached to the same oxygen, and general formula $(RCO)_2O$. As used herein, the term "acetyl" group refers to the functional group —C(=O)CH$_3$. As used herein, the term "acyl" refers to a functional group comprising a carbonyl attached to an alkenyl, alkyl, aryl, cycloalkyl, heteroaryl, heterocycle, or any other moiety were the atom attached to the carbonyl is carbon. Examples of acyl groups include, without limitation, formyl, alkanoyl and aroyl. As used herein, the term "acylamino" refers to a functional group comprising an acyl group attached to the parent moiety through an amino group. Examples of acylamino groups include, without limitation, acetylamino (CH$_3$C(=O)NH—). As used herein, the term "acyl halide"

refers to the functional group haloformyl (COX, with X being a halogen). As used herein, the term "alcohol" refers to a molecule comprising a hydroxyl group (—OH), and having the general formula ROH, wherein R is an organic moiety or group. As used herein, the term "aldehyde" refers to a molecule comprising a carbonyl group [—C(=O)H], and having the general formula RCHO, wherein R is an organic moiety or group.

As used herein, the term "alkene", "olefin", or "olefine" refers to a straight-chain or branched-chain hydrocarbon containing from 2 to 20 carbon atoms and having one or more double bonds and not having any cyclic structure. An alkene with only one double bond has the general formula CnH2n. An alkene with two carbon-carbon double bonds is called a diene, with three carbon-carbon double bonds is called a triene, and with four carbon-carbon double bonds is called a tetraene. An alkene may be optionally substituted as defined herein. Examples of alkenes include, without limitation, ethene, propene, butene, pentene, hexene, heptene, octene, nonene, decene, undecene, dodecene, tridecene, tetradecene, pentadecene, hexadecene, heptadecene, octadecene, nonadecene, eicosene, and the like.

As used herein, the term "alkenyl" refers to a functional group or moiety comprising a straight-chain or branched-chain hydrocarbon containing from 2 to 20 carbon atoms and having one or more carbon-carbon double bonds and not having any cyclic structure including straight-chain or branched-chain hydrocarbon containing 2-6 carbon atoms, 3-6 carbon atoms, 3-7 carbon atoms, 4-7 carbon atoms, 4-8 carbon atoms, and 5-10 carbon atoms. An alkenyl group may be optionally substituted as defined herein. As used herein, "lower alkenyl" refers to alkenyl moieties having from 2 to about 6 carbon atoms. Examples of alkenyl groups include, without limitation, ethenyl, propenyl, 2-methylpropenyl, butenyl, 1,4-butadienyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, and eicosenyl. As used herein, the term "alkylene" refers to a saturated aliphatic functional group or moiety derived from a straight or branched chain saturated hydrocarbon attached at two or more positions, such as methylene (—$C_2$—). An alkylene is a divalent hydrocarbyl radical, i.e., the alkylene moiety is attached to the other parts of the molecule at two distinct positions. Unless otherwise specified, the term "alkyl" may include "alkylene" groups.

As used herein, either alone or in combination, the term "alkoxy" refers to a functional group comprising an alkyl ether group. Examples of alkoxys include, without limitation, methoxy, ethoxy, n-propoxy, isopropoxy, n-butoxy, iso-butoxy, sec-butoxy, tert-butoxy, and the like.

As used herein the term "alkyl" refers to a functional group or moiety comprising a straight-chain or branched-chain hydrocarbon containing from 1 to 35 carbon atoms linked exclusively by single bonds and not having any cyclic structure including straight-chain or branched-chain hydrocarbon containing 1 to 6 carbon atoms, 7 carbon atoms, 2-6 carbon atoms, 3-6 carbon atoms, 4-7 carbon atoms, 5-10 carbon atoms, 5-9 carbon atoms, and 5-8 carbon atoms. As used herein, "lower alkyl" refers to alkyl moieties having from 1 to about 6 carbon atoms. An alkyl group may be optionally substituted as defined herein. Examples of alkyl groups includes, without limitation, methyl, ethyl, n-propyl, isopropyl, n-butyl, isobutyl, sec-butyl, tert-butyl, pentyl, iso-amyl, hexyl, heptyl, octyl, noyl, decyl, undecyl, dodecyl, tridecyl, tetradecyl, pentadecyl, hexadecyl, heptadecyl, octadecyl, nonadecyl, and eicosyl. In some embodiments, alkyl may include $C_{1-10}$ linear alkyl, such as, e.g., methyl (—$CH_3$), ethyl (—$CH_2CH_3$), n-propyl (—$CH_2CH_2CH_3$), n-butyl (—$CH_2CH_2CH_2CH_3$), n-pentyl (—$CH_2CH_2CH_2CH_2CH_3$), n-hexyl (—$CH_2CH_2CH_2CH_2CH_2CH_3$). In some embodiments, alkyl may include $C_{3-10}$ branched alkyl, such as, e.g., $C_3H_7$ (e.g. iso-propyl), $C_4H_9$ (e.g. branched butyl isomers), $C_5H_{11}$ (e.g. branched pentyl isomers), $C_6H_{13}$ (e.g. branched hexyl isomers), and $C_7H_{15}$ (e.g. heptyl isomers).

As used herein, the term "alkylamino" refers to a functional group comprising a saturated straight or branched alkyl substituted by one or more amino groups. Examples of alkylamino groups includes, without limitation methylamino and tert-butylamino. As used herein, the term "aminoalkyl" refers to a functional group comprising an alkyl group attached to the parent molecular moiety through an amino group. An alkylamino group may be a mono- or dialkylated forming group such as, e.g., N-methylamino, N-ethylamino, N,N-dimethylamino, N,N-ethylmethylamino and the like.

As used herein, the term "alkylcarbonyl" or "alkanoyl" refers to a functional group comprising an alkyl group attached to the parent molecular moiety through a carbonyl group. Examples of alkylcarbonyl groups include, without limitation, methylcarbonyl, ethylcarbonyl, and the like. As used herein, the term "alkylidene" refers to a functional group comprising an alkenyl group in which one carbon atom of the carbon-carbon double bond belongs to the moiety to which the alkenyl group is attached. As used herein, the term "alkylthio" refers to a saturated straight or branched alkyl chain substituted by one or more thiol groups. Examples of alkyl groups includes, without limitation methylthio, ethylthio, n-propylthio, isopropylthio, n-butylthio, iso-butylthio, sec-butylthio, and tert-butylthio.

As used herein, the term "alkynyl" refers to a functional group or moiety comprising a straight-chain or branched-chain hydrocarbon containing from 2 to 20 carbon atoms and having one or more carbon-carbon triple bonds and not having any cyclic structure including straight-chain or branched-chain hydrocarbon containing 2-6 carbon atoms, 3-6 carbon atoms, 3-7 carbon atoms, 4-7 carbon atoms, 4-8 carbon atoms, and 5-10 carbon atoms. As used herein, "lower alkenyl" refers to alkenyl moieties having from 2 to about 6 carbon atoms. An alkynyl group may be optionally substituted as defined herein. Examples of alkynyl groups include, without limitation, ethynyl, propynyl, hydroxypropynyl, butynyl, butyn-1-yl, butyn-2-yl, 3-methylbutyn-1-yl, pentynyl, pentyn-1-yl, hexynyl, hexyn-2-yl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, and eicosynyl. As used herein, the term "alkynylene" refers to a carbon-carbon triple bond attached at two positions such as ethynylene (—C:::C—, —C≡C—). Unless otherwise specified, the term "alkynyl" may include "alkynylene" groups.

As used herein, the term "aryl" or "aryl hydrocarbon" refers to a functional group or moiety comprising an aromatic hydrocarbon with a conjugated cyclic molecular ring structure of 3 to 12 carbon atoms including a conjugated cyclic molecular ring structure of 4 carbon atoms, 5 carbon atoms, 6 carbon atoms, 7 carbon atoms, 4-6 carbon atoms, 4-5 carbon atoms, 5-6 carbon atoms, and 4-7 carbon atoms. As used herein, "lower aryl" refers to aryl moieties having from 3 to about 6 carbon atoms including, without limitation, phenyl and naphthyl. An aryl group may be optionally substituted as defined herein. An aryl group can be monocyclic, bicyclic or polycyclic, and may optionally include one to three additional ring structures, such as, e.g., a cycloalkyl, a cycloalkenyl, a heterocycloalkyl, a heterocycloalkenyl, or a heteroaryl. The term "aryl" includes, without limitation, phenyl (benzenyl), thiophenyl, indolyl, naphthyl, totyl, xylyl, anthracenyl, phenanthryl, azulenyl, biphenyl, naphthalenyl, 1-mMethylnaphthalenyl, acenaphthenyl, acenaphthylenyl, anthracenyl, fluorenyl, phenalenyl, phenanthrenyl, benzo[a]anthracenyl, benzo[c]phenanthrenyl, chrysenyl, fluoranthenyl, pyrenyl, tetracenyl (naphthacenyl), triphenylenyl, anthanthrenyl, benzopyrenyl, benzo[a]pyrenyl, benzo[e]fluoranthenyl, benzo[ghi]perylenyl, benzo[j]fluoranthenyl, benzo[k]fluoranthenyl, corannulenyl, coronenyl, dicoronylenyl, helicenyl, heptacenyl, hexacenyl, ovalenyl, pentacenyl, picenyl, perylenyl, and tetraphenylenyl.

As used herein, the term "arylalkenyl" or "aralkenyl" refers to a functional group comprising an aryl group attached to the parent molecular moiety through an alkenyl group. As used herein, the term "arylalkoxy" or "aralkoxy" refers to a functional group comprising an aryl group attached to the parent molecular moiety through an alkoxy group. As used herein, the term "arylalkyl" or "aralkyl," refers to a functional group comprising an aryl group attached to the parent molecular moiety through an alkyl group. As used herein, the term "arylalkynyl" or "aralkynyl" refers to a functional group comprising an aryl group attached to the parent molecular moiety through an alkynyl group. As used herein, the term "arylalkanoyl" or "aralkanoyl" or "aroyl" refers to a functional group comprising an acyl group derived from an aryl-substituted alkanecarboxylic acid such as, e.g., benzoyl, napthoyl, phenylacetyl, 3-phenylpropionyl (hydrocinnamoyl), 4-phenylbutyryl, (2-naphthyl)acetyl, 4-chlorohydrocinnamoyl, and the like. As used herein, the term "aryloxy" refers to a functional group comprising an aryl group attached to the parent molecular moiety through an oxy group.

As used herein, the term "cycloalkyl", "carbocyclicalkyl", and "carbocyclealkyl" refers to a functional group or moiety comprising a non-aromatic hydrocarbon with a non-conjugated cyclic molecular ring structure of 3 to 12 carbon atoms linked exclusively with carbon-carbon single bonds in the carbon ring structure including a non-conjugated cyclic molecular ring structure of 4 carbon atoms, 5 carbon atoms, 6 carbon atoms, 3-8 carbon atoms, 3-7 carbon atoms, 4-7 carbon atoms, 4-6 carbon atoms, 4-5 carbon atoms, and 5-6 carbon atoms. A cycloalkyl group may be optionally substituted as defined herein. As used herein, "lower cycloalkyl" refers to cycloalkyl moieties having from 3 to about 6 carbon atoms. A cycloalkyl group can be monocyclic, bicyclic or polycyclic, and may optionally include one to three additional ring structures, such as, e.g., an aryl, a heteroaryl, a cycloalkenyl, a heterocycloalkyl, or a heterocycloalkenyl. In some embodiments, a cycloalkyl may include $C_{3-10}$ cycloalkyl, such as, e.g., $C_3H_5$ (e.g. cyclopropyl), $C_4H_7$ (e.g. cyclobutyl isomers like cyclobutyl and methylcyclopropyl), $C_5H_9$ (e.g. cyclopentyl isomers like cyclopentyl, methylcyclobutyl, and dimethylcyclopropyl) $C_6H_{11}$ (e.g. cyclohexyl isomers), and $C_7H_{13}$ (e.g. cycloheptyl isomers).

As used herein, the term "diene" refers to a functional group comprising a straight-chain or branched-chain hydrocarbon with two carbon-carbon double bonds and having the general formula of $CnH_2n-2$. A diene can be unconjugated, conjugated or cumulative. Examples of diene groups include, without limitation, allene (propan-1,2-diene), 1,3-butadiene, chloroprene, hexachlorobutadiene, isoprene (2-methyl-1,3-butadiene), isotoluene, myrcenol, and piperylene. As used herein, the term "cyclodiene" refers to a functional group comprising a substituted or unsubstituted non-aromatic hydrocarbon with a cyclic molecular ring structure of 3 to 12 carbon atoms and having two carbon-carbon double bonds in the carbon ring structure. A cyclodiene can be unconjugated, conjugated or cumulative. Examples of cyclodiene groups include, without limitation, cyclopentadiene, 1,5-cyclooctadiene, hexachlorocyclopentadiene, and methylcyclopentadiene. As used herein, the term "enone" refers to a functional group comprising an alkene and a keyone, and having the general formula RC(O)C(R')CR"R''', wherein R, R', R", and R''' are an organic moiety or group. As used herein, the term "ester" refers to a molecule comprising a carboxyl group or derivative thereof, and having the general formula RC(O)OR', wherein R and R' are an organic moeity or group. As used herein, the term "ether" refers to a molecule comprising an oxy group, and having the general formula ROR', wherein R and R' are an organic moeity or group.

As used herein, the term "halogen", "halo" or "halide" refers to a functional group or moiety comprising one or more halogens attached to an element or radical, like a monohalo, dihalo, or trihalo, such as F, Cl, Br, I, $F_2$, $Cl_2$, $Br_2$, $I_2$, $F_3$, $Cl_3$, $Br_3$, $I_3$, etc. Examples of a halide group includes, without limitation, fluoride (F), chloride (CI), bromide (Br), iodide (I), astatide (At), or ununseptide (Uus) and may also be referred to as fluoro, chloro, bromo, iodo, astato, or ununsepto. As used herein, the term "haloalkenyl" refers to a functional group comprising an alkenyl group where one of more of the hydrogen atoms is replaced by halogen atoms on the unsaturated carbon atoms. As used herein, the term "haloalkoxy" refers to a functional group comprising a haloalkyl group attached to the parent molecular moiety through an oxygen atom. As used herein, the term "haloalkyl" refers to a functional group comprising an alkyl group where one of more of the hydrogen atoms is replaced by halogen atoms. A haloalkyl can be a monohaloalkyl, a dihaloalkyl or a polyhaloalkyl. A monohaloalkyl group may have an iodo, bromo, chloro or fluoro atom within the group. A dihalo and polyhaloalkyl group may have two or more of the same halo atoms or a combination of different halo groups. Examples of haloalkyl groups include, without limitation, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. As used herein, the term "haloalkylene" refers to a functional group comprising a haloalkyl group attached at two or more positions. Examples of a haloalkylene group include, without limitation, fluoromethylene (—CFH—), difluoromethylene (—$CF_2$—), chloromethylene (—CHCl—) and the like.

As used herein, the term "heteroalkenyl" refers to a functional group or moiety comprising a straight-chain or branched-chain hydrocarbon containing from 2 to 20 atoms and having one or more carbon-carbon double bonds and not having any cyclic structure, where at least one atom in the ring structure is a carbon and at least one atom in the ring structure is N, O, S, or any combination thereof.

For example, a heteroalkenyl includes a straight-chain or branched-chain hydrocarbon containing at least one N O, S, or any combination thereof and containing 2-6 carbon atoms, 3-6 carbon atoms, 3-7 carbon atoms, 4-8 carbon atoms, and 5-10 carbon atoms. The non-carbon atoms can be at any interior position of the heteroalkenyl group, and up to two non-carbon atoms may be consecutive, such as, e.g., —$CH_2$—NH—$OCH_3$. In addition, the non-carbon atoms may optionally be oxidized and the nitrogen may optionally be quaternized. As used herein, "lower heteroalkenyl" refers to heteroalkenyl moieties having from 2 to about 6 carbon atoms. A heteroalkenyl group may be optionally substituted as defined herein.

As used herein, the term "heteroalkyl" or "heterocyclic" refers to a functional group or moiety comprising a straight-chain or branched-chain hydrocarbon containing from 1 to 20 atoms linked exclusively by single bonds, and not having any cyclic structure, where at least one atom in the chain is a carbon and at least one atom in the chain is N O, S, or any combination thereof. For example, a heteroalkyl includes a straight-chain or branched-chain hydrocarbon containing at least one N O, S, or any combination thereof and 1 to 6 carbon atoms, 2-6 carbon atoms, 3-6 carbon atoms, 4-7 carbon atoms, 5-10 carbon atoms, 5-9 carbon atoms, and 5-8 carbon atoms. The non-carbon atoms can be at any interior position of the heteroalkyl group, and up to two non-carbon atoms may be consecutive, such as, e.g., —CH$_2$—NH—OCH$_3$. In addition, the non-carbon atoms may optionally be oxidized and the nitrogen may optionally be quaternized. As used herein, "lower heteroalkyl" refers to heteroalkyl moieties having from 2 to about 6 carbon atoms. A heteroalkyl group may be optionally substituted as defined herein.

As used herein, the term "heteroaryl" refers to a functional group or moiety comprising an aromatic hydrocarbon with a conjugated cyclic molecular ring structure of 3 to 12 atoms, where at least one atom in the ring structure is a carbon and at least one atom in the ring structure is N, O, S, or any combination thereof including a conjugated cyclic molecular ring structure of 3 carbon atoms, 4 carbon atoms, 5 carbon atoms, 6 carbon atoms, 7 carbon atoms, 3-6 carbon atoms, 4-6 carbon atoms, 4-5 carbon atoms, 5-6 carbon atoms, and 4-7 carbon atoms. As used herein, "lower heteroaryl" refers to heteroaryl moieties having from 3 to about 6 carbon atoms. A heteroaryl group may be optionally substituted as defined herein. A heteroaryl group can be monocyclic, bicyclic or polycyclic, and may optionally include one to three additional ring structures, such as, e.g., an aryl, a cycloalkyl, a cycloalkenyl, a heterocycloalkyl, or a heterocycloalkenyl. Examples of heteroaryl groups include, without limitation, acridinyl, benzidolyl, benzimidazolyl, benzisoxazolyl, benzodioxinyl, dihydrobenzodioxinyl, benzodioxolyl, 1,3-benzodioxolyl, benzofuryl, benzoisoxazolyl, benzopyranyl, benzothiophenyl, benzo[c]thiophenyl, benzotriazolyl, benzoxadiazolyl, benzoxazolyl, benzothiadiazolyl, benzothiazolyl, benzothienyl, carbazolyl, chromonyl, cinnolinyl, dihydrocinnolinyl, coumarinyl, dibenzofuranyl, furopyridinyl, furyl, indolizinyl, indolyl, dihydroindolyl, imidazolyl, indazolyl, isobenzofuryl, isoindolyl, isoindolinyl, dihydroisoindolyl, isoquinolyl, dihydroisoquinolinyl, isoxazolyl, isothiazolyl, oxazolyl, oxadiazolyl, phenanthrolinyl, phenanthridinyl, purinyl, pyranyl, pyrazinyl, pyrazolyl, pyridyl, pyrimidinyl, pyridazinyl, pyrrolinyl, pyrrolyl, pyrrolopyridinyl, quinolyl, quinoxalinyl, quinazolinyl, tetrahydroquinolinyl, tetrazolopyridazinyl, tetrahydroisoquinolinyl, thiophenyl, thiazolyl, thiadiazolyl, thienopyridinyl, thienyl, thiophenyl, triazolyl, xanthenyl, and the like.

As used herein, the term "heterocycloalkenyl" refers to a functional group or moiety comprising a non-aromatic hydrocarbon with a non-conjugated cyclic molecular ring structure of 3 to 12 atoms having at least one double bond, where at least one atom in the ring structure is a carbon and at least one atom in the ring structure is N, O, S, or any combination thereof including a conjugated cyclic molecular ring structure of 3 carbon atoms, 4 carbon atoms, 5 carbon atoms, 6 carbon atoms, 7 carbon atoms, 3-6 carbon atoms, 4-6 carbon atoms, 4-5 carbon atoms, 5-6 carbon atoms, and 4-7 carbon atoms. As used herein, "lower heterocycloalkenyl" refers to heterocycloalkenyl moieties having from 3 to about 6 carbon atoms. A heterocycloalkenyl group may be optionally substituted as defined herein. A heterocycloalkenyl group can be monocyclic, bicyclic or polycyclic, and may optionally include one to three additional ring structures, such as, e.g., an aryl, a heteroaryl, a cycloalkyl, a heterocycloalkyl, or a cycloalkenyl.

As used herein, the term "heterocycloalkyl", "heterocyclicalkyl", and "heterocyclealkyl" refers to a functional group comprising a non-aromatic hydrocarbon with a non-conjugated cyclic molecular ring structure of 3 to 12 atoms linked exclusively with single bonds in the ring structure, where at least one atom in the ring structure is a carbon and at least one atom in the ring structure is N, O, S, or any combination thereof. As used herein, "lower heterocycloalkyl" refers to heterocycloalkyl moieties having from 3 to about 6 carbon atoms, including, without limitation, pyrrolidinyl, imidazolidinyl, pyrazolidinyl, piperidinyl, piperazinyl, and morpholinyl. A heterocycloalkyl group may be optionally substituted as defined herein. A heterocycloalkyl group can be monocyclic, bicyclic or polycyclic, and may optionally include one to three additional ring structures, such as, e.g., an aryl, a heteroaryl a cycloalkyl, a cycloalkenyl, or a heterocycloalkenyl. A heterocycle group may be optionally substituted unless specifically prohibited. Examples of such heterocycloalkyl groups include, without limitation, ariridinyl, azirinyl, diazirinyl, oxiranyl, oxirenyl, dioxiranyl, thiiranyl, thiirenyl, azetidinyl, azetyl, diazetidinyl, oxetanyl, oxetyl, dioxetanyl, dioxetenyl, thietanyl, thietyl, dithietanyl, dithietyl, pyrrolidinyl, pyrrolinyl, pyrrolyl, furanyl, dihydrofuranyl, tetrahydrofuranyl, tetrahydrothiophenyl, dihydrothiophenyl, thiophenyl, imidazolidinyl, pyrazolidinyl, imidazolyl, imidazolinyl, pyrazolyl, pyrazolinyl, oxazolidinyl, isoxazolidinyl, oxazolyl, oxazolinyl, isoxazolyl, isoxazolinyl, thiazolidinyl, isothiazolidinyl, thiazolyl, thiazolinyl, isothiazolyl, isothiazolinyl, dioxolanyl, 1,3-dioxanyl, 1,4-dioxanyl, dioxolanyl, 1,3-dioxolanyl, oxathiolanyl, dithiolanyl, triazolyl, dithiazolyl, furazanyl, oxadiazolyl, thiadiazolyl, tetrazolyl, piperidinyl, tetrahydropyridinyl, pyridinyl, dihydropyridinyl, dihydro[1,3]oxazolo[4,5-b]pyridinyl, pyranyl, tetrahydropyranyl, thianyl, thiopyranyl, piperazinyl, diazinyl, morpholinyl, thiomorpholinyl, oxazinyl, thiazinyl, dithianyl, dioxanyl, dioxinyl, triazinyl, trioxanyl, tetrazinyl, azepanyl, azepinyl, oxepanyl, oxepinyl, thiepanyl, thiepinyl, diazepinyl, thiazepinyl, azocanyl, azocinyl, oxecanyl, and thiocanyl.

As used herein, the term "hydroxyalkyl" refers to a functional group comprising a hydroxy group attached to the parent molecular moiety through an alkyl group. As used herein, the term "oxyalkyl" refers to a functional group comprising an alkyl group attached to the parent molecular moiety through an oxy group. As used herein, the term "oxoalkyl" refers to a functional group comprising an alkyl group attached to the parent molecular moiety through an oxo group. As used herein, the term "oxime" refers to a molecule comprising an imine group (C=N) and having the general formula RR'C=NOH, wherein R and R' are an organic moeity or group. An oxime where R or R' is a hydrogen is oximine is called an aldoxime, whereas when both R and R' are not hydrogens, the oxime is called a ketooxime. As used herein, the term "perhaloalkoxy" refers to a functional group comprising an alkoxy group where all of the hydrogen atoms are replaced by halogen atoms. As used herein, the term "perhaloalkyl" refers to a functional group comprising an alkyl group where all of the hydrogen atoms are replaced by halogen atoms. As used herein, the term "thioalkyl" refers to a functional group comprising an alkyl group attached to the parent molecular moiety through a thio group.

Unless otherwise indicated, when a compound or chemical structural feature, such as functional group or moiety, is referred to as being "optionally substituted," it includes a feature that has no substituents (i.e. be unsubstituted), or a feature that is "substituted," meaning that the feature has one or more substituents. The term "substituent" has the broadest meaning known to one of ordinary skill in the art, and includes a functional group or moiety that replaces one or more hydrogen atoms attached to a parent compound or structural feature. Thus, an optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in between fully substituted and monosubstituted (e.g., —CH$_2$CH$_2$F, —CHFCH$_2$F, —CH$_2$CHF$_2$, —CHFCHF$_2$). In some embodiments, the substituent may be an ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In some embodiments, the substituent comprises: 0-30, 0-20, 0-10, or 0-5 carbon atoms; and 0-30, 0-20, 0-10, or 0-5 heteroatoms independently selected from: N, O, S, Si, F, Cl, Br, or I; provided that the substituent comprises at least one atom selected from: C, N, O, S, Si, F, Cl, Br, or I. Examples of substituents include, but are not limited to acid anhydride, acetyl, acyl, acylamino, acyl halide, acyloxy, alkenyl, alkoxy, alkyl, alkylamino, alkylcarbonyl, alkylcarboxylate, alkyloxy, alkyloxo, alkylthio, alkynyl, amide [—C(=O)NH$_2$], amidine (—C(=NH)NH$_2$), amido (—C(=O)—N), amino (—NH$_2$—), aminoalkyl, aryl, arylamino, arylalkenyl, arylalkoxy, arylalkyl, arylalkynyl, arylalkanoyl, aryloxy, arylthio, azide (—N=N=N), azo (—N=N—), benzo (C$_6$H$_4$), carbamyl [—NHC(=O)O—], carbonyl [—C(=O)H or the corresponding "carbonylate" anion —C(=O)—], carboxyl [—C(=O)OH or the corresponding "carboxylate" anion —C(=O)O$^-$], carboxamide (—C(=O)NH$_2$), carboxamidine (—C(=NH)NH$_2$), cyanate [—(OC=N)$^-$], cyano (—C=N), cycloalkenyl, cycloalkyl, diene, cyclodiene, disulfanyl (—S=S—), enone, halide, halo, haloalkenyl, haloalkoxyl, haloalkyl, halogen, heteroalkenyl, heteroalkyl, heteroalkynyl, heteroaryl, heterocycloalkenyl, heterocycloalkyl, hydrazinyl (—NHNH$_2$—), hydrazine (—C=N—), hydrogen (H), hydroperoxide (—OOH), hydroxyl (—OH), hydroxyalkyl, imidate (C=N—), imide [—C(=O)NC(=O)—], imine (—C=NH—), imino (=NH—), iminohydroxy (=N(OH) and its corresponding anion =N—O—), isocyanato (—NCO), isothiocyanato (—NCS), isocyanate (—N=C=O), isocyanide (—NEC), isothiocyanate (—N=C=S), keto (—C=O), mercaptyl (—S—), nitrile (—C≡N), nitrite (—NO$_2^-$), nitroso (—N=O), nitro (—NO$_2$), nitrate (—NO$_3^-$), oxo (=O), oxy (—O—), oxoalkyl, oxyalkyl, oxime, perhaloalkoxy, perhaloalkyl, peroxy (—OO—), silyl, sulfanyl (—S—), sulfenyl, sulfhydryl (—SH), sulfinyl[—S(O)—], sulfonyl[—S(O)$_2$—], sulfyl [—S(O)$_3$—], sulfonamide [—S(O)$_2$N—], thioalkyl, thiocarbonyl [—C(S)H], thiocarbamyl (—OC(S)N—), thiocyanate [—(SC=N)$^-$], isothiocyanate (N=C=S), thiocyanato (CNS), thioketo (—C=S), thiol (S), trihalomethanesulfonyl (X$_3$CS(O)$_2$—, with X being a halogen), trihalomethanesulfonamido (X$_3$CS(O)$_2$N—, with X being a halogen), trihalomethoxy (X$_3$CO—, with X being a halogen), and all lower forms therein.

In some embodiments, any substituent may independently be C$_{1-5}$ alkyl, such as CH$_3$, C$_2$H$_5$, C$_3$H$_7$, C$_4$H$_9$, C$_5$H$_{11}$, cyclopropyl, cyclobutyl, cyclopentyl, etc.; C$_{1-4}$—O-alkyl, such as —O—CH$_3$, —O—C$_2$H$_5$, —O—C$_3$H$_7$, —O-cyclopropyl, etc.; C$_{2-4}$ alkenyl, such as —CH$_2$—CH=CH$_2$; —O—CH$_2$CH=CH$_2$; ester functional groups, such as C$_{1-4}$—CO$_2$-alkyl (e.g. —CO$_2$CH$_3$, —CO$_2$C$_2$H$_5$, —CO$_2$C$_3$H$_7$, etc.), C$_{1-4}$ acyloxy, (e.g. —OCOCH$_3$, —OCOC$_2$H$_5$, —OCOC$_3$H$_7$, etc.), —CO$_2$—CF$_3$, etc.; halo, like a monohalo, dihalo, or trihalo, such as F, Cl, Br, I, F$_2$, Cl$_2$, Br$_2$, I$_2$, F$_3$, Cl$_3$, Br$_3$, I$_3$, etc.; NO$_2$; =O; =S; —OH; amino, such as C$_{1-12}$ amino including NH$_2$, NHCH$_3$, N(CH$_3$)$_2$, N(C$_2$H$_5$)$_2$, NH(C$_3$H$_7$), etc.; amide functional groups, such as C$_{1-12}$ amide groups including —CONH$_2$, CONH(CH$_3$), CON(CH$_3$)$_2$, CON(C$_2$H$_5$)$_2$, —NCOC$_4$H$_9$, etc.; —C=N—OH; —C=N—CH$_3$; C$_{1-4}$ acyl, such as COH, COCH$_3$, COC$_2$H$_5$, etc.; COCF$_3$; —NCOC$_4$H$_9$; or two substituents may together be —CH$_2$—, —C$_2$H$_4$—, —C$_3$H$_6$—, —O—CH$_2$—, —O—C$_2$H$_4$—, —O—C$_3$H$_6$—, —CH$_2$—O—, —C$_2$H$_4$—O—, —C$_3$H$_6$—O—, —O—CH$_2$—O—, —O—C$_2$H$_4$—O—, or —O—C$_3$H$_6$—O—.

Unless otherwise indicated, any reference to a compound herein by structure, name, or any other means, includes pharmaceutically acceptable salts, such as sodium, potassium, and ammonium salts; alternate solid forms, such as polymorphs, solvates, hydrates, etc.; tautomers; or any other chemical species that may rapidly convert to a compound described herein under conditions in which the compounds are used as described herein.

In some embodiments, a honeybee repellant may be a compound of formula I, II, III, IV, or V:

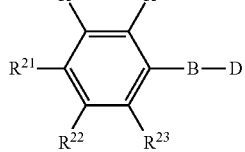

(I)

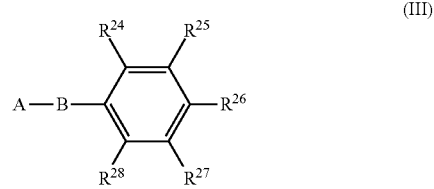

(II)

(III)

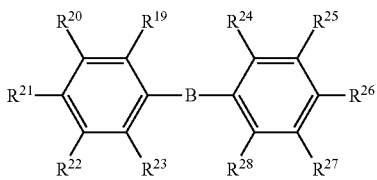

(IV)

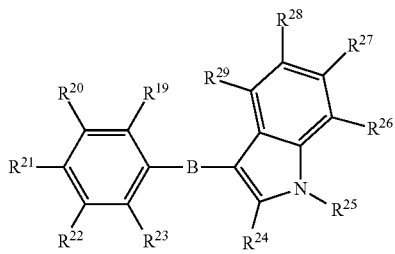

(V)

With respect to formulas I, II, III, IV, and V above, A is optionally substituted aryl or heteroaryl, such as optionally substituted phenyl. In some embodiments, any substituent of A may independently be $C_{1-6}$ alkyl, such as $CH_3$, $C_2H_5$, $C_3H_7$, $C_4H_9$, $C_5H_{11}$, $C_6H_{13}$, cyclopropyl, cyclobutyl, cyclopentyl, cyclohexyl, etc.; $C_{1-6}$—O-alkyl, such as —O—$CH_3$, —O—$C_2H_5$, —O—$C_3H_7$, —O—$C_4H_9$, —O—$C_5H_{11}$, —O—$C_6H_{13}$, —O-cyclopropyl, —O-cyclobutyl, —O-cyclopentyl, —O-cyclohexyl, etc; $C_{2-6}$ alkenyl, such as —$CH_2$—CH=$CH_2$; —O—$CH_2$CH=$CH_2$; ester functional groups, such as $C_{1-6}$—$CO_2$-alkyl (e.g. —$CO_2CH_3$, —$CO_2C_2H_5$, —$CO_2C_3H_7$, —$CO_2C_3H_7$, —$CO_2C_4H_9$, —$CO_2C_5H_{11}$, —$CO_2C_6H_{13}$ etc.), $C_{1-6}$ acyloxy, (e.g. —$OCOCH_3$, —$OCOC_2H_5$, —$OCOC_3H_7$, —$OCOC_4H_9$, —$OCOC_5H_{11}$, —$OCOC_6H_{13}$, etc.), $CF_3$, etc.; halo, such as F, Cl, Br, I, etc.; $NO_2$; —OH; $C_{1-12}$ amino, such as $NH_2$, $NHCH_3$, $N(CH_3)_2$, $N(C_2H_5)_2$, $NH(C_3H_7)$, etc.; $C_{1-12}$ amide functional groups such as —$CONH_2$, $CONH(CH_3)$, CON$(CH_3)_2$, $CON(C_2H_5)_2$, etc.; —C=N—OH; —C=N—$CH_3$; $C_{1-4}$ acyl, such as COH, $COCH_3$, $COC_2H_5$, etc.; $COCF_3$; methylpiperazinyl; etc.

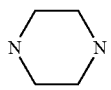 

piperazinyl       methylpiperazinyl

In some embodiments, A may be unsubstituted phenyl,

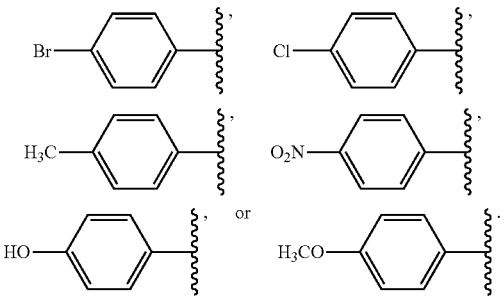

With respect to formulas I, II, III, IV, and V above, B is —$(CH_2)_h$—$B^1$—$(CH_2)_i$—; h is 0 or 1; i is 0 or 1; and $B^1$ is CH=CHCO; CH=CH; $CO_2$; O; S; NH; C=O; —$N(CH_2)_2O$—; —$N(CH_2)_2N$—; —$O(CH_2)_2O$—; —NH—NHCO; a heterocycle having 2, 3, 4, or 5 carbon atoms and 1, 2, or 3 nitrogen or oxygen atoms, such as piperazinyl, piperadinyl, furanyl, thienyl, pyridinyl, etc.; or a carbocycle having 3, 4, 5, 6, or 7 carbon atoms, such as cyclopentyl, cyclohexyl, phenyl, cycloheptyl, etc.

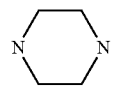

Piperazinyl

In some embodiments, B may be —O—,

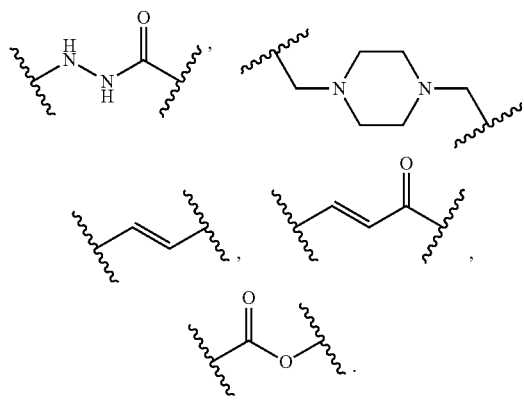

With respect to formulas I, II, III, IV, and V above, D is optionally substituted cycloalkenyl, aryl or heteroaryl, such as optionally substituted cyclopentenyl, optionally substituted phenyl, or optionally substituted indolyl, such as indol-3-yl. In some embodiments, any substituent of D may independently be $C_{1-6}$ alkyl, such as $CH_3$, $C_2H_5$, $C_3H_7$, $C_4H_9$, $C_5H_{11}$, $C_6H_{13}$, cyclopropyl, cyclobutyl, cyclopentyl, cyclohexyl, etc.; $C_{1-6}$—O-alkyl, such as —O—$CH_3$, —O—$C_2H_5$, —O—$C_3H_7$, —O—$C_4H_9$, —O—$C_5H_{11}$, —O—$C_6H_{13}$, —O-cyclopropyl, —O-cyclobutyl, —O-cyclopentyl, —O-cyclohexyl, etc; $C_{2-6}$ alkenyl, such as —$CH_2$—CH=$CH_2$; —O—$CH_2$CH=$CH_2$; ester functional groups, such as $C_{1-6}$—$CO_2$-alkyl (e.g. —$CO_2CH_3$, —$CO_2C_2H_5$, —$CO_2C_3H_7$, —$CO_2C_3H_7$, —$CO_2C_4H_9$, —$CO_2C_5H_{11}$, —$CO_2C_6H_{13}$ etc.), $C_{1-6}$ acyloxy, (e.g. —$OCOCH_3$, —$OCOC_2H_5$, —$OCOC_3H_7$, —$OCOC_4H_9$, —$OCOC_5H_{11}$, —$OCOC_6H_{13}$, etc.), $CF_3$, etc.; halo, such as F, Cl, Br, I, etc.; $NO_2$; —OH; $C_{1-12}$ amino, such as $NH_2$, $NHCH_3$, $N(CH_3)_2$, $N(C_2H_5)_2$, $NH(C_3H_7)$, etc.; $C_{1-12}$ amide functional groups such as —$CONH_2$, $CONH(CH_3)$, CON$(CH_3)_2$, $CON(C_2H_5)_2$, etc.; —C=N—OH; —C=N—$CH_3$; $C_{1-4}$ acyl, such as COH, $COCH_3$, $COC_2H_5$, etc.; $COCF_3$; methylpiperazinyl; etc.

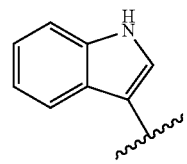

indol-3-yl

In some embodiments, D may be unsubstituted phenyl,

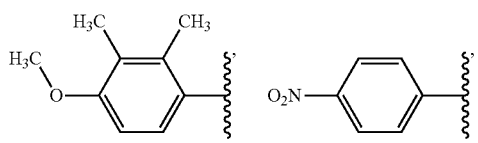

-continued

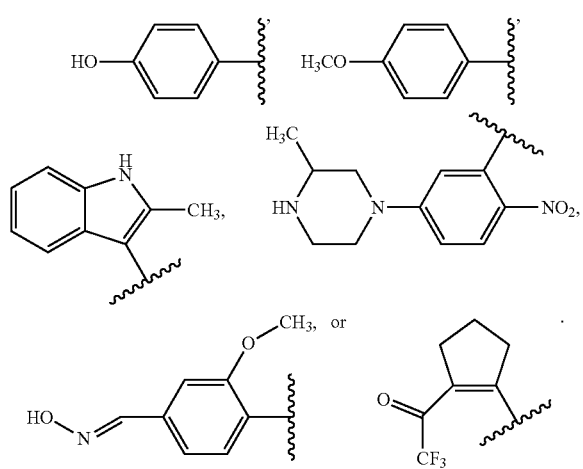

With respect to formulas I, II, III, IV, and V above, $R^{19}$, $R^{20}$, $R^{21}$, $R^{22}$, $R^{23}$, $R^{24}$, $R^{25}$, $R^{26}$, $R^{27}$, $R^{28}$, and $R^{29}$, are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, NO$_2$, NO$_3$, SH, S(O), S(O)$_2$, S(O)$_3$, S(O)$_2$N, aminoalkyl, halide, haloalkenyl, haloalkoxyl, haloalkyl, halogen, C(F)$_3$, C(Cl)$_3$, C(Br)$_3$, C(I)$_3$, trihalomethanesulfonyl, trihalomethanesulfonamido, trihalomethoxy, oxoalkyl, oxyalkyl, $C_{1-6}$ alkyl, $C_{2-6}$ alkenyl, $C_{2-6}$ alkynyl, OC$_{1-6}$ alkyl, OC$_{2-6}$ alkenyl, OC$_{2-6}$ alkynyl, CO$_2$C$_{1-6}$ alkyl, CO$_2$C$_{2-6}$ alkenyl, CO$_2$C$_{2-6}$ alkynyl, NC$_{1-6}$ alkyl, NC$_{2-6}$ alkenyl, NC$_{2-6}$ alkynyl, N(C$_{1-6}$ alkyl)$_2$, N(C$_{2-6}$ alkenyl)$_2$, or N(C$_{2-6}$ alkynyl)$_2$.

In another embodiment, a honeybee repellant may be a compound of formula VI:

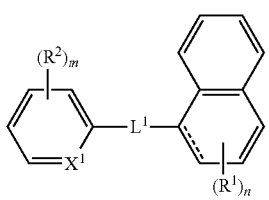

(VI)

wherein: $X^1$ is C, N, O or S; $L^1$ is NHN, NN, NCH, NC$_{1-6}$ alkyl, NC$_{2-6}$ alkenyl, NC$_{2-6}$ alkynyl, NHC$_{1-6}$ alkyl, NHC$_{2-6}$ alkenyl, NHC$_{2-6}$ alkynyl, NHNCH, NHNC$_{1-6}$ alkyl, NHNC$_{2-6}$ alkenyl, NHNC$_{2-6}$ alkynyl, CHN, CHNC$_{1-6}$ alkyl, CHNC$_{2-6}$ alkenyl, CHNC$_{2-6}$ alkynyl, CHNNH, CHNNHC$_{1-6}$ alkyl, CHNNHC$_{2-6}$ alkenyl, CHNNHC$_{2-6}$ alkynyl, aminoalkyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, or C(O)OC$_{2-6}$ alkynyl; $R^1$ is independently H, OH, OOH, O, OO, C(O), C(O)H, C(O)OH, OC(O)O, $C_{1-6}$ alkyl, $C_{2-6}$ alkenyl, $C_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, C(O)OC$_{2-6}$ alkynyl, halide, haloalkenyl, haloalkoxyl, haloalkyl, or halogen; $R^2$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, $C_{1-6}$ alkyl, $C_{2-6}$ alkenyl, $C_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, C(O)OC$_{2-6}$ alkynyl, an optionally substituted cycloalkyl or an optionally substituted heterocycloalkyl; m is 0 to 5; and n is 0 to 3.

In another embodiment, a honeybee repellant may be a compound of formula VIa:

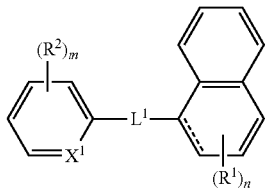

(VIa)

wherein: $X^1$ is C, N, or O; $L^1$ is NHN, NN, NCH, NC$_{1-6}$ alkyl, NC$_{2-6}$ alkenyl, NC$_{2-6}$ alkynyl, NHC$_{1-6}$ alkyl, NHC$_{2-6}$ alkenyl, NHC$_{2-6}$ alkynyl, NHNCH, NHNC$_{1-6}$ alkyl, NHNC$_{2-6}$ alkenyl, NHNC$_{2-6}$ alkynyl, CHN, CHNC$_{1-6}$ alkyl, CHNC$_{2-6}$ alkenyl, CHNC$_{2-6}$ alkynyl, CHNNH, CHNNHC$_{1-6}$ alkyl, CHNNHC$_{2-6}$ alkenyl, CHNNHC$_{2-6}$ alkynyl, aminoalkyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, or C(O)OC$_{2-6}$ alkynyl; $R^1$ is independently H, OH, OOH, O, OO, C(O), C(O)H, C(O)OH, OC(O)O, $C_{1-6}$ alkyl, $C_{2-6}$ alkenyl, $C_{2-6}$ alkynyl, OC$_{1-6}$ alkyl, OC$_{2-6}$ alkenyl, OC$_{2-6}$ alkynyl, halide, or halogen; $R^2$ is independently H, OH, OOH, O, OO, C(O), C(O)H, C(O)OH, OC(O)O, halide, halogen, $C_{1-6}$ alkyl, $C_{2-6}$ alkenyl, $C_{2-6}$ alkynyl, OC$_{1-6}$ alkyl, OC$_{2-6}$ alkenyl, OC$_{2-6}$ alkynyl, an optionally substituted cycloalkyl or an optionally substituted heterocycloalkyl; m is 0 to 5; and n is 0 to 3.

In aspects of this embodiment, a honeybee repellant may be a compound of formula VIb:

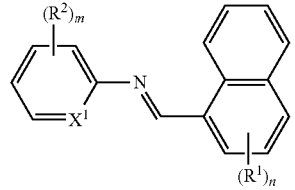

(VIb)

wherein: $X^1$ is C, N, O or S; $R^1$ is independently H, OH, OOH, O, OO, C(O), C(O)H, C(O)OH, OC(O)O, $C_{1-6}$ alkyl, $C_{2-6}$ alkenyl, $C_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, C(O)OC$_{2-6}$ alkynyl, halide, haloalkenyl, haloalkoxyl, haloalkyl, or halogen; $R^2$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, $C(O)OC_{2-6}$ alkynyl, an optionally substituted cycloalkyl or an optionally substituted heterocycloalkyl; m is 0 to 5; and n is 0 to 3.

In aspects of this embodiment, a honeybee repellant may be a compound of formula VIc:

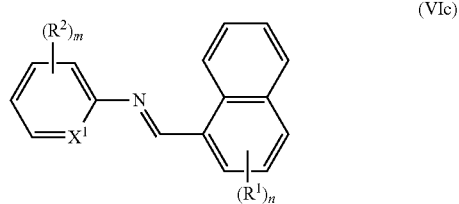

(VIc)

wherein: $X^1$ is C, N, or O; $R^1$ is independently H, OH, OOH, O, OO, C(O), C(O)H, C(O)OH, OC(O)O, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, halide, or halogen; $R^2$ is independently H, OH, OOH, O, OO, C(O), C(O)H, C(O)OH, OC(O)O, halide, halogen, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, an optionally substituted cycloalkyl or an optionally substituted heterocycloalkyl; m is 0 to 5; and n is 0 to 3.

In aspects of this embodiment, a honeybee repellant may be a compound of formula VId:

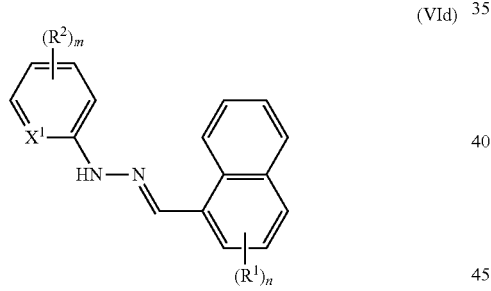

(VId)

wherein: $X^1$ is C, N, O or S; $R^1$ is independently H, OH, OOH, O, OO, C(O), C(O)H, C(O)OH, OC(O)O, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, $C(O)OC_{2-6}$ alkynyl, halide, haloalkenyl, haloalkoxyl, haloalkyl, or halogen; $R^2$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, $C(O)OC_{2-6}$ alkynyl, an optionally substituted cycloalkyl or an optionally substituted heterocycloalkyl; m is 0 to 5; and n is 0 to 3.

In aspects of this embodiment, a honeybee repellant may be a compound of formula VIe:

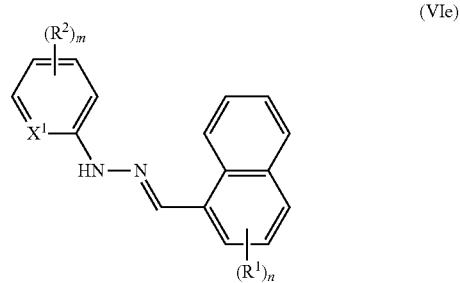

(VIe)

wherein: $X^1$ is C, N, or O; $R^1$ is independently H, OH, OOH, O, OO, C(O), C(O)H, C(O)OH, OC(O)O, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, halide, or halogen; $R^2$ is independently H, OH, OOH, O, OO, C(O), C(O)H, C(O)OH, OC(O)O, halide, halogen, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, an optionally substituted cycloalkyl or an optionally substituted heterocycloalkyl; m is 0 to 5; and n is 0 to 3.

In aspects of this embodiment, a honeybee repellant may be a compound of formula VIf:

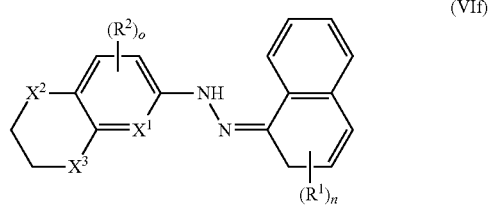

(VIf)

wherein: $X^1$, $X^2$ and $X^3$ are each independently C, N, O or S; $R^1$ is independently H, OH, OOH, O, OO, C(O), C(O)H, C(O)OH, OC(O)O, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, $C(O)OC_{2-6}$ alkynyl, halide, haloalkenyl, haloalkoxyl, haloalkyl, or halogen; $R^2$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, or $C(O)OC_{2-6}$ alkynyl; n is 0 to 3; and o is 0 to 3.

In aspects of this embodiment, a honeybee repellant may be a compound of formula VIg:

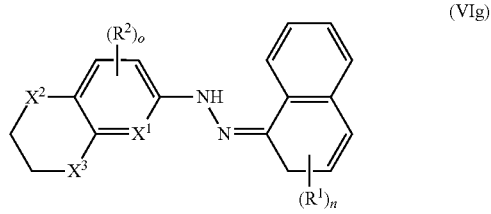

(VIg)

wherein: $X^1$, $X^2$ and $X^3$ are each independently C, N, or O; $R^1$ is independently H, OH, OOH, O, OO, C(O), C(O)H, C(O)OH, OC(O)O, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, halide, or halogen; $R^2$ is independently H, OH, OOH, O, OO, C(O), C(O)H, C(O)OH, OC(O)O, halide, halogen, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, an optionally substituted cycloalkyl or an optionally substituted heterocycloalkyl; n is 0 to 3; and o is 0 to 3.

In aspects of this embodiment, a honeybee repellant of formula VI disclosed herein is an optionally substituted 1-{[(4-iodophenyl)imino]methyl}-2-naphthol, an optionally substituted (2,5-dimethylphenyl)[(2-methoxy-1-naphthyl) methylene]amine, an optionally substituted 2-hydroxy-1-naphthaldehyde 2-pyridinylhydrazone or an optionally substituted 1,2-naphthalenedione 1-(2,3-dihydro-1,4-benzodioxin-6-ylhydrazone).

In aspects of this embodiment, a honeybee repellant of formula VI disclosed herein is

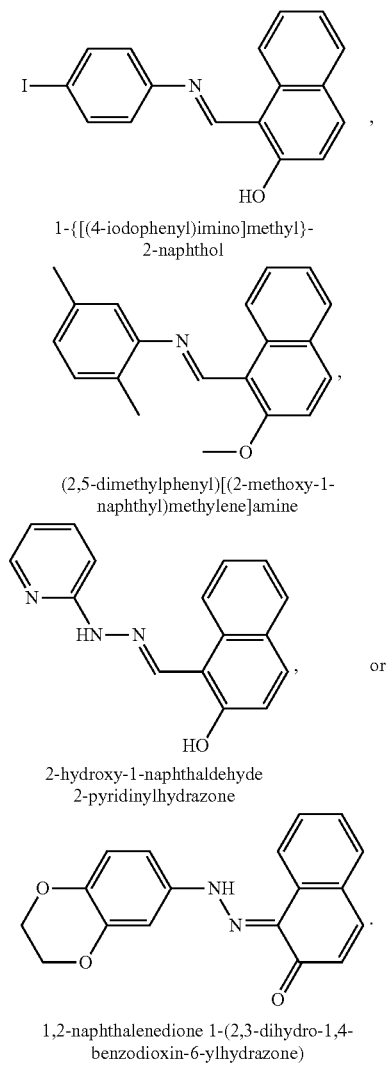

1-{[(4-iodophenyl)imino]methyl}-2-naphthol (2,5-dimethylphenyl)[(2-methoxy-1-naphthyl)methylene]amine 2-hydroxy-1-naphthaldehyde 2-pyridinylhydrazone 1,2-naphthalenedione 1-(2,3-dihydro-1,4-benzodioxin-6-ylhydrazone)

In aspects of this embodiment, a honeybee repellant is not 1-{[(4-iodophenyl)imino]methyl}-2-naphthol, (2,5-dimethylphenyl)[(2-methoxy-1-naphthyl)methylene]amine, 2-hydroxy-1-naphthaldehyde 2-pyridinylhydrazone or 1,2-naphthalenedione 1-(2,3-dihydro-1,4-benzodioxin-6-ylhydrazone).

In another embodiment, a honeybee repellant may be a compound of formula VII:

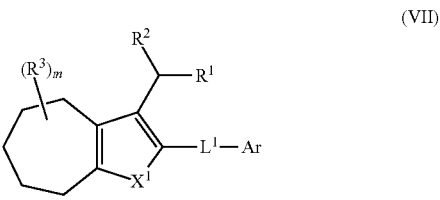

(VII)

wherein: $X^1$ is C, N, O or S; $L^1$ is NHC(O), $NHC(O)C_{1-6}$ alkyl, $NHC(O)C_{2-6}$ alkenyl, $NHC(O)C_{2-6}$ alkynyl, NC(O) $C_{1-6}$ alkyl, $NC(O)C_{2-6}$ alkenyl, $NC(O)C_{2-6}$ alkynyl, C(O) $NHC_{1-6}$ alkyl, $C(O)NHC_{2-6}$ alkenyl, $C(O)NHC_{2-6}$ alkynyl, $C(O)NC_{1-6}$ alkyl, $C(O)NC_{2-6}$ alkenyl, $C(O)NC_{2-6}$ alkynyl, NHN, NN, NCH, $NC_{1-6}$ alkyl, $NC_{2-6}$ alkenyl, $NC_{2-6}$ alkynyl, $NHC_{1-6}$ alkyl, $NHC_{2-6}$ alkenyl, $NHC_{2-6}$ alkynyl, NHNCH, $NHNC_{1-6}$ alkyl, $NHNC_{2-6}$ alkenyl, $NHNC_{2-6}$ alkynyl, CHN, $CHNC_{1-6}$ alkyl, $CHNC_{2-6}$ alkenyl, $CHNC_{2-6}$ alkynyl, CHNNH, $CHNNHC_{1-6}$ alkyl, $CHNNHC_{2-6}$ alkenyl, $CHNNHC_{2-6}$ alkynyl, aminoalkyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, or $C(O)OC_{2-6}$ alkynyl; Ar is an optionally substituted 4-7-member aryl, an optionally substituted 4-7-member heteroaryl, an optionally substituted 4-7-member cycloalkyl, or an optionally substituted 4-7-member heterocycloalkyl; $R^1$ is $N(C_{1-6}$ alkyl$)_2$, $N(C_{2-6}$ alkenyl$)_2$, $N(C_{2-6}$ alkynyl$)_2$, NHC $(C_{1-6}$ alkyl$)_2$, $NHC(C_{2-6}$ alkenyl$)_2$, $NHC(C_{2-6}$ alkynyl$)_2$, $NHN(C_{1-6}$alkyl$)_2$, $NHN(C_{2-6}$ alkenyl$)_2$, $NHN(C_{2-6}$ alkynyl$)_2$, $ONH(C_{1-6}$ alkyl$)_2$, $ONH(C_{2-6}$ alkenyl$)_2$, ONH $(C_{2-6}$ alkynyl$)_2$, $NHCOH(C_{1-6}$ alkyl$)_2$, $NHCOH(C_{2-6}$ alkenyl$)_2$, $NHCOH(C_{2-6}$ alkynyl$)_2$, $C_{1-6}$ alkyl$N(C_{1-6}$ alkyl$)_2$, $C_{1-6}$ alkyl$N(C_{2-6}$ alkenyl$)_2$, $C_{1-6}$ alkyl$N(C_{2-6}$ alkynyl$)_2$, $C_{2-6}$ alkenyl$N(C_{1-6}$ alkyl$)_2$, $C_{2-6}$ alkenyl$N(C_{2-6}$ alkenyl$)_2$, $C_{2-6}$ alkenyl$N(C_{2-6}$ alkynyl$)_2$, $C_{2-6}$ alkynyl$N(C_{1-6}$ alkyl$)_2$, $C_{2-6}$ alkynyl$N(C_{2-6}$ alkenyl$)_2$, $C_{2-6}$ alkynyl$N(C_{2-6}$ alkynyl$)_2$, an optionally substituted 4-7-member aryl, an optionally substituted 4-7-member heteroaryl, an optionally substituted 4-7-member cycloalkyl, or an optionally substituted 4-7-member heterocycloalkyl; $R^2$ is H, OH, OOH, O, OO, C(O), C(O)H, C(O)OH, OC(O)O, $C(O)NH_2$, C(O)NC(O), C(NH) $NH_2$, CN, CNH, C(O)N, OCN, NHC(O)O, CS, C(S)H, OC(S)N, SCN, CNS, (N)C(S), NH, $NH_2$, $NHNH_2$, NNN, NN, N(OH), NC, NCO, (N)C(O), NCS, (N)C(S), NO, $N(O)_2$, $N(O)_3$, SH, S(O), $S(O)_2$, $S(O)_3$, $S(O)_2N$, aminoalkyl, halide, haloalkenyl, haloalkoxyl, haloalkyl, halogen, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, or $C(O)OC_{2-6}$ alkynyl; $R^3$ is independently H, OH, OOH, O, OO, C(O), C(O)H, C(O)OH, OC(O)O, $C(O)NH_2$, C(O)NC (O), $C(NH)NH_2$, CN, CNH, C(O)N, OCN, NHC(O)O, CS, C(S)H, OC(S)N, SCN, CNS, (N)C(S), NH, $NH_2$, $NHNH_2$, NNN, NN, N(OH), NC, NCO, (N)C(O), NCS, (N)C(S), NO, $N(O)_2$, $N(O)_3$, SH, S(O), $S(O)_2$, $S(O)_3$, $S(O)_2N$, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, C(O)OC$_{1-6}$ alkyl, C(O)OC$_{2-6}$ alkenyl, C(O)OC$_{2-6}$alkynyl, an optionally substituted cycloalkyl or an optionally substituted heterocycloalkyl and m is 0 to 5.

In aspects of this embodiment, a honeybee repellant may be a compound of formula VIIa:

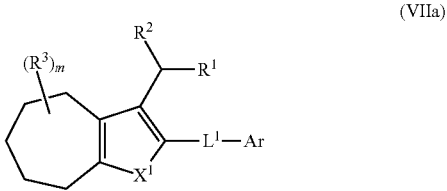

(VIIa)

wherein: X$^1$ is C, N, or O; L$^1$ is NHC(O), NHC(O)C$_{1-6}$ alkyl, NHC(O)C$_{2-6}$ alkenyl, NHC(O)C$_{2-6}$ alkynyl, NC(O)C$_{1-6}$ alkyl, NC(O)C$_{2-6}$ alkenyl, NC(O)C$_{2-6}$ alkynyl, C(O)NHC$_{1-6}$ alkyl, C(O)NHC$_{2-6}$ alkenyl, C(O)NHC$_{2-6}$ alkynyl, C(O)NC$_{1-6}$ alkyl, C(O)NC$_{2-6}$ alkenyl, C(O)NC$_{2-6}$ alkynyl, NHN, NN, NCH, NC$_{1-6}$ alkyl, NC$_{2-6}$ alkenyl, NC$_{2-6}$ alkynyl, NHC$_{1-6}$ alkyl, NHC$_{2-6}$ alkenyl, NHC$_{2-6}$ alkynyl, NHNCH, NHNC$_{1-6}$ alkyl, NHNC$_{2-6}$ alkenyl, or NHNC$_{2-6}$ alkynyl; Ar is an optionally substituted 4-7-member aryl, or an optionally substituted 4-7-member heteroaryl; R$^1$ is N(C$_{1-6}$ alkyl)$_2$, N(C$_{2-6}$ alkenyl)$_2$, N(C$_{2-6}$ alkynyl)$_2$, NHC(C$_{1-6}$ alkyl)$_2$, NHC(C$_{2-6}$ alkenyl)$_2$, NHC(C$_{2-6}$ alkynyl)$_2$, NHN(C$_{1-6}$ alkyl)$_2$, NHN(C$_{2-6}$ alkenyl)$_2$, NHN(C$_{2-6}$ alkynyl)$_2$, ONH(C$_{1-6}$ alkyl)$_2$, ONH(C$_{2-6}$ alkenyl)$_2$, ONH(C$_{2-6}$ alkynyl)$_2$, NHCOH(C$_{1-6}$ alkyl)$_2$, NHCOH(C$_{2-6}$ alkenyl)$_2$, NHCOH(C$_{2-6}$ alkynyl)$_2$, an optionally substituted 4-7-member aryl, or an optionally substituted 4-7-member heteroaryl; R$^2$ is H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, halide, halogen, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, or C(O)OC$_{2-6}$ alkynyl; R$^3$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, halide, halogen, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, C(O)OC$_{2-6}$ alkynyl, an optionally substituted cycloalkyl or an optionally substituted heterocycloalkyl; and m is 0 to 5.

In aspects of this embodiment, a honeybee repellant may be a compound of formula VIIb:

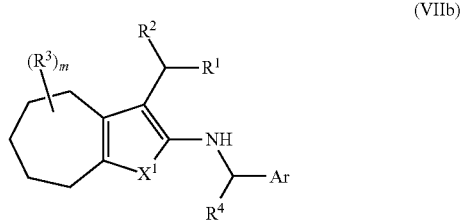

(VIIb)

wherein: X$^1$ is C, N, O or S; Ar is an optionally substituted 4-7-member aryl, an optionally substituted 4-7-member heteroaryl, an optionally substituted 4-7-member cycloalkyl, or an optionally substituted 4-7-member heterocycloalkyl; R$^1$ is N(C$_{1-6}$ alkyl)$_2$, N(C$_{2-6}$ alkenyl)$_2$, N(C$_{2-6}$ alkynyl)$_2$, NHC(C$_{1-6}$ alkyl)$_2$, NHC(C$_{2-6}$ alkenyl)$_2$, NHC(C$_{2-6}$ alkynyl)$_2$, NHN(C$_{1-6}$ alkyl)$_2$, NHN(C$_{2-6}$ alkenyl)$_2$, NHN(C$_{2-6}$ alkynyl)$_2$, ONH(C$_{1-6}$ alkyl)$_2$, ONH(C$_{2-6}$ alkenyl)$_2$, ONH(C$_{2-6}$ alkynyl)$_2$, NHCOH(C$_{1-6}$ alkyl)$_2$, NHCOH(C$_{2-6}$ alkenyl)$_2$, NHCOH(C$_{2-6}$ alkynyl)$_2$, C$_{1-6}$ alkylN(C$_{1-6}$ alkyl)$_2$, C$_{1-6}$ alkylN(C$_{2-6}$ alkenyl)$_2$, C$_{1-6}$ alkylN(C$_{2-6}$ alkynyl)$_2$, C$_{2-6}$ alkenylN(C$_{1-6}$ alkyl)$_2$, C$_{2-6}$ alkenylN(C$_{2-6}$ alkenyl)$_2$, C$_{2-6}$ alkenylN(C$_{2-6}$ alkynyl)$_2$, C$_{2-6}$ alkynylN(C$_{1-6}$ alkyl)$_2$, C$_{2-6}$ alkynylN(C$_{2-6}$ alkenyl)$_2$, C$_{2-6}$ alkynylN(C$_{2-6}$ alkynyl)$_2$, an optionally substituted 4-7-member aryl, an optionally substituted 4-7-member heteroaryl, an optionally substituted 4-7-member cycloalkyl, or an optionally substituted 4-7-member heterocycloalkyl; R$^2$ and R$^4$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, C(O)OC$_{2-6}$ alkynyl, an optionally substituted cycloalkyl or an optionally substituted heterocycloalkyl; R$^3$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, C(O)OC$_{2-6}$ alkynyl, an optionally substituted cycloalkyl or an optionally substituted heterocycloalkyl; and m is 0 to 5.

In aspects of this embodiment, a honeybee repellant may be a compound of formula VIIc:

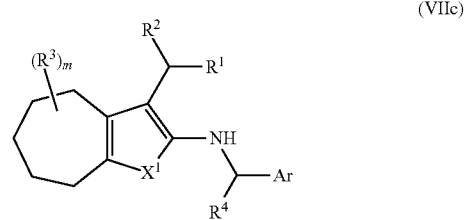

(VIIc)

wherein: X$^1$ is C, N, or O; Ar is an optionally substituted 4-7-member aryl, an optionally substituted 4-7-member heteroaryl; R$^1$ is N(C$_{1-6}$ alkyl)$_2$, N(C$_{2-6}$ alkenyl)$_2$, N(C$_{2-6}$ alkynyl)$_2$, NHC(C$_{1-6}$ alkyl)$_2$, NHC(C$_{2-6}$ alkenyl)$_2$, NHC(C$_{2-6}$ alkynyl)$_2$, NHN(C$_{1-6}$ alkyl)$_2$, NHN(C$_{2-6}$ alkenyl)$_2$, NHN(C$_{2-6}$ alkynyl)$_2$, ONH(C$_{1-6}$ alkyl)$_2$, ONH(C$_{2-6}$ alkenyl)$_2$, ONH(C$_{2-6}$ alkynyl)$_2$, NHCOH(C$_{1-6}$ alkyl)$_2$, NHCOH(C$_{2-6}$ alkenyl)$_2$, NHCOH(C$_{2-6}$ alkynyl)$_2$, an optionally substituted 4-7-member aryl, or an optionally substituted 4-7-member heteroaryl; R$^2$ and R$^4$ are each independently H, OH, OOH, O, OO, C(O), C(O)H, C(O)OH, OC(O)O, C(O)NH₂, C(O)NC(O), C(NH)NH₂, CN, CNH, C(O)N, OCN, NHC(O)O, CS, C(S)H, OC(S)N, SCN, CNS, (N)C(S), NH, NH₂, NHNH₂, NNN, NN, N(OH), NC, NCO, (N)C(O), NCS, (N)C(S), NO, N(O)₂, N(O)₃, halide, halogen, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, or $C(O)OC_{2-6}$ alkynyl; R³ is independently H, OH, OOH, O, OO, C(O), C(O)H, C(O)OH, OC(O)O, C(O)NH₂, C(O)NC(O), C(NH)NH₂, CN, CNH, C(O)N, OCN, NHC(O)O, CS, C(S)H, OC(S)N, SCN, CNS, (N)C(S), NH, NH₂, NHNH₂, NNN, NN, N(OH), NC, NCO, (N)C(O), NCS, (N)C(S), NO, N(O)₂, N(O)₃, halide, halogen, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, $C(O)OC_{2-6}$ alkynyl, an optionally substituted cycloalkyl or an optionally substituted heterocycloalkyl; and m is 0 to 5.

In aspects of this embodiment, a honeybee repellant may be a compound of formula VIId:

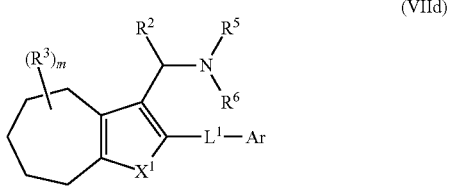

(VIId)

wherein: X¹ is C, N, O or S; L¹ is NHC(O), NHC(O)$C_{1-6}$ alkyl, NHC(O)$C_{2-6}$ alkenyl, NHC(O)$C_{2-6}$ alkynyl, NC(O)$C_{1-6}$ alkyl, NC(O)$C_{2-6}$ alkenyl, NC(O)$C_{2-6}$ alkynyl, C(O)NHC$_{1-6}$ alkyl, C(O)NHC$_{2-6}$ alkenyl, C(O)NHC$_{2-6}$ alkynyl, C(O)NC$_{1-6}$ alkyl, C(O)NC$_{2-6}$ alkenyl, C(O)NC$_{2-6}$ alkynyl, NHN, NN, NCH, NC$_{1-6}$ alkyl, NC$_{2-6}$ alkenyl, NC$_{2-6}$ alkynyl, NHC$_{1-6}$ alkyl, NHC$_{2-6}$ alkenyl, NHC$_{2-6}$ alkynyl, NHNCH, NHNC$_{1-6}$ alkyl, NHNC$_{2-6}$ alkenyl, NHNC$_{2-6}$ alkynyl, CHN, CHNC$_{1-6}$ alkyl, CHNC$_{2-6}$ alkenyl, CHNC$_{2-6}$ alkynyl, CHNNH, CHNNHC$_{1-6}$ alkyl, CHNNHC$_{2-6}$ alkenyl, CHNNHC$_{2-6}$ alkynyl, aminoalkyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, or C(O)OC$_{2-6}$ alkynyl; Ar is an optionally substituted 4-7-member aryl, an optionally substituted 4-7-member heteroaryl, an optionally substituted 4-7-member cycloalkyl, or an optionally substituted 4-7-member heterocycloalkyl; R² is H, OH, OOH, O, OO, C(O), C(O)H, C(O)OH, OC(O)O, C(O)NH₂, C(O)NC(O), C(NH)NH₂, CN, CNH, C(O)N, OCN, NHC(O)O, CS, C(S)H, OC(S)N, SCN, CNS, (N)C(S), NH, NH₂, NHNH₂, NNN, NN, N(OH), NC, NCO, (N)C(O), NCS, (N)C(S), NO, N(O)₂, N(O)₃, SH, S(O), S(O)₂, S(O)₃, S(O)₂N, aminoalkyl, halide, haloalkenyl, haloalkoxyl, haloalkyl, halogen, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, or $C(O)OC_{2-6}$ alkynyl; R³ is independently H, OH, OOH, O, OO, C(O), C(O)H, C(O)OH, OC(O)O, C(O)NH₂, C(O)NC(O), C(NH)NH₂, CN, CNH, C(O)N, OCN, NHC(O)O, CS, C(S)H, OC(S)N, SCN, CNS, (N)C(S), NH, NH₂, NHNH₂, NNN, NN, N(OH), NC, NCO, (N)C(O), NCS, (N)C(S), NO, N(O)₂, N(O)₃, SH, S(O), S(O)₂, S(O)₃, S(O)₂N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, $C(O)OC_{2-6}$ alkynyl, an optionally substituted cycloalkyl or an optionally substituted heterocycloalkyl; R⁵ and R⁶ are each independently $C_{1-6}$ alkyl, $C_{2-6}$ alkenyl, or $C_{2-6}$ alkynyl; and m is 0 to 5.

In aspects of this embodiment, a honeybee repellant may be a compound of formula VIIe:

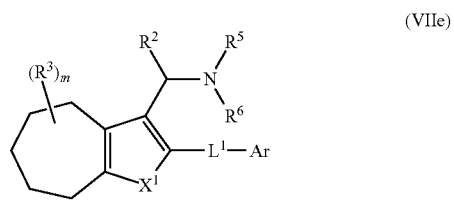

(VIIe)

wherein: X¹ is C, N, or O; L¹ is NHC(O), NHC(O)$C_{1-6}$ alkyl, NHC(O)$C_{2-6}$ alkenyl, NHC(O)$C_{2-6}$ alkynyl, NC(O)$C_{1-6}$ alkyl, NC(O)$C_{2-6}$ alkenyl, NC(O)$C_{2-6}$ alkynyl, C(O)NHC$_{1-6}$ alkyl, C(O)NHC$_{2-6}$ alkenyl, C(O)NHC$_{2-6}$ alkynyl, C(O)NC$_{1-6}$ alkyl, C(O)NC$_{2-6}$ alkenyl, C(O)NC$_{2-6}$ alkynyl, NHN, NN, NCH, NC$_{1-6}$ alkyl, NC$_{2-6}$ alkenyl, NC$_{2-6}$ alkynyl, NHC$_{1-6}$ alkyl, NHC$_{2-6}$ alkenyl, NHC$_{2-6}$ alkynyl, NHNCH, NHNC$_{1-6}$ alkyl, NHNC$_{2-6}$ alkenyl, NHNC$_{2-6}$ alkynyl; Ar is an optionally substituted 4-7-member aryl, or an optionally substituted 4-7-member heteroaryl; R² is H, OH, OOH, O, OO, C(O), C(O)H, C(O)OH, OC(O)O, C(O)NH₂, C(O)NC(O), C(NH)NH₂, CN, CNH, C(O)N, OCN, NHC(O)O, CS, C(S)H, OC(S)N, SCN, CNS, (N)C(S), NH, NH₂, NHNH₂, NNN, NN, N(OH), NC, NCO, (N)C(O), NCS, (N)C(S), NO, N(O)₂, N(O)₃, halide, halogen, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, or $C(O)OC_{2-6}$ alkynyl; R³ is independently H, OH, OOH, O, OO, C(O), C(O)H, C(O)OH, OC(O)O, C(O)NH₂, C(O)NC(O), C(NH)NH₂, CN, CNH, C(O)N, OCN, NHC(O)O, CS, C(S)H, OC(S)N, SCN, CNS, (N)C(S), NH, NH₂, NHNH₂, NNN, NN, N(OH), NC, NCO, (N)C(O), NCS, (N)C(S), NO, N(O)₂, N(O)₃, halide, halogen, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, $C(O)OC_{2-6}$ alkynyl, an optionally substituted cycloalkyl or an optionally substituted heterocycloalkyl; R⁵ and R⁶ are each independently Cis alkyl, $C_{2-6}$ alkenyl, or $C_{2-6}$ alkynyl; and m is 0 to 5.

In aspects of this embodiment, a honeybee repellant of formula VII disclosed herein may be an optionally substituted N-{3-[(diethylamino)carbonyl]-5,6,7,8-tetrahydro-4H-cyclohepta[b]thien-2-yl}-2-furamide, an optionally substituted N-(3-{[(4-methylphenyl)amino]carbonyl}-5,6,7,8-tetrahydro-4H-cyclohepta[b]thien-2-yl)-2-furamide, or an optionally substituted N-[3-(1-piperidinylcarbonyl)-5,6,7,8-tetrahydro-4H-cyclohepta[b]thien-2-yl]benzamide.

In aspects of this embodiment, a honeybee repellant of formula VII disclosed herein is

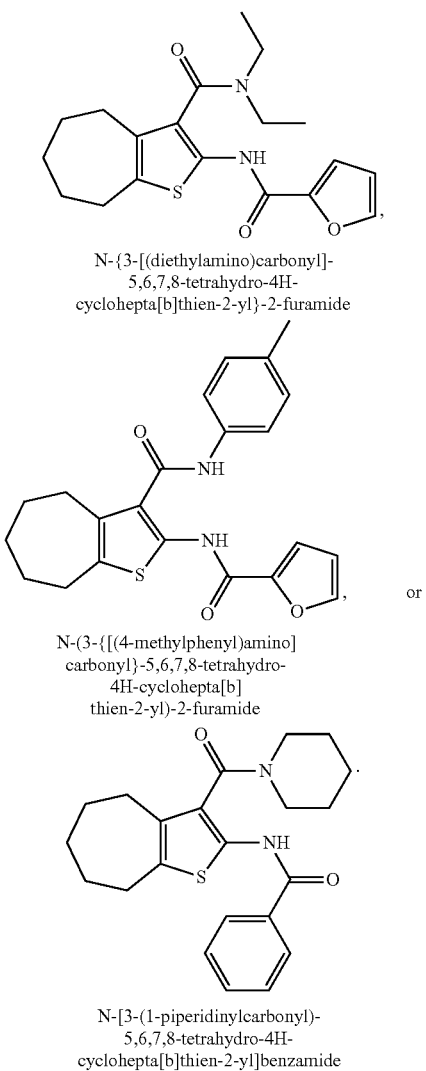

N-{3-[(diethylamino)carbonyl]-5,6,7,8-tetrahydro-4H-cyclohepta[b]thien-2-yl}-2-furamide N-(3-{[(4-methylphenyl)amino]carbonyl}-5,6,7,8-tetrahydro-4H-cyclohepta[b]thien-2-yl)-2-furamide, or N-[3-(1-piperidinylcarbonyl)-5,6,7,8-tetrahydro-4H-cyclohepta[b]thien-2-yl]benzamide In aspects of this embodiment, a honeybee repellant is not N-{3-[(diethylamino)carbonyl]-5,6,7,8-tetrahydro-4H-cyclohepta[b]thien-2-yl}-2-furamide, N-(3-{[(4-methylphenyl)amino]carbonyl}-5,6,7,8-tetrahydro-4H-cyclohepta[b]thien-2-yl)-2-furamide, or N-[3-(1-piperidinylcarbonyl)-5,6,7,8-tetrahydro-4H-cyclohepta[b]thien-2-yl]benzamide.

In another embodiment, a honeybee repellant may be a compound of formula VIII:

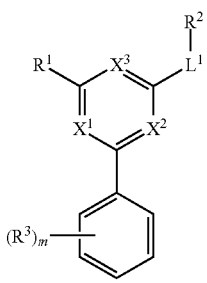

(VIII)

wherein: $X^1$, $X^2$, and $X^3$ are each independently C, N, O or S; $L^1$ is OH, OOH, O, OO, OHC, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHN, NHNH$_2$, NNN, NN, N(OH), NC, NCH, NHNCH, NCO, (N)C(O), NCS, (N)C(S), NO, N(O)$_2$, N(O)$_3$, S, SH, S(O), S(O)$_2$, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C_{1-6}$ alkylO, $C_{2-6}$ alkenylO, $C_{2-6}$ alkynylO, $OHC_{1-6}$ alkyl, $OHC_{2-6}$ alkenyl, $OHC_{2-6}$ alkynyl, OHC(O), $OHC(O)C_{1-6}$ alkyl, $OHC(O)C_{2-6}$ alkenyl, $OHC(O)C_{2-6}$ alkynyl, $OC(O)C_{1-6}$ alkyl, $OC(O)C_{2-6}$ alkenyl, $OC(O)C_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, $C(O)OC_{2-6}$ alkynyl, $NHNC_{1-6}$ alkyl, $NHNC_{2-6}$ alkenyl, $NHNC_{2-6}$ alkynyl, CHN, $CHNC_{1-6}$ alkyl, $CHNC_{2-6}$ alkenyl, $CHNC_{2-6}$ alkynyl, CHNNH, $CHNNHC_{1-6}$ alkyl, $CHNNHC_{2-6}$ alkenyl, $CHNNHC_{2-6}$ alkynyl, $NC_{1-6}$ alkyl, $NC_{2-6}$ alkenyl, $NC_{2-6}$ alkynyl, $NHC_{1-6}$ alkyl, $NHC_{2-6}$ alkenyl, $NHC_{2-6}$ alkynyl, NHC(O), $NHC(O)C_{1-6}$ alkyl, $NHC(O)C_{2-6}$ alkenyl, $NHC(O)C_{2-6}$ alkynyl, $NC(O)C_{1-6}$ alkyl, $NC(O)C_{2-6}$ alkenyl, $NC(O)C_{2-6}$ alkynyl, $C(O)NHC_{1-6}$ alkyl, $C(O)NHC_{2-6}$ alkenyl, $C(O)NHC_{2-6}$ alkynyl, $C(O)NC_{1-6}$ alkyl, $C(O)NC_{2-6}$ alkenyl, or $C(O)NC_{2-6}$ alkynyl; $R^1$ and $R^2$ are each independently an optionally substituted 4-7-member aryl, an optionally substituted 4-7-member heteroaryl, an optionally substituted 4-7-member cycloalkyl, or an optionally substituted 4-7-member heterocycloalkyl; $R^3$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, or $C(O)OC_{2-6}$ alkynyl; and m is 0 to 5.

In aspects of this embodiment, a honeybee repellant may be a compound of formula VIIIa:

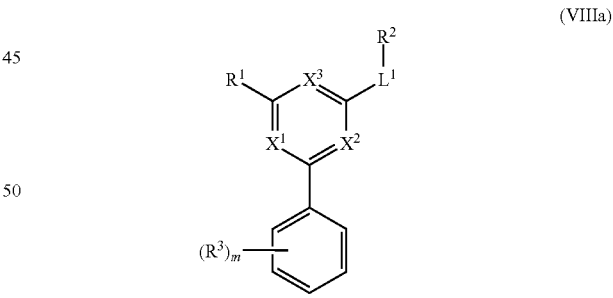

(VIIIa)

wherein: $X^1$, $X^2$, and $X^3$ are each independently C, N, or O; $L^1$ is OH, OOH, O, OO, OHC, C(O), C(O)H, C(O)OH, OC(O)O, C(O)NH$_2$, C(O)NC(O), C(NH)NH$_2$, CN, CNH, C(O)N, OCN, NHC(O)O, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C_{1-6}$ alkylO, $C_{2-6}$ alkenylO, $C_{2-6}$ alkynylO, $OHC_{1-6}$ alkyl, $OHC_{2-6}$ alkenyl, $OHC_{2-6}$ alkynyl, OHC(O), $OHC(O)C_{1-6}$ alkyl, $OHC(O)C_{2-6}$ alkenyl, $OHC(O)C_{2-6}$ alkynyl, $OC(O)C_{1-6}$ alkyl, $OC(O)C_{2-6}$ alkenyl, $OC(O)C_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, or $C(O)OC_{2-6}$ alkynyl; $R^1$ and $R^2$ are each independently an optionally substituted 4-7-member aryl or an optionally substituted 4-7-member heteroaryl; $R^3$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, halide, halogen, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, or C(O)OC$_{2-6}$ alkynyl; and m is 0 to 5.

In aspects of this embodiment, a honeybee repellant may be a compound of formula VIIIb:

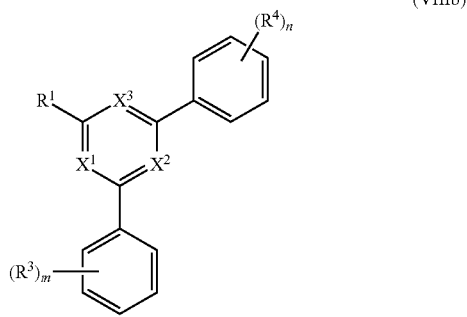

(VIIIb)

wherein: $X^1$, $X^2$, and $X^3$ are each independently C, N, O or S; $R^1$ is an optionally substituted 4-7-member aryl, an optionally substituted 4-7-member heteroaryl, an optionally substituted 4-7-member cycloalkyl, or an optionally substituted 4-7-member heterocycloalkyl; $R^3$ and $R^4$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, or C(O)OC$_{2-6}$ alkynyl; m is 0 to 5; and n is 0 to 5.

In aspects of this embodiment, a honeybee repellant may be a compound of formula VIIIc:

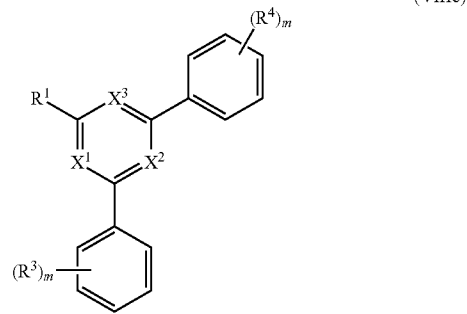

(VIIIc)

wherein: $X^1$, $X^2$, and $X^3$ are each independently C, N, or O; $R^1$ is an optionally substituted 4-7-member aryl or an optionally substituted 4-7-member heteroaryl; $R^3$ and $R^4$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, halide, halogen, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, or C(O)OC$_{2-6}$ alkynyl; m is 0 to 5; and n is 0 to 5.

In aspects of this embodiment, a honeybee repellant may be a compound of formula VIIId:

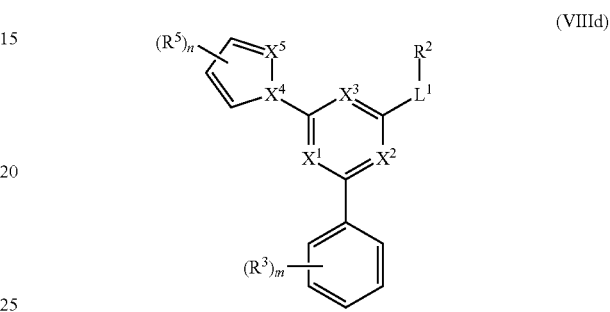

(VIIId)

wherein: $X^1$, $X^2$, $X^3$, $X^4$, and $X^5$ are each independently C, N, O or S; $L^1$ is OH, OOH, O, OO, OHC, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHN, NHNH$_2$, NNN, NN, N(OH), NC, NCH, NHNCH, NCO, (N)C(O), NCS, (N)C(S), N(O)$_2$, N(O)$_3$, NO$_3$, S, SH, S(O), S(O)$_2$, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C$_{1-6}$ alkylO, C$_{2-6}$ alkenylO, C$_{2-6}$ alkynylO, OHC$_{1-6}$ alkyl, OHC$_{2-6}$ alkenyl, OHC$_{2-6}$ alkynyl, OHC(O), OHC(O)C$_{1-6}$ alkyl, OHC(O)C$_{2-6}$ alkenyl, OHC(O)C$_{2-6}$ alkynyl, OC(O)C$_{1-6}$ alkyl, OC(O)C$_{2-6}$ alkenyl, OC(O)C$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, C(O)OC$_{2-6}$ alkynyl, NHNC$_{1-6}$ alkyl, NHNC$_{2-6}$ alkenyl, NHNC$_{2-6}$ alkynyl, CHN, CHNC$_{1-6}$ alkyl, CHNC$_{2-6}$ alkenyl, CHNC$_{2-6}$ alkynyl, CHNNH, CHNNHC$_{1-6}$ alkyl, CHNNHC$_{2-6}$ alkenyl, CHNNHC$_{2-6}$ alkynyl, NC$_{1-6}$ alkyl, NC$_{2-6}$ alkenyl, NC$_{2-6}$ alkynyl, NHC$_{1-6}$ alkyl, NHC$_{2-6}$ alkenyl, NHC$_{2-6}$ alkynyl, NHC(O), NHC(O)C$_{1-6}$ alkyl, NHC(O)C$_{2-6}$ alkenyl, NHC(O)C$_{2-6}$ alkynyl, NC(O)C$_{1-6}$ alkyl, NC(O)C$_{2-6}$ alkenyl, NC(O)C$_{2-6}$ alkynyl, C(O)NHC$_{1-6}$ alkyl, C(O)NHC$_{2-6}$ alkenyl, C(O)NHC$_{2-6}$ alkynyl, C(O)NC$_{1-6}$ alkyl, C(O)NC$_{2-6}$ alkenyl, or C(O)NC$_{2-6}$ alkynyl; $R^2$ is an optionally substituted 4-7-member aryl, an optionally substituted 4-7-member heteroaryl, an optionally substituted 4-7-member cycloalkyl, or an optionally substituted 4-7-member heterocycloalkyl; $R^3$ and $R^5$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), N(O)$_2$, N(O)$_3$, NO$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, or C(O)OC$_{2-6}$ alkynyl; m is 0 to 5; and n is 0 to 5.

In aspects of this embodiment, a honeybee repellant may be a compound of formula VIIIe:

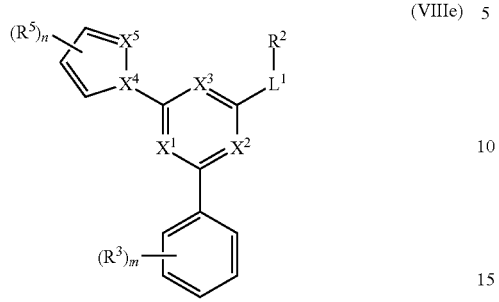

(VIIIe)

wherein: $X^1$, $X^2$, $X^3$, $X^4$, and $X^5$ are each independently C, N, or O; $L^1$ is OH, OOH, O, OO, OHC, C(O), C(O)H, C(O)OH, OC(O)O, C(O)NH$_2$, C(O)NC(O), C(NH)NH$_2$, CN, CNH, C(O)N, OCN, NHC(O)O, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C_{1-6}$ alkylO, $C_{2-6}$ alkenylO, $C_{2-6}$ alkynylO, $OHC_{1-6}$ alkyl, $OHC_{2-6}$ alkenyl, $OHC_{2-6}$ alkynyl, OHC(O), OHC(O)$C_{1-6}$ alkyl, OHC(O)$C_{2-6}$ alkenyl, OHC(O)$C_{2-6}$ alkynyl, OC(O)$C_{1-6}$ alkyl, OC(O)$C_{2-6}$ alkenyl, OC(O)$C_{2-6}$ alkynyl, C(O)$_2C_{1-6}$ alkyl, C(O)$_2C_{2-6}$ alkenyl, C(O)$_2C_{2-6}$ alkynyl, C(O)O$C_{1-6}$ alkyl, C(O)O$C_{2-6}$ alkenyl, or C(O)O$C_{2-6}$ alkynyl; $R^2$ is an optionally substituted 4-7-member aryl or an optionally substituted 4-7-member heteroaryl; $R^3$ and $R^5$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), N(O)$_2$, N(O)$_3$, NO$_3$, halide, halogen, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, C(O)$_2C_{1-6}$ alkyl, C(O)$_2C_{2-6}$ alkenyl, C(O)$_2C_{2-6}$ alkynyl, C(O)O$C_{1-6}$ alkyl, C(O)O$C_{2-6}$ alkenyl, or C(O)O$C_{2-6}$ alkynyl; m is 0 to 5; and n is 0 to 5.

In aspects of this embodiment, a honeybee repellant of formula VIII disclosed herein an optionally substituted 4-(4,6-diphenyl-1,2-dihydro-1,3,5-triazin-2-yl)-2-methoxyphenol or an optionally substituted 4-phenoxy-2-phenyl-6-(1H-pyrazol-1-yl)pyrimidine.

In aspects of this embodiment, a honeybee repellant of formula VIII disclosed herein is

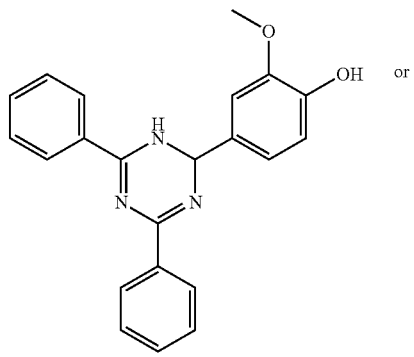

4-(4,6-diphenyl-1,2-dihydro-1,3,5-triazin-2-yl)-2-methoxyphenol

-continued

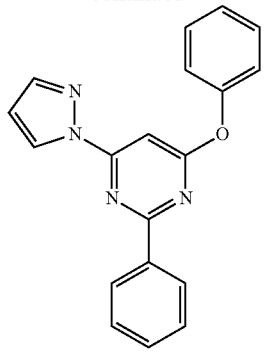

N4-phenoxy-2-phenyl-6-(1H-pyrazol-1-yl)pyrimidine

In aspects of this embodiment, a honeybee repellant is not 4-(4,6-diphenyl-1,2-dihydro-1,3,5-triazin-2-yl)-2-methoxyphenol or 4-phenoxy-2-phenyl-6-(1H-pyrazol-1-yl)pyrimidine.

In another embodiment, a honeybee repellant may be a compound of formula IX:

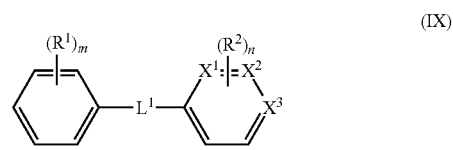

(IX)

wherein: $X^1$, $X^2$, and $X^3$ are each independently C, N, O or S; $L^1$ is OH, OOH, O, OO, OHC, C(O), C(O)H, C(O)OH, OC(O)O, CNH, $CNHC_{1-6}$ alkyl, $CNHC_{2-6}$ alkenyl, $CNHC_{2-6}$ alkynyl, $C_{1-6}$ alkylCNH, $C_{2-6}$ alkenylCNH, $C_{2-6}$ alkynylCNH, CN, $CNC_{1-6}$ alkyl, $CNC_{2-6}$ alkenyl, $CNC_{2-6}$ alkynyl, $C_{1-6}$ alkylCN, $C_{2-6}$ alkenylCN, $C_{2-6}$ alkynylCN, C(O)C=CNH, C(O)C=CNH$C_{1-6}$ alkyl, C(O)C=CNH$C_{1-6}$ alkenyl, C(O)C=CNH$C_{1-6}$ alkynyl, $C_{1-6}$ alkylC(O)C=CNH, $C_{1-6}$ alkenylC(O)C=CNH, $C_{1-6}$ alkynylC(O)C=CNH, C(O)NH$_2$, C(O)NC(O), C(NH)NH$_2$, C(O)N, OCN, NHC(O)O, CS, C(S)H, OC(S)N, SCN, CNS, (N)C(S), NH, NH$_2$, NHN, NHNH$_2$, NNN, NN, N(OH), NC, NCH, NHNCH, NCO, (N)C(O), NCS, (N)C(S), NO, N(O)$_2$, S, SH, S(O), S(O)$_2$, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C_{1-6}$ alkylO, $C_{2-6}$ alkenylO, $C_{2-6}$ alkynylO, $OHC_{1-6}$ alkyl, $OHC_{2-6}$ alkenyl, $OHC_{2-6}$ alkynyl, OHC(O), OHC(O)$C_{1-6}$ alkyl, OHC(O)$C_{2-6}$ alkenyl, OHC(O)$C_{2-6}$ alkynyl, OC(O)$C_{1-6}$ alkyl, OC(O)$C_{2-6}$ alkenyl, OC(O)$C_{2-6}$ alkynyl, C(O)$_2C_{1-6}$ alkyl, C(O)$_2C_{2-6}$ alkenyl, C(O)$_2C_{2-6}$ alkynyl, C(O)O$C_{1-6}$ alkyl, C(O)O$C_{2-6}$ alkenyl, C(O)O$C_{2-6}$ alkynyl, NHN$C_{1-6}$ alkyl, NHN$C_{2-6}$ alkenyl, NHN$C_{2-6}$ alkynyl, CHN, CHN$C_{1-6}$ alkyl, CHN$C_{2-6}$ alkenyl, CHN$C_{2-6}$ alkynyl, CHNNH, CHNNH$C_{1-6}$ alkyl, CHNNH$C_{2-6}$ alkenyl, CHNNH$C_{2-6}$ alkynyl, N$C_{1-6}$ alkyl, N$C_{2-6}$ alkenyl, N$C_{2-6}$ alkynyl, NH$C_{1-6}$ alkyl, NH$C_{2-6}$ alkenyl, NH$C_{2-6}$ alkynyl, NHC(O), NHC(O)$C_{1-6}$ alkyl, NHC(O)$C_{2-6}$ alkenyl, NHC(O)$C_{2-6}$ alkynyl, NC(O)$C_{1-6}$ alkyl, NC(O)$C_{2-6}$ alkenyl, NC(O)$C_{2-6}$ alkynyl, C(O)NH$C_{1-6}$ alkyl, C(O)NH$C_{2-6}$ alkenyl, C(O)NH$C_{2-6}$ alkynyl, C(O)N$C_{1-6}$ alkyl, C(O)N$C_{2-6}$ alkenyl, or C(O)N$C_{2-6}$ alkynyl; $R^1$ and $R^2$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, or C(O)OC$_{2-6}$ alkynyl; m is 0 to 5; and n is 0 to 5.

In aspects of this embodiment, a honeybee repellant may be a compound of formula IXa:

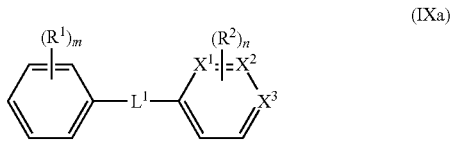

(IXa)

wherein: X$^1$, X$^2$, and X$^3$ are each independently C, N, or O; L$^1$ is OH, OOH, O, OO, OHC, C(O), C(O)H, C(O)OH, OC(O)O, CNH, CNHC$_{1-6}$ alkyl, CNHC$_{2-6}$ alkenyl, CNHC$_{2-6}$ alkynyl, C$_{1-6}$ alkylCNH, C$_{2-6}$ alkenylCNH, C$_{2-6}$ alkynylCNH, CN, CNC$_{1-6}$ alkyl, CNC$_{2-6}$ alkenyl, CNC$_{2-6}$ alkynyl, C$_{1-6}$ alkylCN, C$_{2-6}$ alkenylCN, C$_{2-6}$ alkynylCN, C(O)C=CNH, C(O)C=CNHC$_{1-6}$ alkyl, C(O)C=CNHC$_{1-6}$ alkenyl, C(O)C=CNHC$_{1-6}$ alkynyl, C$_{1-6}$ alkylC(O)C=CNH, C$_{1-6}$ alkenylC(O)C=CNH, C$_{1-6}$ alkynylC(O)C=CNH, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHN, NHNH$_2$, NNN, NN, N(OH), NC, NCH, NHNCH, NCO, (N)C(O), NCS, (N)C(S), NO, or N(O)$_2$; R$^1$ and R$^2$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, halide, halogen, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, or C(O)OC$_{2-6}$ alkynyl; m is 0 to 5; and n is 0 to 5.

In aspects of this embodiment, a honeybee repellant may be a compound of formula IXb:

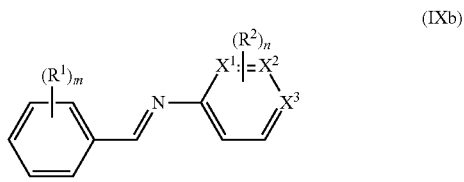

(IXb)

wherein: X$^1$, X$^2$, and X$^3$ are each independently C, N, O or S; R$^1$ and R$^2$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, or C(O)OC$_{2-6}$ alkynyl; m is 0 to 5; and n is 0 to 5.

In aspects of this embodiment, a honeybee repellant may be a compound of formula IXc:

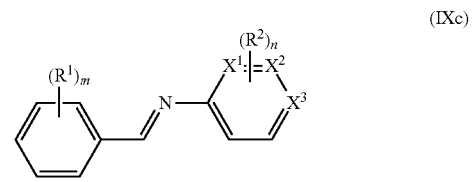

(IXc)

wherein: X$^1$, X$^2$, and X$^3$ are each independently C, N, or O; R$^1$ and R$^2$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S) H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, halide, halogen, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, or C(O)OC$_{2-6}$ alkynyl; m is 0 to 5; and n is 0 to 5.

In aspects of this embodiment, a honeybee repellant may be a compound of formula IXd:

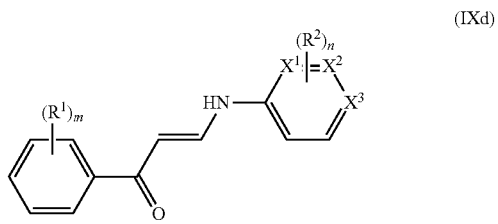

(IXd)

wherein: X$^1$, X$^2$, and X$^3$ are each independently C, N, O or S; R$^1$ and R$^2$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S) H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, or C(O)OC$_{2-6}$ alkynyl; m is 0 to 5; and n is 0 to 5.

In aspects of this embodiment, a honeybee repellant may be a compound of formula IXe:

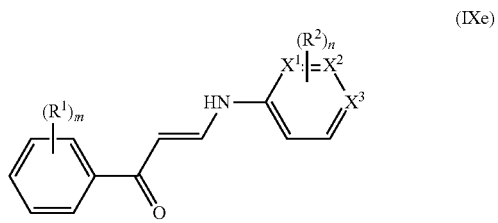

(IXe)

wherein: $X^1$, $X^2$, and $X^3$ are each independently C, N, or O; $R^1$ and $R^2$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S) H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, halide, halogen, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, or C(O)OC$_{2-6}$ alkynyl; m is 0 to 5; and n is 0 to 5.

In aspects of this embodiment, a honeybee repellant may be a compound of formula IXf:

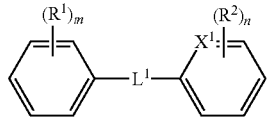

(IXf)

wherein: $X^1$ is C, N, O or S; $L^1$ is OH, OOH, O, OO, OHC, C(O), C(O)H, C(O)OH, OC(O)O, CNH, CNHC$_{1-6}$ alkyl, CNHC$_{2-6}$ alkenyl, CNHC$_{2-6}$ alkynyl, C$_{1-6}$ alkylCNH, C$_{2-6}$ alkenylCNH, C$_{2-6}$ alkynylCNH, CN, CNC$_{1-6}$ alkyl, CNC$_{2-6}$ alkenyl, CNC$_{2-6}$ alkynyl, C$_{1-6}$ alkylCN, C$_{2-6}$ alkenylCN, C$_{2-6}$ alkynylCN, C(O)C=CNH, C(O)C=CNHC$_{1-6}$ alkyl, C(O)C=CNHC$_{1-6}$ alkenyl, C(O)C=CNHC$_{1-6}$ alkynyl, C$_{1-6}$ alkylC(O)C=CNH, C$_{1-6}$ alkenylC(O)C=CNH, C$_{1-6}$ alkynylC(O)C=CNH, C(O)NH$_2$, C(O)NC(O), C(NH)NH$_2$, C(O)N, OCN, NHC(O)O, CS, C(S)H, OC(S)N, SCN, CNS, (N)C(S), NH, NH$_2$, NHN, NHNH$_2$, NNN, NN, N(OH), NC, NCH, NHNCH, NCO, (N)C(O), NCS, (N)C(S), NO, N(O)$_2$, S, SH, S(O), S(O)$_2$, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C$_{1-6}$ alkylO, C$_{2-6}$ alkenylO, C$_{2-6}$ alkynylO, OHC$_{1-6}$ alkyl, OHC$_{2-6}$ alkenyl, OHC$_{2-6}$ alkynyl, OHC(O), OHC(O)C$_{1-6}$ alkyl, OHC(O)C$_{2-6}$ alkenyl, OHC(O)C$_{2-6}$ alkynyl, OC(O)C$_{1-6}$ alkyl, OC(O)C$_{2-6}$ alkenyl, OC(O)C$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, C(O)OC$_{2-6}$ alkynyl, NHNC$_{1-6}$ alkyl, NHNC$_{2-6}$ alkenyl, NHNC$_{2-6}$ alkynyl, CHN, CHNC$_{1-6}$ alkyl, CHNC$_{2-6}$ alkenyl, CHNC$_{2-6}$ alkynyl, CHNNH, CHNNHC$_{1-6}$ alkyl, CHNNHC$_{2-6}$ alkenyl, CHNNHC$_{2-6}$ alkynyl, NC$_{1-6}$ alkyl, NC$_{2-6}$ alkenyl, NC$_{2-6}$ alkynyl, NHC$_{1-6}$ alkyl, NHC$_{2-6}$ alkenyl, NHC$_{2-6}$ alkynyl, NHC(O), NHC(O)C$_{1-6}$ alkyl, NHC(O)C$_{2-6}$ alkenyl, NHC(O)C$_{2-6}$ alkynyl, NC(O)C$_{1-6}$ alkyl, NC(O)C$_{2-6}$ alkenyl, NC(O)C$_{2-6}$ alkynyl, C(O)NHC$_{1-6}$ alkyl, C(O)NHC$_{2-6}$ alkenyl, C(O)NHC$_{2-6}$ alkynyl, C(O)NC$_{1-6}$ alkyl, C(O)NC$_{2-6}$ alkenyl, or C(O)NC$_{2-6}$ alkynyl; $R^1$ and $R^2$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, or C(O)OC$_{2-6}$ alkynyl; m is 0 to 5; and n is 0 to 5.

In aspects of this embodiment, a honeybee repellant may be a compound of formula IXg:

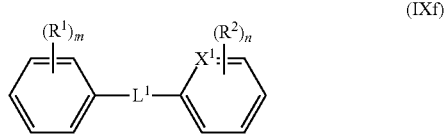

(IXg)

wherein: $X^1$ is C, N, or O; $L^1$ is OH, OOH, O, OO, OHC, C(O), C(O)H, C(O)OH, OC(O)O, CNH, CNHC$_{1-6}$ alkyl, CNHC$_{2-6}$ alkenyl, CNHC$_{2-6}$ alkynyl, C$_{1-6}$ alkylCNH, C$_{2-6}$ alkenylCNH, C$_{2-6}$ alkynylCNH, CN, CNC$_{1-6}$ alkyl, CNC$_{2-6}$ alkenyl, CNC$_{2-6}$ alkynyl, C$_{1-6}$ alkylCN, C$_{2-6}$ alkenylCN, C$_{2-6}$ alkynylCN, C(O)C=CNH, C(O)C=CNHC$_{1-6}$ alkyl, C(O)C=CNHC$_{1-6}$ alkenyl, C(O)C=CNHC$_{1-6}$ alkynyl, C$_{1-6}$ alkylC(O)C=CNH, C$_{1-6}$ alkenylC(O)C=CNH, C$_{1-6}$ alkynylC(O)C=CNH, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHN, NHNH$_2$, NNN, NN, N(OH), NC, NCH, NHNCH, NCO, (N)C(O), NCS, (N)C(S), NO, N(O)$_2$; $R^1$ and $R^2$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, halide, halogen, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, or C(O)OC$_{2-6}$ alkynyl; m is 0 to 5; and n is 0 to 5.

In aspects of this embodiment, a honeybee repellant of formula IX disclosed herein an optionally substituted 2-bromo-4-chloro-6-[(2-pyridinylimino)methyl]phenol or an optionally substituted 1-(4-bromophenyl)-3-[(2-hydroxyphenyl)amino]-2-propen-1-one.

In aspects of this embodiment, a honeybee repellant of formula IX disclosed herein is

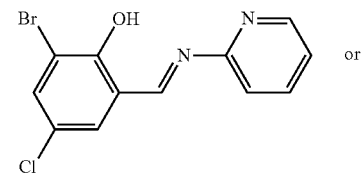

2-bromo-4-chloro-6-[(2-pyridinylimino)
methyl]phenol or

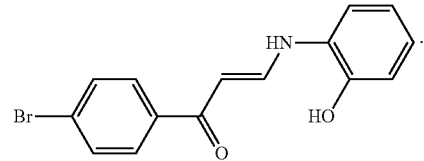

1-(4-bromophenyl)-3-[(2-hydroxyphenyl)amino]-2-
propen-1-one

In aspects of this embodiment, a honeybee repellant is not 2-bromo-4-chloro-6-[(2-pyridinylimino)methyl]phenol or 1-(4-bromophenyl)-3-[(2-hydroxyphenyl)amino]-2-propen-1-one.

In another embodiment, a honeybee repellant may be a compound of formula X:

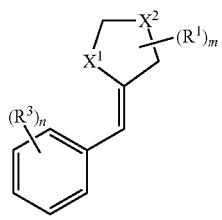

(X)

wherein: $X^1$ and $X^2$ are each independently C, N, O or S; $R^1$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, or C(O)OC$_{2-6}$ alkynyl; $R^3$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, C(O)OC$_{2-6}$ alkynyl, an optionally substituted 4-7-member aryl, an optionally substituted 4-7-member heteroaryl, an optionally substituted 4-7-member cycloalkyl, or an optionally substituted 4-7-member heterocycloalkyl; m is 0 to 4; and n is 0 to 5.

In aspects of this embodiment, a honeybee repellant may be a compound of formula Xa

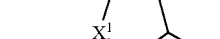

(Xa)

wherein: $X^1$ and $X^2$ are each independently N, O or S; $R^1$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, N(OH), NC, NCO, (N)C(O), NCS, (N)C(S), NO, N(O)$_2$, N(O)$_3$, SH, S(O), S(O)$_2$, S(O)$_3$, S(O)$_2$N, halide, halogen, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl; $R^3$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, N(OH), NC, NCO, (N)C(O), NCS, (N)C(S), NO, N(O)$_2$, N(O)$_3$, SH, S(O), S(O)$_2$, S(O)$_3$, S(O)$_2$N, halide, halogen, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, C(O)OC$_{2-6}$ alkynyl, an optionally substituted 4-7-member cycloalkyl, or an optionally substituted 4-7-member heterocycloalkyl; m is 0 to 4; and n is 0 to 5.

In aspects of this embodiment, a honeybee repellant may be a compound of formula Xb (Xb)

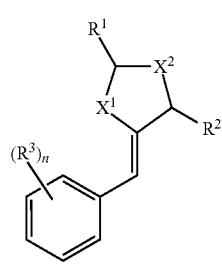

wherein: $X^1$ and $X^2$ are each independently C, N, O or S; $R^1$ and $R^2$ are each independently H, OH, OOH, O, OO, C(O), C(O)H, C(O)OH, OC(O)O, C(O)NH$_2$, C(O)NC(O), C(NH) NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, or C(O)OC$_{2-6}$ alkynyl; $R^3$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, C(O)OC$_{2-6}$ alkynyl, an optionally substituted 4-7-member aryl, an optionally substituted 4-7-member heteroaryl, an optionally substituted 4-7-member cycloalkyl, or an optionally substituted 4-7-member heterocycloalkyl; and n is 0 to 5.

In aspects of this embodiment, a honeybee repellant may be a compound of formula Xc (Xc)

wherein: $X^1$ and $X^2$ are each independently N, O or S; $R^1$ and $R^2$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, N(OH), NC, NCO, (N)C(O), NCS, (N)C(S), NO, N(O)$_2$, N(O)$_3$, SH, S(O), S(O)$_2$, S(O)$_3$, S(O)$_2$N, halide, halogen, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl; $R^3$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, halide, halogen, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, C(O)OC$_{2-6}$ alkynyl, an optionally substituted 4-7-member cycloalkyl, or an optionally substituted 4-7-member heterocycloalkyl; and n is 0 to 5.

In aspects of this embodiment, a honeybee repellant may be a compound of formula Xd

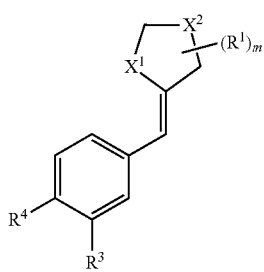

(Xd)

wherein: $X^1$ and $X^2$ are each independently C, N, O or S; $R^1$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, or C(O)OC$_{2-6}$ alkynyl; $R^3$ and $R^4$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, C(O)OC$_{2-6}$ alkynyl, an optionally substituted 4-7-member aryl, an optionally substituted 4-7-member heteroaryl, an optionally substituted 4-7-member cycloalkyl, or an optionally substituted 4-7-member heterocycloalkyl; and m is 0 to 4.

In aspects of this embodiment, a honeybee repellant may be a compound of formula Xe

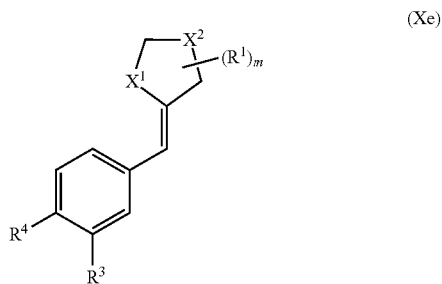

(Xe)

wherein: $X^1$ and $X^2$ are each independently N, O or S; $R^1$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, N(OH), NC, NCO, (N)C(O), NCS, (N)C(S), NO, N(O)$_2$, N(O)$_3$, SH, S(O), S(O)$_2$, S(O)$_3$, S(O)$_2$N, halide, halogen, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl; $R^3$ and $R^4$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, halide, halogen, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, C(O)OC$_{2-6}$ alkynyl, an optionally substituted 4-7-member cycloalkyl, or an optionally substituted 4-7-member heterocycloalkyl; and m is 0 to 4.

In aspects of this embodiment, a honeybee repellant may be a compound of formula Xf

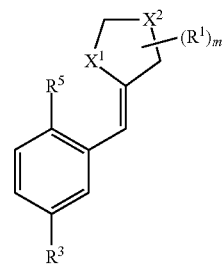

(Xf)

wherein: $X^1$ and $X^2$ are each independently C, N, O or S; $R^1$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, or C(O)OC$_{2-6}$ alkynyl; $R^3$ and $R^5$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, $N(O)_2$, $N(O)_3$, SH, S(O), $S(O)_2$, $S(O)_3$, $S(O)_2N$, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, $C(O)OC_{2-6}$ alkynyl, an optionally substituted 4-7-member aryl, an optionally substituted 4-7-member heteroaryl, an optionally substituted 4-7-member cycloalkyl, or an optionally substituted 4-7-member heterocycloalkyl; and m is 0 to 4.

In aspects of this embodiment, a honeybee repellant may be a compound of formula Xg

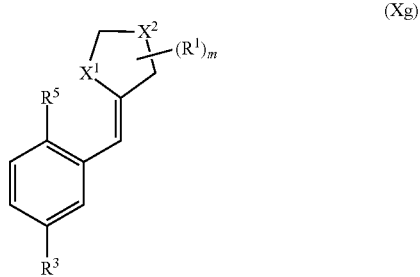

(Xg)

wherein: $X^1$ and $X^2$ are each independently N, O or S; $R^1$ is independently H, OH, OOH, O, OO, C(O), C(O)H, C(O)OH, OC(O)O, $C(O)NH_2$, C(O)NC(O), $C(NH)NH_2$, CN, CNH, C(O)N, OCN, NHC(O)O, CS, C(S)H, OC(S)N, SCN, CNS, (N)C(S), NH, $NH_2$, $NHNH_2$, N(OH), NC, NCO, (N)C(O), NCS, (N)C(S), NO, $N(O)_2$, $N(O)_3$, SH, S(O), $S(O)_2$, $S(O)_3$, $S(O)_2N$, halide, halogen, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl; $R^3$ and $R^5$ are each independently H, OH, OOH, O, OO, C(O), C(O)H, C(O)OH, OC(O)O, $C(O)NH_2$, C(O)NC(O), $C(NH)NH_2$, CN, CNH, C(O)N, OCN, NHC(O)O, CS, C(S)H, OC(S)N, SCN, CNS, (N)C(S), NH, $NH_2$, $NHNH_2$, NNN, NN, N(OH), NC, NCO, (N)C(O), NCS, (N)C(S), NO, $N(O)_2$, $N(O)_3$, SH, S(O), $S(O)_2$, $S(O)_3$, $S(O)_2N$, halide, halogen, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, $C(O)OC_{2-6}$ alkynyl, an optionally substituted 4-7-member cycloalkyl, or an optionally substituted 4-7-member heterocycloalkyl; and m is 0 to 4.

In aspects of this embodiment, a honeybee repellant may be a compound of formula Xh

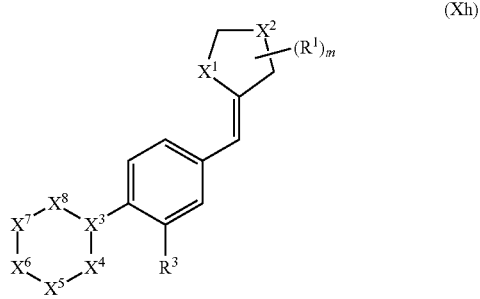

(Xh)

wherein: $X^1$ and $X^2$ are each independently C, N, O or S; $X^3$, $X^4$, $X^5$, $X^6$, $X^7$ and $X^8$ are each independently C, N, O or S; $R^1$ is independently H, OH, OOH, O, OO, C(O), C(O)H, C(O)OH, OC(O)O, $C(O)NH_2$, C(O)NC(O), $C(NH)NH_2$, CN, CNH, C(O)N, OCN, NHC(O)O, CS, C(S)H, OC(S)N, SCN, CNS, (N)C(S), NH, $NH_2$, $NHNH_2$, NNN, NN, N(OH), NC, NCO, (N)C(O), NCS, (N)C(S), NO, $N(O)_2$, $N(O)_3$, SH, S(O), $S(O)_2$, $S(O)_3$, $S(O)_2N$, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, or $C(O)OC_{2-6}$ alkynyl; $R^3$ is H, OH, OOH, O, OO, C(O), C(O)H, C(O)OH, OC(O)O, $C(O)NH_2$, C(O)NC(O), $C(NH)NH_2$, CN, CNH, C(O)N, OCN, NHC(O)O, CS, C(S)H, OC(S)N, SCN, CNS, (N)C(S), NH, $NH_2$, $NHNH_2$, NNN, NN, N(OH), NC, NCO, (N)C(O), NCS, (N)C(S), NO, $N(O)_2$, $N(O)_3$, SH, S(O), $S(O)_2$, $S(O)_3$, $S(O)_2N$, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, or $C(O)OC_{2-6}$ alkynyl; and m is 0 to 4.

In aspects of this embodiment, a honeybee repellant may be a compound of formula Xi

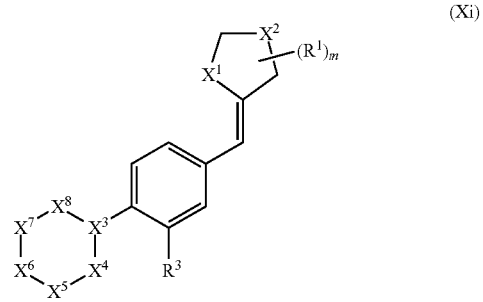

(Xi)

wherein: $X^1$ and $X^2$ are each independently N, O or S; $X^3$, $X^4$, $X^5$, $X^6$, $X^7$ and $X^8$ are each independently C, N, or O; $R^1$ is independently H, OH, OOH, O, OO, C(O), C(O)H, C(O)OH, OC(O)O, $C(O)NH_2$, C(O)NC(O), $C(NH)NH_2$, CN, CNH, C(O)N, OCN, NHC(O)O, CS, C(S)H, OC(S)N, SCN, CNS, (N)C(S), NH, $NH_2$, $NHNH_2$, N(OH), NC, NCO, (N)C(O), NCS, (N)C(S), NO, $N(O)_2$, $N(O)_3$, SH, S(O), $S(O)_2$, $S(O)_3$, $S(O)_2N$, halide, halogen, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl; $R^3$ is H, OH, OOH, O, OO, C(O), C(O)H, C(O)OH, OC(O)O, $C(O)NH_2$, C(O)NC(O), $C(NH)NH_2$, CN, CNH, C(O)N, OCN, NHC(O)O, CS, C(S)H, OC(S)N, SCN, CNS, (N)C(S), NH, $NH_2$, $NHNH_2$, NNN, NN, N(OH), NC, NCO, (N)C(O), NCS, (N)C(S), NO, $N(O)_2$, $N(O)_3$, SH, S(O), $S(O)_2$, $S(O)_3$, $S(O)_2N$, halide, halogen, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, or $C(O)OC_{2-6}$ alkynyl; and m is 0 to 4.

In aspects of this embodiment, a honeybee repellant of formula X disclosed herein an optionally substituted 5-[4-(4-morpholinyl)-3-nitrobenzylidene]-2-thioxo-1,3-thiazolidin-4-one or an optionally substituted 5-(5-bromo-2-methoxybenzylidene)-3-ethyl-2-thioxo-1,3-thiazolidin-4-one.

In aspects of this embodiment, a honeybee repellant of formula X disclosed herein is

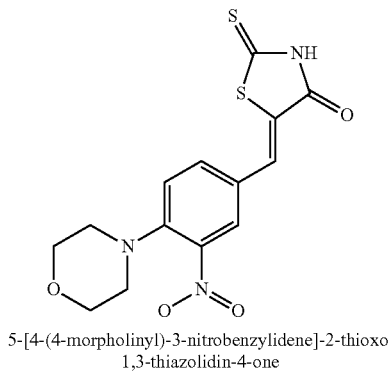

5-[4-(4-morpholinyl)-3-nitrobenzylidene]-2-thioxo-1,3-thiazolidin-4-one or

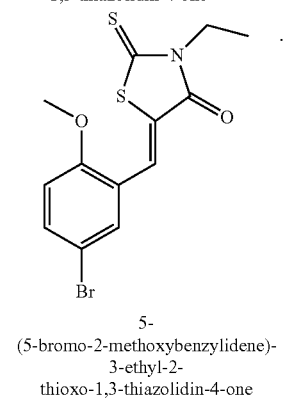

5-(5-bromo-2-methoxybenzylidene)-3-ethyl-2-thioxo-1,3-thiazolidin-4-one

In aspects of this embodiment, a honeybee repellant is not 5-[4-(4-morpholinyl)-3-nitrobenzylidene], -2-thioxo-1,3-thiazolidin-4-one or 5-(5-bromo-2-methoxybenzylidene)-3-ethyl-2-thioxo-1,3-thiazolidin-4-one.

In another embodiment, a honeybee repellant may be a compound of formula XI:

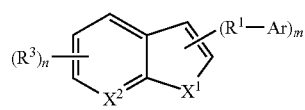

(XI)

wherein: $X^1$ and $X^2$ are each independently C, N, O or S; $R^1$ is independently NH, $NH_2$, $NHNH_2$, NNN, NN, N(OH), NC, NCO, (N)C(O), NHC(O), NHC(O)$C_{1-6}$ alkyl, NHC(O)$C_{2-6}$ alkenyl, NHC(O)$C_{2-6}$ alkynyl, $C_{1-6}$ alkylNHC(O), $C_{2-6}$ alkenylNHC(O), $C_{2-6}$ alkynylNHC(O), NC(O), NHC(O)$C_{1-6}$ alkyl, NC(O)$C_{2-6}$ alkenyl, NC(O)$C_{2-6}$ alkynyl, $C_{1-6}$ alkylNC(O), $C_{2-6}$ alkenylNC(O), $C_{2-6}$ alkynylNC(O), CNHC(O), CNHC(O)$C_{1-6}$ alkyl, CNHC(O)$C_{2-6}$ alkenyl, CNHC(O)$C_{2-6}$ alkynyl, $C_{1-6}$ alkylCNHC(O), $C_{2-6}$ alkenylCNHC(O), $C_{2-6}$ alkynylCNHC(O), CNC(O), CNC(O)$C_{1-6}$ alkyl, CNC(O)$C_{2-6}$ alkenyl, CNC(O)$C_{2-6}$ alkynyl, $C_{1-6}$ alkylCNC(O), $C_{2-6}$ alkenylCNC(O), $C_{2-6}$ alkynylCNC(O), CNNHC(O), CNNHC(O)$C_{1-6}$ alkyl, CNNHC(O)$C_{2-6}$ alkenyl, CNNHC(O)$C_{2-6}$ alkynyl, $C_{1-6}$ alkylCNNHC(O), $C_{2-6}$ alkenylCNNHC(O), $C_{2-6}$ alkynylCNNHC(O), CNNC(O), CNNC(O)$C_{1-6}$ alkyl, CNNC(O)$C_{2-6}$ alkenyl, CNNC(O)$C_{2-6}$ alkynyl, $C_{1-6}$ alkylCNNC(O), $C_{2-6}$ alkenylCNNC(O), $C_{2-6}$ alkynylCNNC(O), C(O), C(O)$_2$, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, C(O)$C_{1-6}$ alkyl, C(O)$C_{2-6}$ alkenyl, C(O)$C_{2-6}$ alkynyl, $C_{1-6}$ alkylC(O), $C_{2-6}$ alkenylC(O), $C_{2-6}$ alkynylC(O), C(O)$_2C_{1-6}$ alkyl, C(O)$_2C_{2-6}$ alkenyl, C(O)$_2C_{2-6}$ alkynyl, $C_{1-6}$ alkylC(O)$_2$, $C_{2-6}$ alkenylC(O)$_2$, $C_{2-6}$ alkynylC(O)$_2$, C(O)OC$_{1-6}$ alkyl, C(O)OC$_{2-6}$ alkenyl, C(O)OC$_{2-6}$ alkynyl, $C_{1-6}$ alkylC(O)O, $C_{2-6}$ alkenylC(O)O, $C_{2-6}$ alkynylC(O)O, $CH_2C(O)C_{1-6}$ alkyl, $CH_2C(O)C_{2-6}$ alkenyl, $CH_2C(O)C_{2-6}$ alkynyl, $C_{1-6}$ alkylCH$_2$C(O), $C_{2-6}$ alkenylCH$_2$C(O), or $C_{2-6}$ alkynylCH$_2$C(O), CHC(O)$C_{1-6}$ alkyl, CHC(O)$C_{2-6}$ alkenyl, CHC(O)$C_{2-6}$ alkynyl, $C_{1-6}$ alkylCHC(O), $C_{2-6}$ alkenylCHC(O), or $C_{2-6}$ alkynylCHC(O); Ar is independently optionally substituted 4-7-member aryl, an optionally substituted 4-7-member heteroaryl, an optionally substituted 4-7-member cycloalkyl, or an optionally substituted 4-7-member heterocycloalkyl; $R^3$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, C(O)$_2C_{1-6}$ alkyl, C(O)$_2C_{2-6}$ alkenyl, C(O)$_2C_{2-6}$ alkynyl, C(O)OC$_{1-6}$ alkyl, C(O)OC$_{2-6}$ alkenyl, C(O)OC$_{2-6}$ alkynyl, an optionally substituted 4-7-member aryl, an optionally substituted 4-7-member heteroaryl, an optionally substituted 4-7-member cycloalkyl, or an optionally substituted 4-7-member heterocycloalkyl; m is 0 to 3; and n is 0 to 4.

In aspects of this embodiment, a honeybee repellant may be a compound of formula XIa:

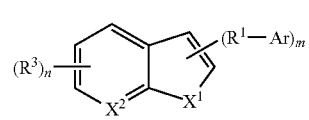

(XIa)

wherein: $X^1$ and $X^2$ are each independently C, N, or S; $R^1$ is independently NH, NH$_2$, NHNH$_2$, N(OH), NCO, (N)C(O), NHC(O), NHC(O)$C_{1-6}$ alkyl, $C_{1-6}$ alkylNHC(O), NC(O), NHC(O)$C_{1-6}$ alkyl, $C_{1-6}$ alkylNC(O), CNHC(O), CNHC(O)$C_{1-6}$ alkyl, $C_{1-6}$ alkylCNHC(O), CNC(O), CNC(O)$C_{1-6}$ alkyl, $C_{1-6}$ alkylCNC(O), CNNHC(O), CNNHC(O)$C_{1-6}$ alkyl, $C_{1-6}$ alkylCNNHC(O), CNNC(O), CNNC(O)$C_{1-6}$ alkyl, $C_{1-6}$ alkylCNNC(O), C(O), C(O)$_2$, $C_{1-6}$ alkyl, $OC_{1-6}$ alkyl, C(O)$C_{1-6}$ alkyl, $C_{1-6}$ alkylC(O), C(O)$_2C_{1-6}$ alkyl, or $C_{1-6}$ alkylC(O)$_2$, or C(O)OC$_{1-6}$ alkyl; Ar is independently optionally substituted 4-7-member aryl or an optionally substituted 4-7-member heteroaryl; $R^3$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, NH, NH$_2$, NHNH$_2$, NNN, NN, N(OH), NC, NCO, (N)C(O), NCS, (N)C(S), NO, N(O)$_2$, N(O)$_3$, halide, halogen, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, C(O)$_2C_{1-6}$ alkyl, C(O)$_2C_{2-6}$ alkenyl, C(O)$_2C_{2-6}$ alkynyl, C(O)OC$_{1-6}$ alkyl, C(O)OC$_{2-6}$ alkenyl, C(O)OC$_{2-6}$ alkynyl, an optionally substituted 4-7-member aryl, an optionally substituted 4-7-member heteroaryl, an optionally substituted 4-7-member cycloalkyl, or an optionally substituted 4-7-member heterocycloalkyl; m is 0 to 3; and n is 0 to 4.

In aspects of this embodiment, a honeybee repellant may be a compound of formula XIb:

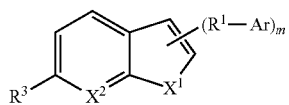

(XIb)

wherein: $X^1$ and $X^2$ are each independently C, N, O or S; $R^1$ is independently NH, $NH_2$, $NHNH_2$, NNN, NN, N(OH), NC, NCO, (N)C(O), NHC(O), NHC(O)$C_{1-6}$ alkyl, NHC(O) $C_{2-6}$ alkenyl, NHC(O)$C_{2-6}$ alkynyl, $C_{1-6}$ alkylNHC(O), $C_{2-6}$ alkenylNHC(O), $C_{2-6}$ alkynylNHC(O), NC(O), NHC(O) $C_{1-6}$ alkyl, NC(O)$C_{2-6}$ alkenyl, NC(O)$C_{2-6}$ alkynyl, $C_{1-6}$ alkylNC(O), $C_{2-6}$ alkenylNC(O), $C_{2-6}$ alkynylNC(O), CNHC(O), CNHC(O)$C_{1-6}$ alkyl, CNHC(O)$C_{2-6}$ alkenyl, CNHC(O)$C_{2-6}$ alkynyl, $C_{1-6}$ alkylCNHC(O), $C_{2-6}$ alkenyl-CNHC(O), $C_{2-6}$ alkynylCNHC(O), CNC(O), CNC(O)$C_{1-6}$ alkyl, CNC(O)$C_{2-6}$ alkenyl, CNC(O)$C_{2-6}$ alkynyl, $C_{1-6}$ alkylCNC(O), $C_{2-6}$ alkenylCNC(O), $C_{2-6}$ alkynylCNC(O), CNNHC(O), CNNHC(O)$C_{1-6}$ alkyl, CNNHC(O)$C_{2-6}$ alkenyl, CNNHC(O)$C_{2-6}$ alkynyl, $C_{1-6}$ alkylCNNHC(O), $C_{2-6}$ alkenylCNNHC(O), $C_{2-6}$ alkynylCNNHC(O), CNNC(O), CNNC(O)$C_{1-6}$ alkyl, CNNC(O)$C_{2-6}$ alkenyl, CNNC(O)$C_{2-6}$ alkynyl, $C_{1-6}$ alkylCNNC(O), $C_{2-6}$ alkenylCNNC(O), $C_{2-6}$ alkynylCNNC(O), C(O), C(O)$_2$, $C_{1-6}$ alkyl, $C_{2-6}$ alkenyl, $C_{2-6}$ alkynyl, O$C_{1-6}$ alkyl, O$C_{2-6}$ alkenyl, O$C_{2-6}$ alkynyl, C(O)$C_{1-6}$ alkyl, C(O)$C_{2-6}$ alkenyl, C(O)$C_{2-6}$ alkynyl, $C_{1-6}$ alkylC(O), $C_{2-6}$ alkenylC(O), $C_{2-6}$ alkynylC(O), C(O)$_2$$C_{1-6}$ alkyl, C(O)$_2$$C_{2-6}$ alkenyl, C(O)$_2$$C_{2-6}$ alkynyl, $C_{1-6}$ alkylC(O)$_2$, $C_{2-6}$ alkenylC(O)$_2$, $C_{2-6}$ alkynylC(O)$_2$, C(O) O$C_{1-6}$ alkyl, C(O)O$C_{2-6}$ alkenyl, C(O)O$C_{2-6}$ alkynyl, $C_{1-6}$ alkylC(O)O, $C_{2-6}$ alkenylC(O)O, $C_{2-6}$ alkynylC(O)O, $CH_2$C(O)$C_{1-6}$ alkyl, $CH_2$C(O)$C_{2-6}$ alkenyl, $CH_2$C(O)$C_{2-6}$ alkynyl, $C_{1-6}$ alkyl$CH_2$C(O), $C_{2-6}$ alkenyl$CH_2$C(O), or $C_{2-6}$ alkynyl$CH_2$C(O), CHC(O)$C_{1-6}$ alkyl, CHC(O)$C_{2-6}$ alkenyl, CHC(O)$C_{2-6}$ alkynyl, $C_{1-6}$ alkylCHC(O), $C_{2-6}$ alkenylCHC (O), or $C_{2-6}$ alkynylCHC(O); Ar is independently optionally substituted 4-7-member aryl, an optionally substituted 4-7-member heteroaryl, an optionally substituted 4-7-member cycloalkyl, or an optionally substituted 4-7-member heterocycloalkyl; $R^3$ is H, OH, OOH, O, OO, C(O), C(O)H, C(O)OH, OC(O)O, C(O)$NH_2$, C(O)NC(O), C(NH)$NH_2$, CN, CNH, C(O)N, OCN, NHC(O)O, CS, C(S)H, OC(S)N, SCN, CNS, (N)C(S), NH, $NH_2$, $NHNH_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, $C_{1-6}$ alkyl, $C_{2-6}$ alkenyl, $C_{2-6}$ alkynyl, O$C_{1-6}$ alkyl, O$C_{2-6}$ alkenyl, O$C_{2-6}$ alkynyl, C(O)$_2$$C_{1-6}$ alkyl, C(O)$_2$$C_{2-6}$ alkenyl, C(O)$_2$$C_{2-6}$ alkynyl, C(O)O$C_{1-6}$ alkyl, C(O)O$C_{2-6}$ alkenyl, C(O)O$C_{2-6}$ alkynyl, an optionally substituted 4-7-member aryl, an optionally substituted 4-7-member heteroaryl, an optionally substituted 4-7-member cycloalkyl, or an optionally substituted 4-7-member heterocycloalkyl; and m is 0 to 3.

In aspects of this embodiment t, a honeybee repellant may be a compound of formula XIc:

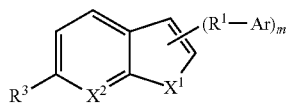

(XIc)

wherein: $X^1$ and $X^2$ are each independently C, N, or S; $R^1$ is independently NH, $NH_2$, $NHNH_2$, N(OH), NCO, (N)C (O), NHC(O), NHC(O)$C_{1-6}$ alkyl, $C_{1-6}$ alkylNHC(O), NC(O), NHC(O)$C_{1-6}$ alkyl, $C_{1-6}$ alkylNC(O), CNHC(O), CNHC(O)$C_{1-6}$ alkyl, $C_{1-6}$ alkylCNHC(O), CNC(O), CNC (O)$C_{1-6}$ alkyl, $C_{1-6}$ alkylCNC(O), CNNHC(O), CNNHC(O) $C_{1-6}$ alkyl, $C_{1-6}$ alkylCNNHC(O), CNNC(O), CNNC(O)$C_{1-6}$ alkyl, $C_{1-6}$ alkylCNNC(O), C(O), C(O)$_2$, $C_{1-6}$ alkyl, O$C_{1-6}$ alkyl, C(O)$C_{1-6}$ alkyl, $C_{1-6}$ alkylC(O), C(O)$_2$$C_{1-6}$ alkyl, $C_{1-6}$ alkylC(O)$_2$, or C(O)O$C_{1-6}$ alkyl; Ar is independently optionally substituted 4-7-member aryl or an optionally substituted 4-7-member heteroaryl; $R^3$ is H, OH, OOH, O, OO, C(O), C(O)H, C(O)OH, OC(O)O, C(O)$NH_2$, C(O)NC(O), C(NH) $NH_2$, CN, CNH, C(O)N, OCN, NHC(O)O, NH, $NH_2$, $NHNH_2$, NNN, NN, N(OH), NC, NCO, (N)C(O), NCS, (N)C(S), NO, N(O)$_2$, N(O)$_3$, halide, halogen, $C_{1-6}$ alkyl, $C_{2-6}$ alkenyl, $C_{2-6}$ alkynyl, O$C_{1-6}$ alkyl, O$C_{2-6}$ alkenyl, O$C_{2-6}$ alkynyl, C(O)$_2$$C_{1-6}$ alkyl, C(O)$_2$$C_{2-6}$ alkenyl, C(O)$_2$$C_{2-6}$ alkynyl, C(O)O$C_{1-6}$ alkyl, C(O)O$C_{2-6}$ alkenyl, C(O)O$C_{2-6}$ alkynyl, an optionally substituted 4-7-member aryl, an optionally substituted 4-7-member heteroaryl, an optionally substituted 4-7-member cycloalkyl, or an optionally substituted 4-7-member heterocycloalkyl; and m is 0 to 3.

In aspects of this embodiment, a honeybee repellant may be a compound of formula XId:

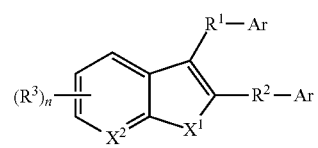

(XId)

wherein: $X^1$ and $X^2$ are each independently C, N, O or S; $R^1$ is N, NH, $NH_2$, $NHNH_2$, NNN, NN, N(OH), NC, NCO, (N)C(O), NHC(O), NHC(O)$C_{1-6}$ alkyl, NHC(O)$C_{2-6}$ alkenyl, NHC(O)$C_{2-6}$ alkynyl, $C_{1-6}$ alkylNHC(O), $C_{2-6}$ alkenyl-NHC(O), $C_{2-6}$ alkynylNHC(O), NC(O), NHC(O)$C_{1-6}$ alkyl, NC(O)$C_{2-6}$ alkenyl, NC(O)$C_{2-6}$ alkynyl, $C_{1-6}$ alkylNC(O), $C_{2-6}$ alkenylNC(O), $C_{2-6}$ alkynylNC(O), CNHC(O), CNHC (O)$C_{1-6}$ alkyl, CNHC(O)$C_{2-6}$ alkenyl, CNHC(O)$C_{2-6}$ alkynyl, $C_{1-6}$ alkylCNHC(O), $C_{2-6}$ alkenylCNHC(O), $C_{2-6}$ alkynylCNHC(O), CNC(O), CNC(O)$C_{1-6}$ alkyl, CNC(O)$C_{2-6}$ alkenyl, CNC(O)$C_{2-6}$ alkynyl, $C_{1-6}$ alkylCNC(O), $C_{2-6}$ alkenylCNC(O), $C_{2-6}$ alkynylCNC(O), CNNHC(O), CNNHC (O)$C_{1-6}$ alkyl, CNNHC(O)$C_{2-6}$ alkenyl, CNNHC(O)$C_{2-6}$ alkynyl, $C_{1-6}$ alkylCNNHC(O), $C_{2-6}$ alkenylCNNHC(O), $C_{2-6}$ alkynylCNNHC(O), CNNC(O), CNNC(O)$C_{1-6}$ alkyl, CNNC(O)$C_{2-6}$ alkenyl, CNNC(O)$C_{2-6}$ alkynyl, $C_{1-6}$ alkyl-CNNC(O), $C_{2-6}$ alkenylCNNC(O), or $C_{2-6}$ alkynylCNNC (O); $R^2$ is C(O), C(O)$_2$, $C_{1-6}$ alkyl, $C_{2-6}$ alkenyl, $C_{2-6}$ alkynyl, O$C_{1-6}$ alkyl, O$C_{2-6}$ alkenyl, O$C_{2-6}$ alkynyl, C(O)$C_{1-6}$ alkyl, C(O)$C_{2-6}$ alkenyl, C(O)$C_{2-6}$ alkynyl, $C_{1-6}$ alkylC(O), $C_{2-6}$ alkenylC(O), $C_{2-6}$ alkynylC(O), C(O)$_2$$C_{1-6}$ alkyl, C(O)$_2$$C_{2-6}$ alkenyl, C(O)$_2$$C_{2-6}$ alkynyl, $C_{1-6}$ alkylC(O)$_2$, $C_{2-6}$ alkenylC(O)$_2$, $C_{2-6}$ alkynylC(O)$_2$, C(O)O$C_{1-6}$ alkyl, C(O) O$C_{2-6}$ alkenyl, C(O)O$C_{2-6}$ alkynyl, $C_{1-6}$ alkylC(O)O, $C_{2-6}$ alkenylC(O)O, $C_{2-6}$ alkynylC(O)O, $CH_2$C(O)$C_{1-6}$ alkyl, $CH_2$C(O)$C_{2-6}$ alkenyl, $CH_2$C(O)$C_{2-6}$ alkynyl, $C_{1-6}$ alkyl$CH_2$C(O), $C_{2-6}$ alkenyl$CH_2$C(O), or $C_{2-6}$ alkynyl$CH_2$C (O), CHC(O)$C_{1-6}$ alkyl, CHC(O)$C_{2-6}$ alkenyl, CHC(O)$C_{2-6}$ alkynyl, $C_{1-6}$ alkylCHC(O), $C_{2-6}$ alkenylCHC(O), or $C_{2-6}$ alkynylCHC(O); Ar is independently H, an optionally substituted 4-7-member aryl, an optionally substituted 4-7-member heteroaryl, an optionally substituted 4-7-member cycloalkyl, or an optionally substituted 4-7-member heterocycloalkyl; $R^3$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, C(O)OC$_{2-6}$ alkynyl, an optionally substituted 4-7-member aryl, an optionally substituted 4-7-member heteroaryl, an optionally substituted 4-7-member cycloalkyl, or an optionally substituted 4-7-member heterocycloalkyl; and n is 0 to 4.

In aspects of this embodiment, a honeybee repellant may be a compound of formula XIe:

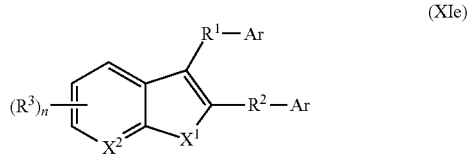

(XIe)

wherein: $X^1$ and $X^2$ are each independently C, N, or S; $R^1$ is N, NH, NH$_2$, NHNH$_2$, N(OH), NCO, (N)C(O), NHC(O), NHC(O)C$_{1-6}$ alkyl, C$_{1-6}$ alkylNHC(O), NC(O), NHC(O)C$_{1-6}$ alkyl, C$_{1-6}$ alkylNC(O), CNHC(O), CNHC(O)C$_{1-6}$ alkyl, C$_{1-6}$ alkylCNHC(O), CNC(O), CNC(O)C$_{1-6}$ alkyl, C$_{1-6}$ alkylCNC(O), CNNHC(O), CNNHC(O)C$_{1-6}$ alkyl, C$_{1-6}$ alkylCNNHC(O), CNNC(O), CNNC(O)C$_{1-6}$ alkyl, or C$_{1-6}$ alkylCNNC(O); $R^2$ is C(O), C(O)$_2$, C$_{1-6}$ alkyl, OC$_{1-6}$ alkyl, C(O)C$_{1-6}$ alkyl, C$_{1-6}$ alkylC(O), C(O)$_2$C$_{1-6}$ alkyl, or C$_{1-6}$ alkylC(O)$_2$, or C(O)OC$_{1-6}$ alkyl; Ar is independently H, an optionally substituted 4-7-member aryl or an optionally substituted 4-7-member heteroaryl; $R^3$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, NH, NH$_2$, NHNH$_2$, NNN, NN, N(OH), NC, NCO, (N)C(O), NCS, (N)C(S), NO, N(O)$_2$, N(O)$_3$, halide, halogen, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, C(O)OC$_{2-6}$ alkynyl, an optionally substituted 4-7-member aryl, an optionally substituted 4-7-member heteroaryl, an optionally substituted 4-7-member cycloalkyl, or an optionally substituted 4-7-member heterocycloalkyl; and n is 0 to 4.

In aspects of this embodiment, a honeybee repellant may be a compound of formula XIf:

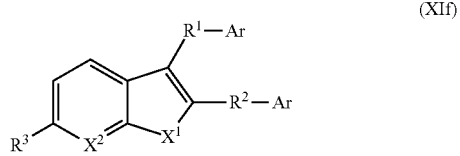

(XIf)

wherein: $X^1$ and $X^2$ are each independently C, N, O or S; $R^1$ is N, NH, NH$_2$, NHNH$_2$, NNN, NN, N(OH), NC, NCO, (N)C(O), NHC(O), NHC(O)C$_{1-6}$ alkyl, NHC(O)C$_{2-6}$ alkenyl, NHC(O)C$_{2-6}$ alkynyl, C$_{1-6}$ alkylNHC(O), C$_{2-6}$ alkenylNHC(O), C$_{2-6}$ alkynylNHC(O), NC(O), NHC(O)C$_{1-6}$ alkyl, NC(O)C$_{2-6}$ alkenyl, NC(O)C$_{2-6}$ alkynyl, C$_{1-6}$ alkylNC(O), C$_{2-6}$ alkenylNC(O), C$_{2-6}$ alkynylNC(O), CNHC(O), CNHC(O)C$_{1-6}$ alkyl, CNHC(O)C$_{2-6}$ alkenyl, CNHC(O)C$_{2-6}$ alkynyl, C$_{1-6}$ alkylCNHC(O), C$_{2-6}$ alkenylCNHC(O), C$_{2-6}$ alkynylCNHC(O), CNC(O), CNC(O)C$_{1-6}$ alkyl, CNC(O)C$_{2-6}$ alkenyl, CNC(O)C$_{2-6}$ alkynyl, C$_{1-6}$ alkylCNC(O), C$_{2-6}$ alkenylCNC(O), C$_{2-6}$ alkynylCNC(O), CNNHC(O), CNNHC(O)C$_{1-6}$ alkyl, CNNHC(O)C$_{2-6}$ alkenyl, CNNHC(O)C$_{2-6}$ alkynyl, C$_{1-6}$ alkylCNNHC(O), C$_{2-6}$ alkenylCNNHC(O), C$_{2-6}$ alkynylCNNHC(O), CNNC(O), CNNC(O)C$_{1-6}$ alkyl, CNNC(O)C$_{2-6}$ alkenyl, CNNC(O)C$_{2-6}$ alkynyl, C$_{1-6}$ alkylCNNC(O), C$_{2-6}$ alkenylCNNC(O), or C$_{2-6}$ alkynylCNNC(O); $R^2$ is C(O), C(O)$_2$, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)C$_{1-6}$ alkyl, C(O)C$_{2-6}$ alkenyl, C(O)C$_{2-6}$ alkynyl, C$_{1-6}$ alkylC(O), C$_{2-6}$ alkenylC(O), C$_{2-6}$ alkynylC(O), C(O)$_2$C$_{1-6}$ alkyl, C(O)$_2$C$_{2-6}$ alkenyl, C(O)$_2$C$_{2-6}$ alkynyl, C$_{1-6}$ alkylC(O)$_2$, C$_{2-6}$ alkenylC(O)$_2$, C$_{2-6}$ alkynylC(O)$_2$, C(O)OC$_{1-6}$ alkyl, C(O)OC$_{2-6}$ alkenyl, C(O)OC$_{2-6}$ alkynyl, C$_{1-6}$ alkylC(O)O, C$_{2-6}$ alkenylC(O)O, C$_{2-6}$ alkynylC(O)O, CH$_2$C(O)C$_{1-6}$ alkyl, CH$_2$C(O)C$_{2-6}$ alkenyl, CH$_2$C(O)C$_{2-6}$ alkynyl, C$_{1-6}$ alkylCH$_2$C(O), C$_{2-6}$ alkenylCH$_2$C(O), or C$_{2-6}$ alkynylCH$_2$C(O), CHC(O)C$_{1-6}$ alkyl, CHC(O)C$_{2-6}$ alkenyl, CHC(O)C$_{2-6}$ alkynyl, C$_{1-6}$ alkylCHC(O), C$_{2-6}$ alkenylCHC(O), or C$_{2-6}$ alkynylCHC(O); Ar is independently H, an optionally substituted 4-7-member aryl, an optionally substituted 4-7-member heteroaryl, an optionally substituted 4-7-member cycloalkyl, or an optionally substituted 4-7-member heterocycloalkyl; and $R^3$ is H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, C(O)OC$_{2-6}$ alkynyl, an optionally substituted 4-7-member aryl, an optionally substituted 4-7-member heteroaryl, an optionally substituted 4-7-member cycloalkyl, or an optionally substituted 4-7-member heterocycloalkyl.

In aspects of this embodiment, a honeybee repellant may be a compound of formula XIg:

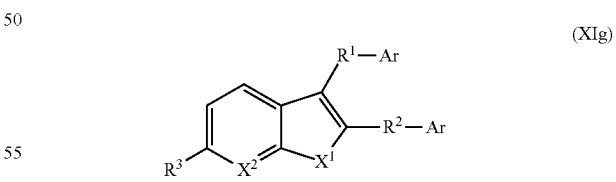

(XIg)

wherein: $X^1$ and $X^2$ are each independently C, N, or S; $R^1$ is N, NH, NH$_2$, NHNH$_2$, N(OH), NCO, (N)C(O), NHC(O), NHC(O)C$_{1-6}$ alkyl, C$_{1-6}$ alkylNHC(O), NC(O), NHC(O)C$_{1-6}$ alkyl, C$_{1-6}$ alkylNC(O), CNHC(O), CNHC(O)C$_{1-6}$ alkyl, C$_{1-6}$ alkylCNHC(O), CNC(O), CNC(O)C$_{1-6}$ alkyl, C$_{1-6}$ alkylCNC(O), CNNHC(O), CNNHC(O)C$_{1-6}$ alkyl, C$_{1-6}$ alkylCNNHC(O), CNNC(O), CNNC(O)C$_{1-6}$ alkyl, or C$_{1-6}$ alkylCNNC(O); $R^2$ is C(O), C(O)$_2$, C$_{1-6}$ alkyl, OC$_{1-6}$ alkyl, C(O)C$_{1-6}$ alkyl, C$_{1-6}$ alkylC(O), C(O)$_2$C$_{1-6}$ alkyl, C$_{1-6}$ alkylC(O)$_2$, C(O)OC$_{1-6}$ alkyl, or C$_{1-6}$ alkylC(O)O; Ar is independently H, an optionally substituted 4-7-member aryl or an optionally substituted 4-7-member heteroaryl; and R³ is independently H, OH, OOH, O, OO, C(O), C(O)H, C(O) OH, OC(O)O, C(O)NH₂, C(O)NC(O), C(NH)NH₂, CN, CNH, C(O)N, OCN, NHC(O)O, NH, NH₂, NHNH₂, NNN, NN, N(OH), NC, NCO, (N)C(O), NCS, (N)C(S), NO, N(O)₂, N(O)₃, halide, halogen, C₁₋₆ alkyl, C₂₋₆ alkenyl, C₂₋₆ alkynyl, OC₁₋₆ alkyl, OC₂₋₆ alkenyl, OC₂₋₆ alkynyl, C(O)₂C₁₋₆ alkyl, C(O)₂C₂₋₆ alkenyl, C(O)₂C₂₋₆ alkynyl, C(O)OC₁₋₆ alkyl, C(O)OC₂₋₆ alkenyl, C(O)OC₂₋₆ alkynyl, an optionally substituted 4-7-member aryl, an optionally substituted 4-7-member heteroaryl, an optionally substituted 4-7-member cycloalkyl, or an optionally substituted 4-7-member heterocycloalkyl.

In aspects of this embodiment, a honeybee repellant of formula XI disclosed herein an optionally substituted [3-amino-6-(3-pyridinyl)thieno[2,3-b]pyridin-2-yl](phenyl) methanone or an optionally substituted 3-iodo-N'-[(2-methyl-1H-indol-3-yl)methylene]benzohydrazide.

In aspects of this embodiment, a honeybee repellant of formula XI disclosed herein is

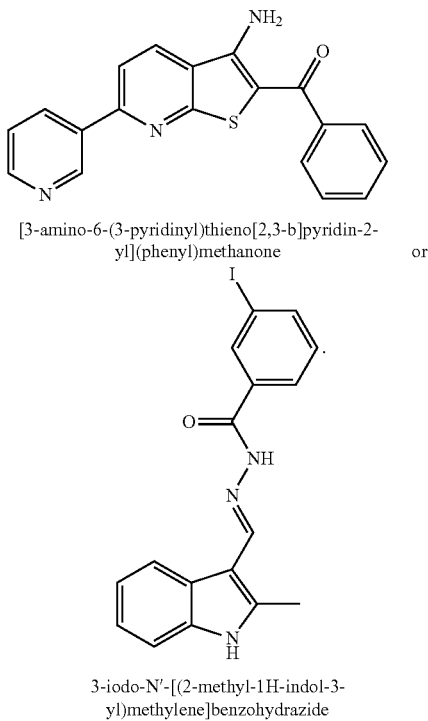

[3-amino-6-(3-pyridinyl)thieno[2,3-b]pyridin-2-yl](phenyl)methanone          or 3-iodo-N'-[(2-methyl-1H-indol-3-yl)methylene]benzohydrazide In aspects of this embodiment, a honeybee repellant is not [3-amino-6-(3-pyridinyl)thieno[2,3-b]pyridin-2-yl](phenyl) methanone or 3-iodo-N'-[(2-methyl-1H-indol-3-yl)methylene]benzohydrazide.

In another embodiment, a honeybee repellant may be a compound of formula XII:

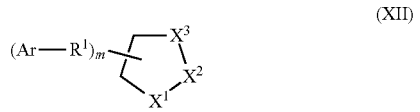

(XII)

wherein: X¹, X² and X³ are each independently C, N, O or S; R¹ is independently H, OH, OOH, O, OO, C(O), C(O)H, C(O)OH, OC(O)O, C(O)NH₂, C(O)NC(O), C(NH)NH₂, CN, CNH, C(O)N, OCN, NHC(O)O, CS, C(S)H, OC(S)N, SCN, CNS, (N)C(S), NCS, (N)C(S), NO, N(O)₂, N(O)₃, SH, S(O), S(O)₂, S(O)₃, S(O)₂N, aminoalkyl, halide, haloalkenyl, haloalkoxyl, haloalkyl, halogen, trihalomethanesulfonyl, trihalomethanesulfonamido, trihalomethoxy, oxoalkyl, on/alkyl, NH, NH₂, NHNH₂, NNN, NN, N(OH), NC, NCO, (N)C(O), NHC(O), NHC(O)C₁₋₆ alkyl, NHC(O)C₂₋₆ alkenyl, NHC(O)C₂₋₆ alkynyl, C₁₋₆ alkylNHC(O), C₂₋₆ alkenylNHC(O), C₂₋₆ alkynylNHC(O), NC(O), NHC(O)C₁₋₆ alkyl, NC(O)C₂₋₆ alkenyl, NC(O)C₂₋₆ alkynyl, C₁₋₆ alkylNC(O), C₂₋₆ alkenylNC(O), C₂₋₆ alkynylNC(O), CNHC(O), CNHC(O)C₁₋₆ alkyl, CNHC(O)C₂₋₆ alkenyl, CNHC(O)C₂₋₆ alkynyl, C₁₋₆ alkylCNHC(O), C₂₋₆ alkenylCNHC(O), C₂₋₆ alkynylCNHC(O), CNC(O), CNC(O)C₁₋₆ alkyl, CNC(O)C₂₋₆ alkenyl, CNC(O)C₂₋₆ alkynyl, C₁₋₆ alkylCNC(O), C₂₋₆ alkenylCNC(O), C₂₋₆ alkynylCNC(O), CNNHC(O), CNNHC(O)C₁₋₆ alkyl, CNNHC(O)C₂₋₆ alkenyl, CNNHC(O)C₂₋₆ alkynyl, C₁₋₆ alkylCNNHC(O), C₂₋₆ alkenylCNNHC(O), C₂₋₆ alkynylCNNHC(O), CNNC(O), CNNC(O)C₁₋₆ alkyl, CNNC(O)C₂₋₆ alkenyl, CNNC(O)C₂₋₆ alkynyl, C₁₋₆ alkylCNNC(O), C₂₋₆ alkenylCNNC(O), C₂₋₆ alkynylCNNC(O), C(O), C(O)₂, C₁₋₆ alkyl, C₂₋₆ alkenyl, C₂₋₆ alkynyl, OC₁₋₆ alkyl, OC₂₋₆ alkenyl, OC₂₋₆ alkynyl, C(O)C₁₋₆ alkyl, C(O)C₂₋₆ alkenyl, C(O)C₂₋₆ alkynyl, C₁₋₆ alkylC(O), C₂₋₆ alkenylC(O), C₂₋₆ alkynylC(O), C(O)₂C₁₋₆ alkyl, C(O)₂C₂₋₆ alkenyl, C(O)₂C₂₋₆ alkynyl, C₁₋₆ alkylC(O)₂, C₂₋₆ alkenylC(O)₂, C₂₋₆ alkynylC(O)₂, C(O)OC₁₋₆ alkyl, C(O)OC₂₋₆ alkenyl, C(O)OC₂₋₆ alkynyl, C₁₋₆ alkylC(O)O, C₂₋₆ alkenylC(O)O, C₂₋₆ alkynylC(O)O, CH₂C(O)C₁₋₆ alkyl, CH₂C(O)C₂₋₆ alkenyl, CH₂C(O)C₂₋₆ alkynyl, C₁₋₆ alkylCH₂C(O), C₂₋₆ alkenylCH₂C(O), or C₂₋₆ alkynylCH₂C(O), CHC(O)C₁₋₆ alkyl, CHC(O)C₂₋₆ alkenyl, CHC(O)C₂₋₆ alkynyl, C₁₋₆ alkylCHC(O), C₂₋₆ alkenylCHC(O), or C₂₋₆ alkynylCHC (O); Ar is independently absent, H, an optionally substituted 4-7-member aryl, an optionally substituted 4-7-member heteroaryl, an optionally substituted 4-7-member cycloalkyl, or an optionally substituted 4-7-member heterocycloalkyl; and m is 0 to 5.

In aspects of this embodiment, a honeybee repellant may be a compound of formula XIIa:

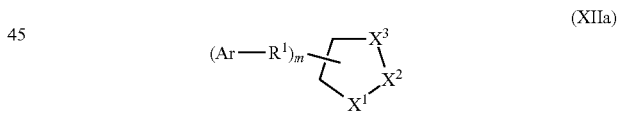

(XIIa)

wherein: X¹, X² and X³ are each independently C, N or S; R¹ is independently H, OH, OOH, O, OO, C(O), C(O)H, C(O)OH, OC(O)O, C(O)NH₂, C(O)NC(O), C(NH)NH₂, CN, CNH, C(O)N, OCN, NHC(O)O, NH, NH₂, NHNH₂, N(OH), NCO, (N)C(O), NHC(O), NHC(O)C₁₋₆ alkyl, C₁₋₆ alkylNHC(O), NC(O), NHC(O)C₁₋₆ alkyl, C₁₋₆ alkylNC(O), CNHC(O), CNHC(O)C₁₋₆ alkyl, C₁₋₆ alkylCNHC(O), CNC(O), CNC(O)C₁₋₆ alkyl, C₁₋₆ alkylCNC(O), CNNHC(O), CNNHC(O)C₁₋₆ alkyl, C₁₋₆ alkylCNNHC(O), CNNC(O), CNNC(O)C₁₋₆ alkyl, C₁₋₆ alkylCNNC(O), C(O), C(O)₂, C₁₋₆ alkyl, OC₁₋₆ alkyl, C(O)C₁₋₆ alkyl, C₁₋₆ alkylC(O), C(O)₂C₁₋₆ alkyl, C₁₋₆ alkylC(O)₂, C(O)OC₁₋₆ alkyl, CH₂C(O)C₁₋₆ alkyl, C₁₋₆ alkylCH₂C(O), CHC(O)C₁₋₆ alkyl, or C₁₋₆ alkylCHC(O); Ar is independently absent, H, an optionally substituted 4-7-member aryl or an optionally substituted 4-7-member heteroaryl; and m is 0 to 5.

In aspects of this embodiment, a honeybee repellant may be a compound of formula XIIb:

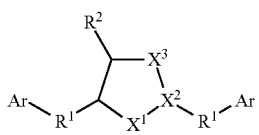
(XIIb)

wherein: $X^1$, $X^2$ and $X^3$ are each independently C, N, O or S; $R^1$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, NH, NH$_2$, NHNH$_2$, NNN, NN, N(OH), NC, NCO, (N)C(O), NHC(O), NHC(O)C$_{1-6}$ alkyl, NHC(O)C$_{2-6}$ alkenyl, NHC(O)C$_{2-6}$ alkynyl, C$_{1-6}$ alkylNHC(O), C$_{2-6}$ alkenylNHC(O), C$_{2-6}$ alkynylNHC(O), NC(O), NHC(O)C$_{1-6}$ alkyl, NC(O)C$_{2-6}$ alkenyl, NC(O)C$_{2-6}$ alkynyl, C$_{1-6}$ alkylNC(O), C$_{2-6}$ alkenylNC(O), C$_{2-6}$ alkynylNC(O), CNHC(O), CNHC(O)C$_{1-6}$ alkyl, CNHC(O)C$_{2-6}$ alkenyl, CNHC(O)C$_{2-6}$ alkynyl, C$_{1-6}$ alkylCNHC(O), C$_{2-6}$ alkenylCNHC(O), C$_{2-6}$ alkynylCNHC(O), CNC(O), CNC(O)C$_{1-6}$ alkyl, CNC(O)C$_{2-6}$ alkenyl, CNC(O)C$_{2-6}$ alkynyl, C$_{1-6}$ alkylCNC(O), C$_{2-6}$ alkenylCNC(O), C$_{2-6}$ alkynylCNC(O), CNNHC(O), CNNHC(O)C$_{1-6}$ alkyl, CNNHC(O)C$_{2-6}$ alkenyl, CNNHC(O)C$_{2-6}$ alkynyl, C$_{1-6}$ alkylCNNHC(O), C$_{2-6}$ alkenylCNNHC(O), C$_{2-6}$ alkynylCNNHC(O), CNNC(O), CNNC(O)C$_{1-6}$ alkyl, CNNC(O)C$_{2-6}$ alkenyl, CNNC(O)C$_{2-6}$ alkynyl, C$_{1-6}$ alkylCNNC(O), C$_{2-6}$ alkenylCNNC(O), C$_{2-6}$ alkynylCNNC(O), C(O), C(O)$_2$, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)C$_{1-6}$ alkyl, C(O)C$_{2-6}$ alkenyl, C(O)C$_{2-6}$ alkynyl, C$_{1-6}$ alkylC(O), C$_{2-6}$ alkenylC(O), C$_{2-6}$ alkynylC(O), C(O)$_2$C$_{1-6}$ alkyl, C(O)$_2$C$_{2-6}$ alkenyl, C(O)$_2$C$_{2-6}$ alkynyl, C$_{1-6}$ alkylC(O)$_2$, C$_{2-6}$ alkenylC(O)$_2$, C$_{2-6}$ alkynylC(O)$_2$, C(O)OC$_{1-6}$ alkyl, C(O)OC$_{2-6}$ alkenyl, C(O)OC$_{2-6}$ alkynyl, C$_{1-6}$ alkylC(O)O, C$_{2-6}$ alkenylC(O)O, C$_{2-6}$ alkynylC(O)O, CH$_2$C(O)C$_{1-6}$ alkyl, CH$_2$C(O)C$_{2-6}$ alkenyl, CH$_2$C(O)C$_{2-6}$ alkynyl, C$_{1-6}$ alkylCH$_2$C(O), C$_{2-6}$ alkenylCH$_2$C(O), or C$_{2-6}$ alkynylCH$_2$C(O), CHC(O)C$_{1-6}$ alkyl, CHC(O)C$_{2-6}$ alkenyl, CHC(O)C$_{2-6}$ alkynyl, C$_{1-6}$ alkylCHC(O), C$_{2-6}$ alkenylCHC(O), or C$_{2-6}$ alkynylCHC(O); $R^2$ is H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NCS, (N)C(S), NO, N(O)$_2$, N(O)$_3$, SH, S(O), S(O)$_2$, S(O)$_3$, S(O)$_2$N, halide, haloalkenyl, haloalkoxyl, haloalkyl, halogen, trihalomethanesulfonyl, trihalomethanesulfonamido, trihalomethoxy, oxoalkyl, oxyalkyl, NH, NH$_2$, NHNH$_2$, NNN, NN, N(OH), NC, NCO, (N)C(O), or NHC(O); Ar is independently absent, H, an optionally substituted 4-7-member aryl, an optionally substituted 4-7-member heteroaryl, an optionally substituted 4-7-member cycloalkyl, or an optionally substituted 4-7-member heterocycloalkyl.

In aspects of this embodiment, a honeybee repellant may be a compound of formula XIIc:

(XIIc)

wherein: $X^1$, $X^2$ and $X^3$ are each independently C, N or S; $R^1$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, NH, NH$_2$, NHNH$_2$, N(OH), NCO, (N)C(O), NHC(O), NHC(O)C$_{1-6}$ alkyl, C$_{1-6}$ alkylNHC(O), NC(O), NHC(O)C$_{1-6}$ alkyl, C$_{1-6}$ alkylNC(O), CNHC(O), CNHC(O)C$_{1-6}$ alkyl, C$_{1-6}$ alkylCNHC(O), CNC(O), CNC(O)C$_{1-6}$ alkyl, C$_{1-6}$ alkylCNC(O), CNNHC(O), CNNHC(O)C$_{1-6}$ alkyl, C$_{1-6}$ alkylCNNHC(O), CNNC(O), CNNC(O)C$_{1-6}$ alkyl, C$_{1-6}$ alkylCNNC(O), C(O), C(O)$_2$, C$_{1-6}$ alkyl, OC$_{1-6}$ alkyl, C(O)C$_{1-6}$ alkyl, C$_{1-6}$ alkylC(O), C(O)$_2$C$_{1-6}$ alkyl, or C$_{1-6}$ alkylC(O)$_2$, CH$_2$C(O)C$_{1-6}$ alkyl, C$_{1-6}$ alkylCH$_2$C(O), CHC(O)C$_{1-6}$ alkyl, or C$_{1-6}$ alkylCHC(O); $R^2$ is H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, NO, N(O)$_2$, N(O)$_3$, SH, S(O), S(O)$_2$, S(O)$_3$, S(O)$_2$N, halide, halogen, NH, NH$_2$, NHNH$_2$, NNN, NN, N(OH), NC, NCO, (N)C(O), or NHC(O); and Ar is independently absent, H, an optionally substituted 4-7-member aryl, or an optionally substituted 4-7-member heteroaryl.

In aspects of this embodiment, a honeybee repellant of formula XII disclosed herein an optionally substituted N,N'-bis(2-acetylphenyl)tetrahydro-2,5-thiophenedicarboxamide or an optionally substituted 2-[2-(4-chlorophenyl)-2-oxoethylidene]-1,3-thiazolidin-4-one.

In aspects of this embodiment, a honeybee repellant of formula XII disclosed herein is

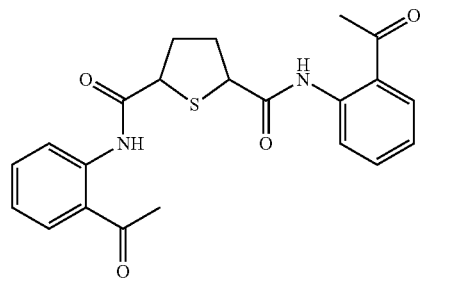

N,N'-bis(2-acetylphenyl)tetrahydro-2,5-thiophenedicarboxamide    or

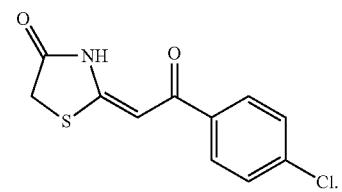

2-[2-(4-chlorophenyl)-2-oxoethylidene]-1,3-thiazolidin-4-one

In aspects of this embodiment, a honeybee repellant is not N,N'-bis(2-acetylphenyl)tetrahydro-2,5-thiophenedicarboxamide or 2-[2-(4-chlorophenyl)-2-oxoethylidene]-1,3-thiazolidin-4-one.

In another embodiment, a honeybee repellant may be a compound of formula XIII:

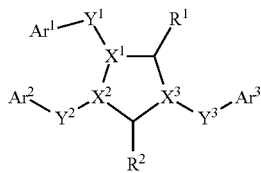

(XIII)

wherein: $X^1$, $X^2$ and $X^3$ are each independently C, N, O or S; $Y^1$, $Y^2$ and $Y^3$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, NH, NH$_2$, NHNH$_2$, NNN, NN, N(OH), NC, NCO, (N)C(O), NHC(O), NHC(O)C$_{1-6}$ alkyl, NHC(O)C$_{2-6}$ alkenyl, NHC(O)C$_{2-6}$ alkynyl, C$_{1-6}$ alkylNHC(O), C$_{2-6}$ alkenylNHC(O), C$_{2-6}$ alkynylNHC(O), NC(O), NHC(O)C$_{1-6}$ alkyl, NC(O)C$_{2-6}$ alkenyl, NC(O)C$_{2-6}$ alkynyl, C$_{1-6}$ alkylNC(O), C$_{2-6}$ alkenylNC(O), C$_{2-6}$ alkynylNC(O), CNHC(O), CNHC(O)C$_{1-6}$ alkyl, CNHC(O)C$_{2-6}$ alkenyl, CNHC(O)C$_{2-6}$ alkynyl, C$_{1-6}$ alkylCNHC(O), C$_{2-6}$ alkenylCNHC(O), C$_{2-6}$ alkynylCNHC(O), CNC(O), CNC(O)C$_{1-6}$ alkyl, CNC(O)C$_{2-6}$ alkenyl, CNC(O)C$_{2-6}$ alkynyl, C$_{1-6}$ alkylCNC(O), C$_{2-6}$ alkenylCNC(O), C$_{2-6}$ alkynylCNC(O), CNNHC(O), CNNHC(O)C$_{1-6}$ alkyl, CNNHC(O)C$_{2-6}$ alkenyl, CNNHC(O)C$_{2-6}$ alkynyl, C$_{1-6}$ alkylCNNHC(O), C$_{2-6}$ alkenylCNNHC(O), C$_{2-6}$ alkynylCNNHC(O), CNNC(O), CNNC(O)C$_{1-6}$ alkyl, CNNC(O)C$_{2-6}$ alkenyl, CNNC(O)C$_{2-6}$ alkynyl, C$_{1-6}$ alkylCNNC(O), C$_{2-6}$ alkenylCNNC(O), C$_{2-6}$ alkynylCNNC(O), C(O), C(O)$_2$, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)C$_{1-6}$ alkyl, C(O)C$_{2-6}$ alkenyl, C(O)C$_{2-6}$ alkynyl, C$_{1-6}$ alkylC(O), C$_{2-6}$ alkenylC(O), C$_{2-6}$ alkynylC(O), C(O)$_2$C$_{1-6}$ alkyl, C(O)$_2$C$_{2-6}$ alkenyl, C(O)$_2$C$_{2-6}$ alkynyl, C$_{1-6}$ alkylC(O)$_2$, C$_{2-6}$ alkenylC(O)$_2$, C$_{2-6}$ alkynylC(O)$_2$, C(O)OC$_{1-6}$ alkyl, C(O)OC$_{2-6}$ alkenyl, C(O)OC$_{2-6}$ alkynyl, C$_{1-6}$ alkylC(O)O, C$_{2-6}$ alkenylC(O)O, C$_{2-6}$ alkynylC(O)O, CH$_2$C(O)C$_{1-6}$ alkyl, CH$_2$C(O)C$_{2-6}$ alkenyl, CH$_2$C(O)C$_{2-6}$ alkynyl, C$_{1-6}$ alkylCH$_2$C(O), C$_{2-6}$ alkenylCH$_2$C(O), C$_{2-6}$ alkynylCH$_2$C(O), CHC(O)C$_{1-6}$ alkyl, CHC(O)C$_{2-6}$ alkenyl, CHC(O)C$_{2-6}$ alkynyl, C$_{1-6}$ alkylCHC(O), C$_{2-6}$ alkenylCHC(O), or C$_{2-6}$ alkynylCHC(O); Ar$^1$, Ar$^2$ and Ar$^3$ are each independently absent, H, an optionally substituted 4-7-member aryl, an optionally substituted 4-7-member heteroaryl, an optionally substituted 4-7-member cycloalkyl, or an optionally substituted 4-7-member heterocycloalkyl; and R$^1$ and R$^2$ are each independently H, OH, OOH, O, OO, C(O), C(O)H, C(O)OH, OC(O)O, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, C(O)OC$_{2-6}$ alkynyl, halide, haloalkenyl, haloalkoxyl, haloalkyl, or halogen.

In aspects of this embodiment, a honeybee repellant may be a compound of formula XIIIa:

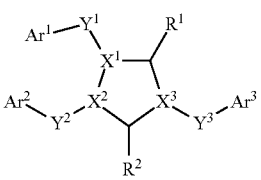

(XIIIa)

wherein: $X^1$, $X^2$ and $X^3$ are each independently C, N or O; $Y^1$, $Y^2$ and $Y^3$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, NH, NH$_2$, NHNH$_2$, N(OH), NCO, (N)C(O), NHC(O), NHC(O)C$_{1-6}$ alkyl, C$_{1-6}$ alkylNHC(O), NC(O), NHC(O)C$_{1-6}$ alkyl, C$_{1-6}$ alkylNC(O), CNHC(O), CNHC(O)C$_{1-6}$ alkyl, C$_{1-6}$ alkylCNHC(O), CNC(O), CNC(O)C$_{1-6}$ alkyl, C$_{1-6}$ alkylCNC(O), CNNHC(O), CNNHC(O)C$_{1-6}$ alkyl, C$_{1-6}$ alkylCNNHC(O), CNNC(O), CNNC(O)C$_{1-6}$ alkyl, C$_{1-6}$ alkylCNNC(O), C(O), C(O)$_2$, C$_{1-6}$ alkyl, OC$_{1-6}$ alkyl, C(O)C$_{1-6}$ alkyl, C$_{1-6}$ alkylC(O), C(O)$_2$C$_{1-6}$ alkyl, C$_{1-6}$ alkylC(O)$_2$, C(O), C(O)OC$_{1-6}$ alkyl, CH$_2$C(O)C$_{1-6}$ alkyl, C$_{1-6}$ alkylCH$_2$C(O), CHC(O)C$_{1-6}$ alkyl, C$_{1-6}$ alkylCHC(O); Ar$^1$, Ar$^2$ and Ar$^3$ are each independently absent, H, an optionally substituted 4-7-member aryl or an optionally substituted 4-7-member heteroaryl; and R$^1$ and R$^2$ are each independently H, OH, OOH, O, OO, C(O), C(O)H, C(O)OH, OC(O)O, C$_{1-6}$ alkyl, OC$_{1-6}$ alkyl, C(O)$_2$C$_{1-6}$ alkyl, halide, or halogen.

In aspects of this embodiment, a honeybee repellant may be a compound of formula XIIIb:

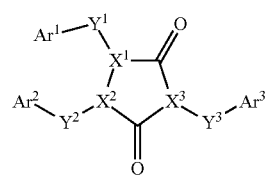

(XIIIb)

wherein: $X^1$, $X^2$ and $X^3$ are each independently C, N, O or S; $Y^1$, $Y^2$ and $Y^3$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, NH, NH$_2$, NHNH$_2$, NNN, NN, N(OH), NC, NCO, (N)C(O), NHC(O), NHC(O)C$_{1-6}$ alkyl, NHC(O)C$_{2-6}$ alkenyl, NHC(O)C$_{2-6}$ alkynyl, C$_{1-6}$ alkylNHC(O), C$_{2-6}$ alkenylNHC(O), C$_{2-6}$ alkynylNHC(O), NC(O), NHC(O)C$_{1-6}$ alkyl, NC(O)C$_{2-6}$ alkenyl, NC(O)C$_{2-6}$ alkynyl, C$_{1-6}$ alkylNC(O), C$_{2-6}$ alkenylNC(O), C$_{2-6}$ alkynylNC(O), CNHC(O), CNHC(O)C$_{1-6}$ alkyl, CNHC(O)C$_{2-6}$ alkenyl, CNHC(O)C$_{2-6}$ alkynyl, C$_{1-6}$ alkylCNHC(O), C$_{2-6}$ alkenylCNHC(O), C$_{2-6}$ alkynylCNHC(O), CNC(O), CNC(O)C$_{1-6}$ alkyl, CNC(O)C$_{2-6}$ alkenyl, CNC(O)C$_{2-6}$ alkynyl, C$_{1-6}$ alkylCNC(O), C$_{2-6}$ alkenylCNC(O), C$_{2-6}$ alkynylCNC(O), CNNHC(O), CNNHC(O)C$_{1-6}$ alkyl, CNNHC(O)C$_{2-6}$ alkenyl, CNNHC(O)C$_{2-6}$ alkynyl, C$_{1-6}$ alkylCNNHC(O), C$_{2-6}$ alkenylCNNHC(O), C$_{2-6}$ alkynylCNNHC(O), CNNC(O), CNNC(O)C$_{1-6}$ alkyl, CNNC(O)C$_{2-6}$ alkenyl, CNNC(O)C$_{2-6}$ alkynyl, C$_{1-6}$ alkylCNNC(O), C$_{2-6}$ alkenylCNNC(O), C$_{2-6}$ alkynylCNNC(O), C(O), C(O)$_2$, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)C$_{1-6}$ alkyl, C(O)C$_{2-6}$ alkenyl, C(O)C$_{2-6}$ alkynyl, C$_{1-6}$ alkylC(O), C$_{2-6}$ alkenylC(O), C$_{2-6}$ alkynylC(O), C(O)$_2$C$_{1-6}$ alkyl, C(O)$_2$C$_{2-6}$ alkenyl, C(O)$_2$C$_{2-6}$ alkynyl, C$_{1-6}$ alkylC(O)$_2$, C$_{2-6}$ alkenylC(O)$_2$, C$_{2-6}$ alkynylC(O)$_2$, C(O)OC$_{1-6}$ alkyl, C(O)OC$_{2-6}$ alkenyl, C(O)OC$_{2-6}$ alkynyl, C$_{1-6}$ alkylC(O)O, C$_{2-6}$ alkenylC(O)O, C$_{2-6}$ alkynylC(O)O, CH$_2$C(O)C$_{1-6}$ alkyl, CH$_2$C(O)C$_{2-6}$ alkenyl, CH$_2$C(O)C$_{2-6}$ alkynyl, C$_{1-6}$ alkylCH$_2$C(O), C$_{2-6}$ alkenylCH$_2$C(O), or C$_{2-6}$ alkynylCH$_2$C(O), CHC(O)C$_{1-6}$ alkyl, CHC(O)C$_{2-6}$ alkenyl, CHC(O)C$_{2-6}$ alkynyl, C$_{1-6}$ alkylCHC(O), C$_{2-6}$ alkenylCHC(O), or C$_{2-6}$ alkynylCHC(O); and Ar$^1$, Ar$^2$ and Ar$^3$ are each independently absent, H, an optionally substituted 4-7-member aryl, an optionally substituted 4-7-member heteroaryl, an optionally substituted 4-7-member cycloalkyl, or an optionally substituted 4-7-member heterocycloalkyl.

In aspects of this embodiment, a honeybee repellant may be a compound of formula XIIIc:

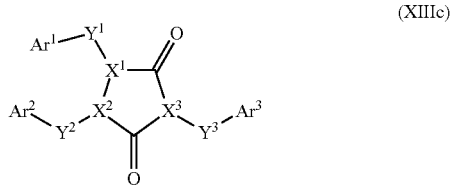

(XIIIc)

wherein: X$^1$, X$^2$ and X$^3$ are each independently C, N or O; Y$^1$, Y$^2$ and Y$^3$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, NH, NH$_2$, NHNH$_2$, N(OH), NCO, (N)C(O), NHC(O), NHC(O)C$_{1-6}$ alkyl, C$_{1-6}$ alkylNHC(O), NC(O), NHC(O)C$_{1-6}$ alkyl, C$_{1-6}$ alkylNC(O), CNHC(O), CNHC(O)C$_{1-6}$ alkyl, C$_{1-6}$ alkylCNHC(O), CNC(O), CNC(O)C$_{1-6}$ alkyl, C$_{1-6}$ alkylCNC(O), CNNHC(O), CNNHC(O)C$_{1-6}$ alkyl, C$_{1-6}$ alkylCNNHC(O), CNNC(O), CNNC(O)C$_{1-6}$ alkyl, C$_{1-6}$ alkylCNNC(O), C(O), C(O)$_2$, C$_{1-6}$ alkyl, OC$_{1-6}$ alkyl, C(O)C$_{1-6}$ alkyl, C$_{1-6}$ alkylC(O), C(O)$_2$C$_{1-6}$ alkyl, C$_{1-6}$ alkylC(O)$_2$, C(O)OC$_{1-6}$ alkyl, CH$_2$C(O)C$_{1-6}$ alkyl, C$_{1-6}$ alkylCH$_2$C(O), CHC(O)C$_{1-6}$ alkyl, or C$_{1-6}$ alkylCHC(O); and Ar$^1$, Ar$^2$ and Ar$^3$ are each independently absent, H, an optionally substituted 4-7-member aryl or an optionally substituted 4-7-member heteroaryl.

In aspects of this embodiment, a honeybee repellant may be a compound of formula XIIId:

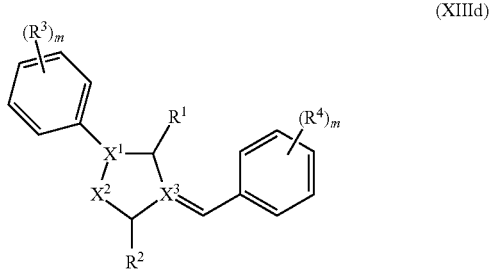

(XIIId)

wherein: X$^1$, X$^2$ and X$^3$ are each independently C, N, O or S; R$^1$ and R$^2$ are each independently H, OH, OOH, O, OO, C(O), C(O)H, C(O)OH, OC(O)O, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, C(O)OC$_{2-6}$ alkynyl, halide, haloalkenyl, haloalkoxyl, haloalkyl, or halogen; R$^3$ and R$^4$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, C(O)OC$_{2-6}$ alkynyl, an optionally substituted 4-7-member aryl, an optionally substituted 4-7-member heteroaryl, an optionally substituted 4-7-member cycloalkyl, or an optionally substituted 4-7-member heterocycloalkyl; and m is 0 to 5.

In aspects of this embodiment, a honeybee repellant may be a compound of formula XIIIe:

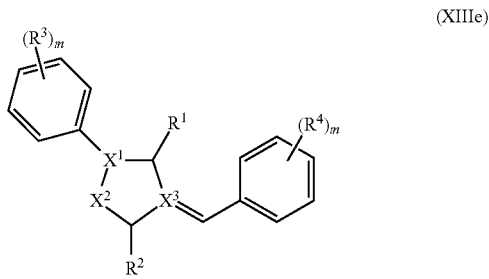

(XIIIe)

wherein: X$^1$, X$^2$ and X$^3$ are each independently C, N or O; R$^1$ and R$^2$ are each independently H, OH, OOH, O, OO, C(O), C(O)H, C(O)OH, OC(O)O, C$_{1-6}$ alkyl, OC$_{1-6}$ alkyl, C(O)$_2$C$_{1-6}$ alkyl, C(O)OC$_{1-6}$ alkyl, halide, or halogen; R$^3$ and W are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, N(OH), NC, NCO, (N)C(O), halide, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, C(O)OC$_{2-6}$ alkynyl, an optionally substituted 4-7-member cycloalkyl, or an optionally substituted 4-7-member heterocycloalkyl; and m is 0 to 5.

In aspects of this embodiment, a honeybee repellant of formula XIII disclosed herein an optionally substituted ethyl 4-{4-[4-(4-morpholinyl)benzylidene]-3,5-dioxo-1-pyrazolidinyl}benzoate.

In aspects of this embodiment, a honeybee repellant of formula XIII disclosed herein is

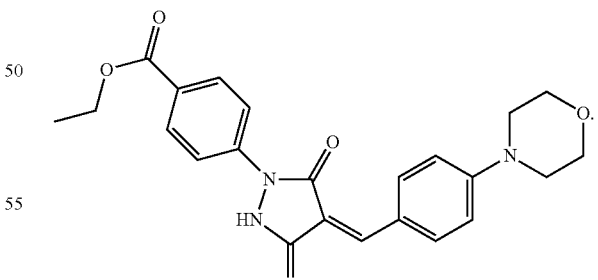

ethyl 4-{4-[4-(4-morpholinyl)benzylidene]-3,5-dioxo-1-pyrazolidinyl}benzoate

In aspects of this embodiment, a honeybee repellant is not ethyl 4-{4-[4-(4-morpholinyl)benzylidene]-3,5-dioxo-1-pyrazolidinyl}benzoate.

In another embodiment, a honeybee repellant may be a compound of formula XIV:

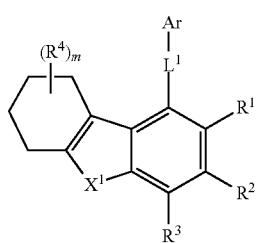

(XIV)

wherein: $X^1$ is C, N, O or S; $L^1$ is OH, OOH, O, OO, OHC, C, C(O), C(O)H, C(O)OH, OC(O)O, C(O)NH$_2$, C(O)NC(O), C(NH)NH$_2$, C(O)N, OCN, NHC(O)O, CS, C(S)H, OC(S)N, SCN, CNS, (N)C(S), N, NH, NH$_2$, NHN, NHNH$_2$, NNN, NN, N(OH), NC, NCH, NHNCH, NCO, (N)C(O), NCS, (N)C(S), NO, N(O)$_2$, S, SH, S(O), S(O)$_2$, C$_{1-6}$ alkyl, C$_{2-6}$ alkenyl, C$_{2-6}$ alkynyl, CNH, CNHC$_{1-6}$ alkyl, CNHC$_{2-6}$ alkenyl, CNHC$_{2-6}$ alkynyl, C$_{1-6}$ alkylCNH, C$_{2-6}$ alkenylCNH, C$_{2-6}$ alkynylCNH, CN, CNC$_{1-6}$ alkyl, CNC$_{2-6}$ alkenyl, CNC$_{2-6}$ alkynyl, C$_{1-6}$ alkylCN, C$_{2-6}$ alkenylCN, C$_{2-6}$ alkynylCN, C(O)C=CNH, C(O)C=CNHC$_{1-6}$ alkyl, C(O)C=CNHC$_{1-6}$ alkenyl, C(O)C=CNHC$_{1-6}$ alkynyl, C$_{1-6}$ alkylC(O)C=CNH, C$_{1-6}$ alkenylC(O)C=CNH, C$_{1-6}$ alkynylC(O)C=CNH, OC$_{1-6}$ alkyl, OC$_{2-6}$ alkenyl, OC$_{2-6}$ alkynyl, C$_{1-6}$ alkylO, C$_{2-6}$ alkenylO, C$_{2-6}$ alkynylO, OHC$_{1-6}$ alkyl, OHC$_{2-6}$ alkenyl, OHC$_{2-6}$ alkynyl, C$_{1-6}$ alkylOH, C$_{2-6}$ alkenylOH, C$_{2-6}$ alkynylOH, OHC(O), OHC(O)C$_{1-6}$ alkyl, OHC(O)C$_{2-6}$ alkenyl, OHC(O)C$_{2-6}$ alkynyl, C$_{1-6}$ alkylOHC(O), C$_{2-6}$ alkenylOHC(O), C$_{2-6}$ alkynylOHC(O), OC(O)C$_{1-6}$ alkyl, OC(O)C$_{2-6}$ alkenyl, OC(O)C$_{2-6}$ alkynyl, C$_{1-6}$ alkylOC(O), C$_{2-6}$ alkenylOC(O), C$_{2-6}$ alkynylOC(O), C(O)$_2$C$_{1-6}$ alkyl, C(O)$_2$C$_{2-6}$ alkenyl, C(O)$_2$C$_{2-6}$ alkynyl, C$_{1-6}$ alkylC(O)$_2$, C$_{2-6}$ alkenylC(O)$_2$, C$_{2-6}$ alkynylC(O)$_2$, C(O)OC$_{1-6}$ alkyl, C(O)OC$_{2-6}$ alkenyl, C(O)OC$_{2-6}$ alkynyl, C$_{1-6}$ alkylC(O)O, C$_{2-6}$ alkenylC(O)O, C$_{2-6}$ alkynylC(O)O, CH$_2$C(O)C$_{1-6}$ alkyl, CH$_2$C(O)C$_{2-6}$ alkenyl, CH$_2$C(O)C$_{2-6}$ alkynyl, C$_{1-6}$ alkylCH$_2$C(O), C$_{2-6}$ alkenylCH$_2$C(O), C$_{2-6}$ alkynylCH$_2$C(O), CHC(O)C$_{1-6}$ alkyl, CHC(O)C$_{2-6}$ alkenyl, CHC(O)C$_{2-6}$ alkynyl, C$_{1-6}$ alkylCHC(O), C$_{2-6}$ alkenylCHC(O), C$_{2-6}$ alkynylCHC(O), CHN, CHNC$_{1-6}$ alkyl, CHNC$_{2-6}$ alkenyl, CHNC$_{2-6}$ alkynyl, C$_{1-6}$ alkylCHN, C$_{2-6}$ alkenylCHN, C$_{2-6}$ alkynylCHN, CHNNH, CHNNHC$_{1-6}$ alkyl, CHNNHC$_{2-6}$ alkenyl, CHNNHC$_{2-6}$ alkynyl, C$_{1-6}$ alkylCHNNH, C$_{2-6}$ alkenylCHNNH, C$_{2-6}$ alkynylCHNNH, NHNC$_{1-6}$ alkyl, NHNC$_{2-6}$ alkenyl, NHNC$_{2-6}$ alkynyl, C$_{1-6}$ alkylNHN, C$_{2-6}$ alkenylNHN, C$_{2-6}$ alkynylNHN, NC$_{1-6}$ alkyl, NC$_{2-6}$ alkenyl, NC$_{2-6}$ alkynyl, C$_{1-6}$ alkylNC, C$_{2-6}$ alkenylNC, C$_{2-6}$ alkynylNC, NHC$_{1-6}$ alkyl, NHC$_{2-6}$ alkenyl, NHC$_{2-6}$ alkynyl, C$_{1-6}$ alkylNH, C$_{2-6}$ alkenylNH, C$_{2-6}$ alkynylNH, NHC(O), NHC(O)C$_{1-6}$ alkyl, NHC(O)C$_{2-6}$ alkenyl, NHC(O)C$_{2-6}$ alkynyl, C$_{1-6}$ alkylNHC(O), C$_{2-6}$ alkenylNHC(O), C$_{2-6}$ alkynylNHC(O), NC(O)C$_{1-6}$ alkyl, NC(O)C$_{2-6}$ alkenyl, NC(O)C$_{2-6}$ alkynyl, C$_{1-6}$ alkylNC(O), C$_{2-6}$ alkenyNC(O), C$_{2-6}$ alkynylNC(O), C(O)NHC$_{1-6}$ alkyl, C(O)NHC$_{2-6}$ alkenyl, C(O)NHC$_{2-6}$ alkynyl, C$_{1-6}$ alkylC(O)NH, C$_{2-6}$ alkenylC(O)NH, C$_{2-6}$ alkynyl C(O)NH, C(O)NC$_{1-6}$ alkyl, C(O)NC$_{2-6}$ alkenyl, or C(O)NC$_{2-6}$ alkynyl, C$_{1-6}$ alkylC(O)N, C$_{2-6}$ alkenylC(O)N, or C$_{2-6}$ alkynyl C(O)N; Ar is an optionally substituted 4-7-member aryl, an optionally substituted 4-7-member heteroaryl, an optionally substituted 4-7-member cycloalkyl, or an optionally substituted 4-7-member heterocycloalkyl; $R^1$, $R^2$ and $R^3$ are each independently H, OH, OOH, O, OO, C(O), C(O)H, C(O)OH, OC(O)O, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, C(O)OC$_{2-6}$ alkynyl, halide, haloalkenyl, haloalkoxyl, haloalkyl, or halogen; $R^4$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, or C(O)OC$_{2-6}$ alkynyl; and m is 0 to 5.

In another embodiment, a honeybee repellant may be a compound of formula XIVa:

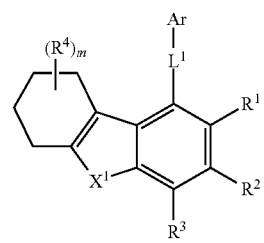

(XIVa)

wherein: $X^1$ is N, O or S; $L^1$ is OH, OOH, O, OO, OHC, C, C(O), C(O)H, C(O)OH, OC(O)O, C(O)NH$_2$, C(O)NC(O), C(NH)NH$_2$, C(O)N, OCN, NHC(O)O, CS, C(S)H, OC(S)N, SCN, CNS, (N)C(S), N, NH, NH$_2$, NHN, NHNH$_2$, NNN, NN, N(OH), NC, NCH, NHNCH, NCO, (N)C(O), NCS, (N)C(S), NO, N(O)$_2$, S, SH, S(O), S(O)$_2$, C$_{1-6}$ alkyl, CNH, CNHC$_{1-6}$ alkyl, C$_{1-6}$ alkylCNH, CN, CNC$_{1-6}$ alkyl, C$_{1-6}$ alkylCN, C(O)C=CNH, C(O)C=CNHC$_{1-6}$ alkyl, C$_{1-6}$ alkylC(O)C=CNH, OC$_{1-6}$ alkyl, C$_{1-6}$ alkylO, OHC$_{1-6}$ alkyl, C$_{1-6}$ alkylOH, OHC(O), OHC(O)C$_{1-6}$ alkyl, C$_{1-6}$ alkylOHC(O), OC(O)C$_{1-6}$ alkyl, C$_{1-6}$ alkylOC(O), C(O)$_2$C$_{1-6}$ alkyl, C$_{1-6}$ alkylC(O)$_2$, C(O)OC$_{1-6}$ alkyl, C$_{1-6}$ alkylC(O)O, CH$_2$C(O)C$_{1-6}$ alkyl, C$_{1-6}$ alkylCH$_2$C(O), CHC(O)C$_{1-6}$ alkyl, C$_{1-6}$ alkylCHC(O), CHN, CHNC$_{1-6}$ alkyl, C$_{1-6}$ alkylCHN, CHNNH, CHNNHC$_{1-6}$ alkyl, C$_{1-6}$ alkylCHNNH, NHNC$_{1-6}$ alkyl, C$_{1-6}$ alkylNHN, NC$_{1-6}$ alkyl, C$_{1-6}$ alkylNC, NHC$_{1-6}$ alkyl, C$_{1-6}$ alkylNH, NHC(O), NHC(O)C$_{1-6}$ alkyl, C$_{1-6}$ alkylNHC(O), NC(O)C$_{1-6}$ alkyl, C$_{1-6}$ alkylNC(O), C(O)NHC$_{1-6}$ alkyl, C$_{1-6}$ alkylC(O)NH, C(O)NC$_{1-6}$ alkyl, or C$_{1-6}$ alkylC(O)N; Ar is an optionally substituted 4-7-member aryl or an optionally substituted 4-7-member heteroaryl; $R^1$, $R^2$ and $R^3$ are each independently H, OH, OOH, O, OO, C(O), C(O)H, C(O)OH, OC(O)O, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, C(O)OC$_{2-6}$ alkynyl, halide, haloalkenyl, haloalkoxyl, haloalkyl, or halogen; $R^4$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), halide, halogen, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, or C(O)OC$_{2-6}$ alkynyl; and m is 0 to 5.

In another embodiment, a honeybee repellant may be a compound of formula XIVb:

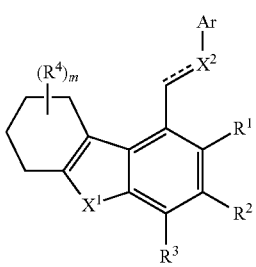

(XIVb)

wherein: $X^1$ and $X^2$ are each independently C, N, O or S; Ar is an optionally substituted 4-7-member aryl, an optionally substituted 4-7-member heteroaryl, an optionally substituted 4-7-member cycloalkyl, or an optionally substituted 4-7-member heterocycloalkyl; $R^1$, $R^2$ and $R^3$ are each independently H, OH, OOH, O, OO, C(O), C(O)H, C(O)OH, OC(O)O, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, $C(O)OC_{2-6}$ alkynyl, halide, haloalkenyl, haloalkoxyl, haloalkyl, or halogen; $R^4$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, or $C(O)OC_{2-6}$ alkynyl; and m is 0 to 5.

In another embodiment, a honeybee repellant may be a compound of formula XIVc:

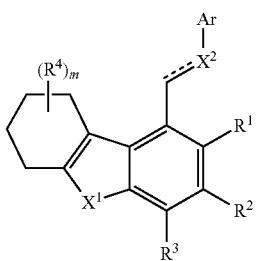

(XIVc)

wherein: $X^1$ and $X^2$ are each independently N, O or S; Ar is an optionally substituted 4-7-member aryl or an optionally substituted 4-7-member heteroaryl; $R^1$, $R^2$ and $R^3$ are each independently H, OH, OOH, O, OO, C(O), C(O)H, C(O)OH, OC(O)O, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, $C(O)OC_{2-6}$ alkynyl, halide, haloalkenyl, haloalkoxyl, haloalkyl, or halogen; $R^4$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), halide, halogen, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, or $C(O)OC_{2-6}$ alkynyl; and m is 0 to 5.

In aspects of this embodiment, a honeybee repellant of formula XIV disclosed herein an optionally substituted 3-iodo-1-[(1H-1,2,4-triazol-3-ylimino)methyl]-6,7,8,9-tetrahydrodibenzo[b,d]furan-2-ol.

In aspects of this embodiment, a honeybee repellant of formula XIV disclosed herein is

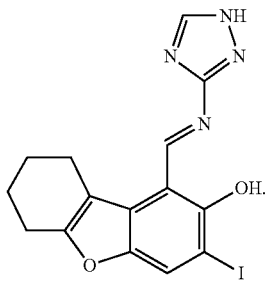

3-iodo-1-[(1H-1,2,4-triazol-3-ylimino)methyl]-6,7,8,9-tetrahydrodibenzo[b,d]furan-2-ol In aspects of this embodiment, a honeybee repellant is not 3-iodo-1-[(1H-1,2,4-triazol-3-ylimino)methyl]-6,7,8,9-tetrahydrodibenzo[b,d]furan-2-ol.

In another embodiment, a honeybee repellant may be a compound of formula XV:

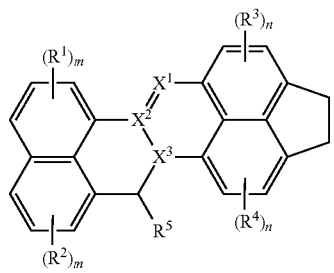

(XV)

wherein: $X^1$, $X^2$ and $X^3$ are each independently C, N, O or S; $R^1$, $R^2$, $R^3$ and $R^4$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, or $C(O)OC_{2-6}$ alkynyl; $R^5$ is H, OH, OOH, O, OO, C(O), C(O)H, C(O)OH, OC(O)O, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, $C(O)OC_{2-6}$ alkynyl, halide, haloalkenyl, haloalkoxyl, haloalkyl, or halogen; m is 0 to 4; and n is 0 to 3.

In another embodiment, a honeybee repellant may be a compound of formula XVa:

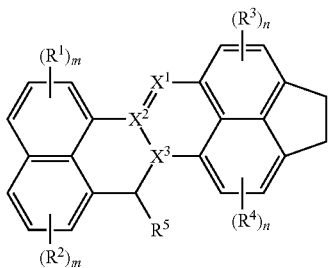

(XVa)

wherein: $X^1$, $X^2$ and $X^3$ are each independently C, N, or O; $R^1$, $R^2$, $R^3$ and $R^4$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, NH, NH$_2$, NHNH$_2$, NNN, NN, N(OH), NC, NCO, (N)C(O), NCS, (N)C(S), NO, N(O)$_2$, N(O)$_3$, halide, halogen, trihalomethanesulfonyl, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, or C(O)OC$_{2-6}$ alkynyl; $R^5$ is H, OH, OOH, O, OO, C(O), C(O)H, C(O)OH, OC(O)O, C$_{1-6}$ alkyl, OC$_{1-6}$ alkyl, C(O)$_2$C$_{1-6}$ alkyl, C(O)OC$_{1-6}$ alkyl, halide or halogen; m is 0 to 4; and n is 0 to 3.

In another embodiment, a honeybee repellant may be a compound of formula XVb:

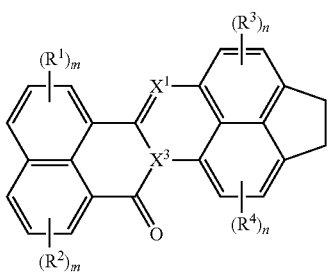

(XVb)

wherein: $X^1$ and $X^3$ are each independently C, N, O or S; $R^1$, $R^2$, $R^3$ and $R^4$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S) H, OC(S)N, SCN, CNS, (N)C(S), NH, NH$_2$, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, or C(O)OC$_{2-6}$ alkynyl; m is 0 to 4; and n is 0 to 3.

In another embodiment, a honeybee repellant may be a compound of formula XVc:

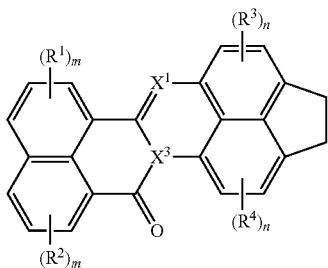

(XVc)

wherein: $X^1$ and $X^3$ are each independently N, O or S; $R^1$, $R^2$, $R^3$ and $R^4$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S) H, OC(S)N, SCN, CNS, (N)C(S), NH, NH$_2$, NHNH$_2$, NNN, NN, N(OH), NC, NCO, (N)C(O), halide, halogen, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, or C(O)OC$_{2-6}$ alkynyl; m is 0 to 4; and n is 0 to 3.

In aspects of this embodiment, a honeybee repellant of formula XV disclosed herein an optionally substituted 10-hydroxy-1,2-dihydro-12H-benzo[4,5]isoquino[2,1-a]cyclopenta[gh]perimidin-12-one.

In aspects of this embodiment, a honeybee repellant of formula XV disclosed herein is

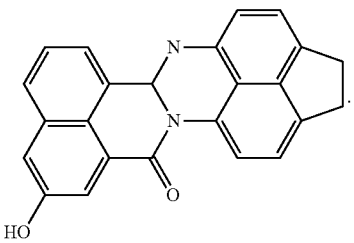

10-hydroxy-1,2-dihydro-12H-benzo[4,5]
isoquino[2,1-a]cyclopenta[gh]
perimidin-12-one In aspects of this embodiment, a honeybee repellant is not 10-hydroxy-1,2-dihydro-12H-benzo[4,5]isoquino[2,1-a]cyclopenta[gh]perimidin-12-one.

In another embodiment, a honeybee repellant may be a compound of formula XVI:

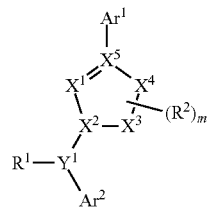

(XVI)

wherein: $X^1$, $X^2$, $X^3$, $X^4$ and $X^5$ are each independently C, N, O or S; $Y^1$ is OH, OOH, O, OO, OHC, C, C(O), C(O)H, C(O)OH, OC(O)O, C(O)NH$_2$, C(O)NC(O), C(NH)NH$_2$, C(O)N, OCN, NHC(O)O, CS, C(S)H, OC(S)N, SCN, CNS, (N)C(S), N, NH, NH$_2$, NHN, NHNH$_2$, NNN, NN, N(OH), NC, NCH, NHNCH, NCO, (N)C(O), NCS, (N)C(S), NO, N(O)$_2$, S, SH, S(O), S(O)$_2$, C$_{1-6}$ alkyl, C$_{2-6}$ alkenyl, C$_{2-6}$ alkynyl, CNH, CNHC$_{1-6}$ alkyl, CNHC$_{2-6}$ alkenyl, CNHC$_{2-6}$ alkynyl, C$_{1-6}$ alkylCNH, C$_{2-6}$ alkenylCNH, C$_{2-6}$ alkynylCNH, CN, CNC$_{1-6}$ alkyl, CNC$_{2-6}$ alkenyl, CNC$_{2-6}$ alkynyl, C$_{1-6}$ alkylCN, C$_{2-6}$ alkenylCN, C$_{2-6}$ alkynylCN, C(O)C=CNH, C(O)C=CNHC$_{1-6}$ alkyl, C(O)C=CNHC$_{1-6}$ alkenyl, C(O)C=CNHC$_{1-6}$ alkynyl, C$_{1-6}$ alkylC(O)C=CNH, C$_{1-6}$ alkenylC(O)C=CNH, C$_{1-6}$ alkynylC(O)C=CNH, OC$_{1-6}$ alkyl, OC$_{2-6}$ alkenyl, OC$_{2-6}$ alkynyl, C$_{1-6}$ alkylO, C$_{2-6}$ alkenylO, C$_{2-6}$ alkynylO, OHC$_{1-6}$ alkyl, OHC$_{2-6}$ alkenyl, OHC$_{2-6}$ alkynyl, C$_{1-6}$ alkylOH, C$_{2-6}$ alkenylOH, C$_{2-6}$ alkynylOH, OHC(O), OHC(O)C$_{1-6}$ alkyl, OHC(O)C$_{2-6}$ alkenyl, OHC(O)C$_{2-6}$ alkynyl, C$_{1-6}$ alkylOHC(O), C$_{2-6}$ alkenylOHC (O), C$_{2-6}$ alkynylOHC(O), OC(O)C$_{1-6}$ alkyl, OC(O)C$_{2-6}$ alkenyl, OC(O)C$_{2-6}$ alkynyl, C$_{1-6}$ alkylOC(O), C$_{2-6}$ alkenylOC(O), C$_{2-6}$ alkynylOC(O), C(O)$_2$C$_{1-6}$ alkyl, C(O)$_2$C$_{2-6}$ alkenyl, C(O)$_2$C$_{2-6}$ alkynyl, C$_{1-6}$ alkylC(O)$_2$, C$_{2-6}$ alkenylC(O)$_2$, C$_{2-6}$ alkynylC(O)$_2$, C(O)OC$_{1-6}$ alkyl, C(O)OC$_{2-6}$ alkenyl, C(O)OC$_{2-6}$ alkynyl, C$_{1-6}$ alkylC(O)O, C$_{2-6}$ alkenylC(O)O, C$_{2-6}$ alkynylC(O)O, CH$_2$C(O)C$_{1-6}$ alkyl, CH$_2$C(O)C$_{2-6}$ alkenyl, CH$_2$C(O)C$_{2-6}$ alkynyl, C$_{1-6}$ alkylCH$_2$C(O), C$_{2-6}$ alkenylCH$_2$C(O), C$_{2-6}$ alkynylCH$_2$C(O), CHC(O)C$_{1-6}$ alkyl, CHC(O)C$_{2-6}$ alkenyl, CHC(O)C$_{2-6}$ alkynyl, C$_{1-6}$ alkylCHC(O), C$_{2-6}$ alkenylCHC(O), C$_{2-6}$ alkynylCHC(O), CHN, CHNC$_{1-6}$ alkyl, CHNC$_{2-6}$ alkenyl, CHNC$_{2-6}$ alkynyl, C$_{1-6}$ alkylCHN, C$_{2-6}$ alkenylCHN, C$_{2-6}$ alkynylCHN, CHNNH, CHNNHC$_{1-6}$ alkyl, CHNNHC$_{2-6}$ alkenyl, CHNNHC$_{2-6}$ alkynyl, C$_{1-6}$ alkylCHNNH, C$_{2-6}$ alkenylCHNNH, C$_{2-6}$ alkynylCHNNH, NHNC$_{1-6}$ alkyl, NHNC$_{2-6}$ alkenyl, NHNC$_{2-6}$ alkynyl, C$_{1-6}$ alkylNHN, C$_{2-6}$ alkenylNHN, C$_{2-6}$ alkynylNHN, NC$_{1-6}$ alkyl, NC$_{2-6}$ alkenyl, NC$_{2-6}$ alkynyl, C$_{1-6}$ alkylNC, C$_{2-6}$ alkenylNC, C$_{2-6}$ alkynylNC, NHC$_{1-6}$ alkyl, NHC$_{2-6}$ alkenyl, NHC$_{2-6}$ alkynyl, C$_{1-6}$ alkylNH, C$_{2-6}$ alkenylNH, C$_{2-6}$ alkynylNH, NHC(O), NHC(O)C$_{1-6}$ alkyl, NHC(O)C$_{2-6}$ alkenyl, NHC(O)C$_{2-6}$ alkynyl, C$_{1-6}$ alkylNHC(O), C$_{2-6}$ alkenylNHC(O), C$_{2-6}$ alkynylNHC(O), NC(O)C$_{1-6}$ alkyl, NC(O)C$_{2-6}$ alkenyl, NC(O)C$_{2-6}$ alkynyl, C$_{1-6}$ alkylNC(O), C$_{2-6}$ alkeny NC(O), C$_{2-6}$ alkynylNC(O), C(O)NHC$_{1-6}$ alkyl, C(O)NHC$_{2-6}$ alkenyl, C(O)NHC$_{2-6}$ alkynyl, C$_{1-6}$ alkylC(O)NH, C$_{2-6}$ alkenylC(O)NH, C$_{2-6}$ alkynyl C(O)NH, C(O)NC$_{1-6}$ alkyl, C(O)NC$_{2-6}$ alkenyl, or C(O)NC$_{2-6}$ alkynyl, C$_{1-6}$ alkylC(O)N, C$_{2-6}$ alkenylC(O)N, or C$_{2-6}$ alkynyl C(O)N; Ar$^1$ and Ar$^2$ are each independently an optionally substituted 4-7-member aryl, an optionally substituted 4-7-member heteroaryl, an optionally substituted 4-7-member cycloalkyl, or an optionally substituted 4-7-member heterocycloalkyl; R$^1$ is H, OH, OOH, O, OO, C(O), C(O)H, C(O)OH, OC(O)O, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, C(O)OC$_{2-6}$ alkynyl, halide, haloalkenyl, haloalkoxyl, haloalkyl, or halogen; R$^2$ is independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, CS, C(S)H, OC(S)N, SCN, CNS, (N)C(S), NH, NH$_2$, NHN, NHNH$_2$, NNN, NN, N(OH), NC, NCO, (N)C(O), NCS, (N)C(S), NO, N(O)$_2$, N(O)$_3$, SH, S(O), S(O)$_2$, S(O)$_3$, S(O)$_2$N, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, C$_{1-6}$ alkyl, C$_{2-6}$ alkenyl, C$_{2-6}$ alkynyl, OC$_{1-6}$ alkyl, OC$_{2-6}$ alkenyl, OC$_{2-6}$ alkynyl, C(O)$_2$C$_{1-6}$ alkyl, C(O)$_2$C$_{2-6}$ alkenyl, C(O)$_2$C$_{2-6}$ alkynyl, C(O)OC$_{1-6}$ alkyl, C(O)OC$_{2-6}$ alkenyl, or C(O)OC$_{2-6}$ alkynyl; and m is 0 to 3.

In another embodiment, a honeybee repellant may be a compound of formula XVIa:

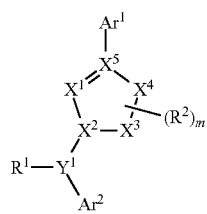

(XVIa)

wherein: X$^1$, X$^2$, X$^3$, X$^4$ and X$^5$ are each independently C, N, or O; Y$^1$ is OH, OOH, O, OO, OHC, C, C(O), C(O)H, C(O)OH, OC(O)O, C(O)NH$_2$, C(O)NC(O), C(NH)NH$_2$, C(O)N, OCN, NHC(O)O, CS, C(S)H, OC(S)N, SCN, CNS, (N)C(S), N, NH, NH$_2$, NHN, NHNH$_2$, NNN, NN, N(OH), NC, NCH, NHNCH, NCO, (N)C(O), NCS, (N)C(S), NO, N(O)$_2$, S, SH, S(O), S(O)$_2$, C$_{1-6}$ alkyl, CNH, CNHC$_{1-6}$ alkyl, C$_{1-6}$ alkylCNH, CN, CNC$_{1-6}$ alkyl, C$_{1-6}$ alkylCN, C(O)C=CNH, C(O)C=CNHC$_{1-6}$ alkyl, C$_{1-6}$ alkylC(O)C=CNH, OC$_{1-6}$ alkyl, C$_{1-6}$ alkylO, OHC$_{1-6}$ alkyl, C$_{1-6}$ alkylOH, OHC(O), OHC(O)C$_{1-6}$ alkyl, C$_{1-6}$ alkylOHC(O), OC(O)C$_{1-6}$ alkyl, C$_{1-6}$ alkylOC(O), C(O)$_2$C$_{1-6}$ alkyl, C$_{1-6}$ alkylC(O)$_2$, C(O)OC$_{1-6}$ alkyl, C$_{1-6}$ alkylC(O)O, CH$_2$C(O)C$_{1-6}$ alkyl, C$_{1-6}$ alkylCH$_2$C(O), CHC(O)C$_{1-6}$ alkyl, C$_{1-6}$ alkylCHC(O), CHN, CHNC$_{1-6}$ alkyl, C$_{1-6}$ alkylCHN, CHNNH, CHNNHC$_{1-6}$ alkyl, C$_{1-6}$ alkylCHNNH, NHNC$_{1-6}$ alkyl, C$_{1-6}$ alkylNHN, NC$_{1-6}$ alkyl, C$_{1-6}$ alkylNC, NHC$_{1-6}$ alkyl, C$_{1-6}$ alkylNH, NHC(O), NHC(O)C$_{1-6}$ alkyl, C$_{1-6}$ alkylNHC(O), NC(O)C$_{1-6}$ alkyl, C$_{1-6}$ alkylNC(O), C(O)NHC$_{1-6}$ alkyl, C$_{1-6}$ alkylC(O)NH, C(O)NC$_{1-6}$ alkyl, or C$_{1-6}$ alkylC(O)N; Ar$^1$ and Ar$^2$ are each independently an optionally substituted 4-7-member aryl or an optionally substituted 4-7-member heteroaryl; R$^1$ is H, OH, OOH, O, OO, C(O), C(O)H, C(O)OH, OC(O)O, C$_{1-6}$ alkyl, OC$_{1-6}$ alkyl, C(O)$_2$C$_{1-6}$ alkyl, C(O)OC$_{1-6}$ alkyl, halide, or halogen; R$^2$ is independently H, OH, OOH, O, OO, C(O), C(O)H, C(O) OH, OC(O)O, C(O)NH$_2$, C(O)NC(O), C(NH)NH$_2$, CN, CNH, C(O)N, OCN, NHC(O)O, NH, NH$_2$, NHNH$_2$, NNN, NN, N(OH), NC, NCO, (N)C(O), NCS, (N)C(S), NO, N(O)$_2$, N(O)$_3$, halide, haloalkyl, halogen, C$_{1-6}$ alkyl, OC$_{1-6}$ alkyl, C(O)$_2$C$_{1-6}$ alkyl or C(O)OC$_{1-6}$ alkyl; and m is 0 to 3.

In another embodiment, a honeybee repellant may be a compound of formula XVIb:

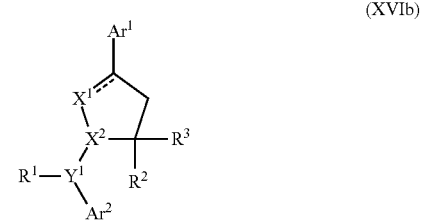

(XVIb)

wherein: X$^1$ and X$^2$ are each independently C, N, O or S; Y$^1$ is OH, OOH, O, OO, OHC, C, C(O), C(O)H, C(O)OH, OC(O)O, C(O)NH$_2$, C(O)NC(O), C(NH)NH$_2$, C(O)N, OCN, NHC(O)O, CS, C(S)H, OC(S)N, SCN, CNS, (N)C(S), N, NH, NH$_2$, NHN, NHNH$_2$, NNN, NN, N(OH), NC, NCH, NHNCH, NCO, (N)C(O), NCS, (N)C(S), NO, N(O)$_2$, S, SH, S(O), S(O)$_2$, C$_{1-6}$ alkyl, C$_{2-6}$ alkenyl, C$_{2-6}$ alkynyl, CNH, CNHC$_{1-6}$ alkyl, CNHC$_{2-6}$ alkenyl, CNHC$_{2-6}$ alkynyl, C$_{1-6}$ alkylCNH, C$_{2-6}$ alkenylCNH, C$_{2-6}$ alkynylCNH, CN, CNC$_{1-6}$ alkyl, CNC$_{2-6}$ alkenyl, CNC$_{2-6}$ alkynyl, C$_{1-6}$ alkylCN, C$_{2-6}$ alkenylCN, C$_{2-6}$ alkynylCN, C(O)C=CNH, C(O)C=CNHC$_{1-6}$ alkyl, C(O)C=CNHC$_{1-6}$ alkenyl, C(O)C=CNHC$_{1-6}$ alkynyl, C$_{1-6}$ alkylC(O)C=CNH, C$_{1-6}$ alkenylC(O)C=CNH, C$_{1-6}$ alkynylC(O)C=CNH, OC$_{1-6}$ alkyl, OC$_{2-6}$ alkenyl, OC$_{2-6}$ alkynyl, C$_{1-6}$ alkylO, C$_{2-6}$ alkenylO, C$_{2-6}$ alkynylO, OHC$_{1-6}$ alkyl, OHC$_{2-6}$ alkenyl, OHC$_{2-6}$ alkynyl, C$_{1-6}$ alkylOH, C$_{2-6}$ alkenylOH, C$_{2-6}$ alkynylOH, OHC(O), OHC(O)C$_{1-6}$ alkyl, OHC(O)C$_{2-6}$ alkenyl, OHC(O)C$_{2-6}$ alkynyl, C$_{1-6}$ alkylOHC(O), C$_{2-6}$ alkenylOHC(O), C$_{2-6}$ alkynylOHC(O), OC(O)C$_{1-6}$ alkyl, OC(O)C$_{2-6}$ alkenyl, OC(O)C$_{2-6}$ alkynyl, C$_{1-6}$ alkylOC(O), C$_{2-6}$ alkenylOC(O), C$_{2-6}$ alkynylOC(O), C(O)$_2$C$_{1-6}$ alkyl, C(O)$_2$C$_{2-6}$ alkenyl, C(O)$_2$C$_{2-6}$ alkynyl, C$_{1-6}$ alkylC(O)$_2$, C$_{2-6}$ alkenylC(O)$_2$, C$_{2-6}$ alkynylC(O)$_2$, C(O)OC$_{1-6}$ alkyl, C(O)OC$_{2-6}$ alkenyl, C(O)OC$_{2-6}$ alkynyl, C$_{1-6}$ alkylC(O)O, C$_{2-6}$ alkenylC (O)O, $C_{2-6}$ alkynylC(O)O, $CH_2C(O)C_{1-6}$ alkyl, $CH_2C(O)$ $C_{2-6}$ alkenyl, $CH_2C(O)C_{2-6}$ alkynyl, $C_{1-6}$ alkyl$CH_2C(O)$, $C_{2-6}$ alkenyl$CH_2C(O)$, $C_{2-6}$ alkynyl$CH_2C(O)$, $CHC(O)C_{1-6}$ alkyl, $CHC(O)C_{2-6}$ alkenyl, $CHC(O)C_{2-6}$ alkynyl, $C_{1-6}$ alkylCHC(O), $C_{2-6}$ alkenylCHC(O), $C_{2-6}$ alkynylCHC(O), CHN, $CHNC_{1-6}$ alkyl, $CHNC_{2-6}$ alkenyl, $CHNC_{2-6}$ alkynyl, $C_{1-6}$ alkylCHN, $C_{2-6}$ alkenylCHN, $C_{2-6}$ alkynylCHN, CHNNH, $CHNNHC_{1-6}$ alkyl, $CHNNHC_{2-6}$ alkenyl, $CHNNHC_{2-6}$ alkynyl, $C_{1-6}$ alkylCHNNH, $C_{2-6}$ alkenylCHNNH, $C_{2-6}$ alkynylCHNNH, $NHNC_{1-6}$ alkyl, $NHNC_{2-6}$ alkenyl, $NHNC_{2-6}$alkynyl, $C_{1-6}$ alkylNHN, $C_{2-6}$ alkenylNHN, $C_{2-6}$ alkynylNHN, $NC_{1-6}$ alkyl, $NC_{2-6}$ alkenyl, $NC_{2-6}$ alkynyl, $C_{1-6}$ alkylNC, $C_{2-6}$ alkenylNC, $C_{2-6}$ alkynylNC, $NHC_{1-6}$ alkyl, $NHC_{2-6}$ alkenyl, $NHC_{2-6}$ alkynyl, $C_{1-6}$ alkylNH, $C_{2-6}$ alkenylNH, $C_{2-6}$ alkynylNH, NHC(O), $NHC(O)C_{1-6}$ alkyl, $NHC(O)C_{2-6}$ alkenyl, $NHC(O)C_{2-6}$ alkynyl, $C_{1-6}$ alkylNHC(O), $C_{2-6}$ alkenylNHC(O), $C_{2-6}$ alkynylNHC(O), $NC(O)C_{1-6}$ alkyl, $NC(O)C_{2-6}$ alkenyl, $NC(O)C_{2-6}$ alkynyl, $C_{1-6}$ alkylNC(O), $C_{2-6}$ alkeny NC(O), $C_{2-6}$ alkynylNC(O), $C(O)NHC_{1-6}$ alkyl, $C(O)NHC_{2-6}$ alkenyl, $C(O)NHC_{2-6}$ alkynyl, $C_{1-6}$ alkylC(O)NH, $C_{2-6}$ alkenylC(O)NH, $C_{2-6}$ alkynyl C(O)NH, $C(O)NC_{1-6}$ alkyl, $C(O)NC_{2-6}$ alkenyl, or $C(O)NC_{2-6}$ alkynyl, $C_{1-6}$ alkylC(O)N, $C_{2-6}$ alkenylC(O)N, or $C_{2-6}$ alkynyl C(O)N; $Ar^1$ and $Ar^2$ are each independently an optionally substituted 4-7-member aryl, an optionally substituted 4-7-member heteroaryl, an optionally substituted 4-7-member cycloalkyl, or an optionally substituted 4-7-member heterocycloalkyl; $R^1$ is H, OH, OOH, O, OO, C(O), C(O)H, C(O)OH, OC(O)O, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, $C(O)OC_{2-6}$ alkynyl, halide, haloalkenyl, haloalkoxyl, haloalkyl, or halogen; and $R^2$ and $R^3$ are each independently H, OH, OOH, O, OO, C(O), C(O)H, C(O)OH, OC(O)O, $C(O)NH_2$, C(O)NC(O), $C(NH)NH_2$, CN, CNH, C(O)N, OCN, NHC(O)O, CS, C(S)H, OC(S)N, SCN, CNS, (N)C(S), NH, $NH_2$, $NHNH_2$, NNN, NN, N(OH), NC, NCO, (N)C(O), NCS, (N)C(S), NO, $N(O)_2$, $N(O)_3$, SH, S(O), $S(O)_2$, $S(O)_3$, $S(O)_2N$, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, or $C(O)OC_{2-6}$ alkynyl.

In another embodiment, a honeybee repellant may be a compound of formula XVIc:

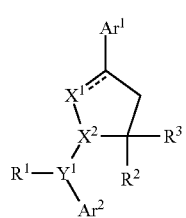

(XVIc)

wherein: $X^1$ and $X^2$ are each independently N, O or S; $Y^1$ is OH, OOH, O, OO, OHC, C, C(O), C(O)H, C(O)OH, OC(O)O, $C(O)NH_2$, C(O)NC(O), $C(NH)NH_2$, C(O)N, OCN, NHC(O)O, CS, C(S)H, OC(S)N, SCN, CNS, (N)C(S), N, NH, $NH_2$, NHN, $NHNH_2$, NNN, NN, N(OH), NC, NCH, NHNCH, NCO, (N)C(O), NCS, (N)C(S), NO, $N(O)_2$, S, SH, S(O), $S(O)_2$, $C_{1-6}$ alkyl, CNH, $CNHC_{1-6}$ alkyl, $C_{1-6}$ alkyl-CNH, CN, $CNC_{1-6}$ alkyl, $C_{1-6}$ alkylCN, C(O)C=CNH, C(O)C=$CNHC_{1-6}$ alkyl, $C_{1-6}$ alkylC(O)C=CNH, $OC_{1-6}$ alkyl, $C_{1-6}$ alkylO, $OHC_{1-6}$ alkyl, $C_{1-6}$ alkylOH, OHC(O), $OHC(O)C_{1-6}$ alkyl, $C_{1-6}$ alkylOHC(O), $OC(O)C_{1-6}$ alkyl, $C_{1-6}$ alkylOC(O), $C(O)_2C_{1-6}$ alkyl, $C_{1-6}$ alkyl$C(O)_2$, C(O)$OC_{1-6}$ alkyl, $C_{1-6}$ alkylC(O)O, $CH_2C(O)C_{1-6}$ alkyl, $C_{1-6}$ alkyl$CH_2C(O)$, $CHC(O)C_{1-6}$ alkyl, $C_{1-6}$ alkylCHC(O), CHN, $CHNC_{1-6}$ alkyl, $C_{1-6}$ alkylCHN, CHNNH, $CHN-NHC_{1-6}$ alkyl, $C_{1-6}$ alkylCHNNH, $NHNC_{1-6}$ alkyl, $C_{1-6}$ alkylNHN, $NC_{1-6}$ alkyl, $C_{1-6}$ alkylNC, $NHC_{1-6}$ alkyl, $C_{1-6}$ alkylNH, NHC(O), $NHC(O)C_{1-6}$ alkyl, $C_{1-6}$ alkylNHC(O), $NC(O)C_{1-6}$ alkyl, $C_{1-6}$ alkylNC(O), $C(O)NHC_{1-6}$ alkyl, $C_{1-6}$ alkylC(O)NH, $C(O)NC_{1-6}$ alkyl, or $C_{1-6}$ alkylC(O)N; $Ar^1$ and $Ar^2$ are each independently an optionally substituted 4-7-member aryl or an optionally substituted 4-7-member heteroaryl; $R^1$ is H, OH, OOH, O, OO, C(O), C(O)H, C(O)OH, OC(O)O, $C_{1-6}$ alkyl, $OC_{1-6}$ alkyl, $C(O)_2C_{1-6}$ alkyl, $C(O)OC_{1-6}$ alkyl, halide, or halogen; and $R^2$ and $R^3$ are each independently H, OH, OOH, O, OO, C(O), C(O)H, C(O) OH, OC(O)O, $C(O)NH_2$, C(O)NC(O), $C(NH)NH_2$, CN, CNH, C(O)N, OCN, NHC(O)O, NH, $NH_2$, $NHNH_2$, NNN, NN, N(OH), NC, NCO, (N)C(O), NCS, (N)C(S), NO, $N(O)_2$, $N(O)_3$, halide, haloalkyl, halogen, $C_{1-6}$ alkyl, $OC_{1-6}$ alkyl, $C(O)_2C_{1-6}$ alkyl or $C(O)OC_{1-6}$ alkyl.

In another embodiment, a honeybee repellant may be a compound of formula XVId:

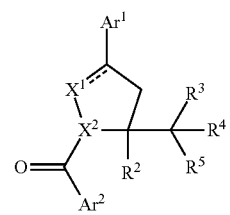

(XVId)

wherein: $X^1$ and $X^2$ are each independently C, N, O or S; $Ar^1$ and $Ar^2$ are each independently an optionally substituted 4-7-member aryl, an optionally substituted 4-7-member heteroaryl, an optionally substituted 4-7-member cycloalkyl, or an optionally substituted 4-7-member heterocycloalkyl; and $R^2$, $R^3$, $R^4$ and $R^5$ are each independently H, OH, OOH, O, OO, C(O), C(O)H, C(O)OH, OC(O)O, $C(O)NH_2$, C(O)NC(O), $C(NH)NH_2$, CN, CNH, C(O)N, OCN, NHC(O)O, CS, C(S)H, OC(S)N, SCN, CNS, (N)C(S), NH, $NH_2$, $NHNH_2$, NNN, NN, N(OH), NC, NCO, (N)C(O), NCS, (N)C(S), NO, $N(O)_2$, $N(O)_3$, SH, S(O), $S(O)_2$, $S(O)_3$, $S(O)_2N$, aminoalkyl, halide, haloalkenyl, haloalkoxyl, haloalkyl, halogen, trihalomethanesulfonyl, trihalomethanesulfonamido, trihalomethoxy, oxoalkyl, oxyalkyl, $C_{1-6}$ alkyl, $C_{2-6}$ alkenyl, $C_{2-6}$ alkynyl, $OC_{1-6}$ alkyl, $OC_{2-6}$ alkenyl, $OC_{2-6}$ alkynyl, $C(O)_2C_{1-6}$ alkyl, $C(O)_2C_{2-6}$ alkenyl, $C(O)_2C_{2-6}$ alkynyl, $C(O)OC_{1-6}$ alkyl, $C(O)OC_{2-6}$ alkenyl, or $C(O)OC_{2-6}$ alkynyl.

In another embodiment, a honeybee repellant may be a compound of formula XVIe:

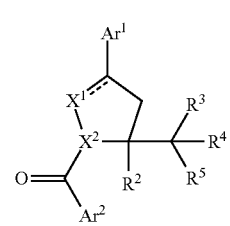

(XVIe)

wherein: $X^1$ and $X^2$ are each independently N, O or S; $Ar^1$ and $Ar^2$ are each independently an optionally substituted 4-7-member aryl or an optionally substituted 4-7-member heteroaryl; and $R^2$, $R^3$, $R^4$ and $R^5$ are each independently H, OH, OOH, O, OO, C(O), C(O)H, C(O)OH, OC(O)O, C(O)NH$_2$, C(O)NC(O), C(NH)NH$_2$, CN, CNH, C(O)N, OCN, NHC(O)O, NH, NH$_2$, NHNH$_2$, NNN, NN, N(OH), NC, NCO, (N)C(O), halide, haloalkenyl, haloalkoxyl, haloalkyl, halogen, $C_{1-6}$ alkyl, $OC_{1-6}$ alkyl, $C(O)_2C_{1-6}$ alkyl, or $C(O)OC_{1-6}$ alkyl.

In aspects of this embodiment, a honeybee repellant of formula XVI disclosed herein an optionally substituted 1-benzoyl-3-phenyl-5-(trifluoromethyl)-4,5-dihydro-1H-pyrazol-5-ol.

In aspects of this embodiment, a honeybee repellant of formula XVI disclosed herein is

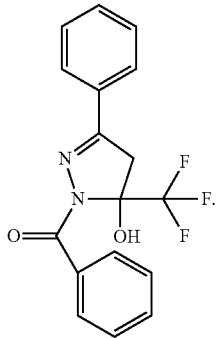

10-hydroxy-1,2-dihydro-12H-
benzo[4,5]isoquino[2,1-a]
cyclopenta[gh]perimidin-12-one In aspects of this embodiment, a honeybee repellant is not 1-benzoyl-3-phenyl-5-(trifluoromethyl)-4,5-dihydro-1H-pyrazol-5-ol.

In some embodiments, a honeybee repellent may be an optionally substituted 3-bromo-7,8-diethoxy-4-methyl-6-nitro-2H-chromen-2-one, an optionally substituted 4-hydroxy-3-[2-(4-hydroxphenyl)-2,3-dihydro-1,5-benzothiazepin-4-yl]-6-methyl-2H-pyran-2-one, an optionally substituted 6-(4-iodophenyl)imidazo[2,1-b][1,3]thiazole, an optionally substituted 4-(2-furylmethylene)-2-(4-methylphenyl)-1,3-oxazol-5(4H)-one, an optionally substituted 2-(3-bromophenyl)-2-oxoethyl benzoate, an optionally substituted 2-anilino-8-quinolinol, an optionally substituted (4-amino-3-nitrophenyl)(phenyl)methanone, an optionally substituted N-[2-(aminocarbonyl)phenyl]-2-naphthamide, an optionally substituted N,N'-bis(2-acetylphenyl)tetrahydro-2,5-thiophene dicarboxamide, an optionally substituted 3-iodo-N'-[(2-methyl-1H-indol-3-yl)methylene] benzohydrazide, an optionally substituted N'-(2-bromo-5-methoxybenzylidene)-2-(4-ethylphenoxy)acetohydrazide, an optionally substituted 9H-fluoren-9-one thiosemicarbazone, an optionally substituted 5-(4-nitrophenyl)-2,3,5,6-tetrahydrobenzo[a]phenanthridin-4(1H)-one, an optionally substituted N'-(4-bromo-5-methyl-2-oxo-1,2-dihydro-3H-indol-3-ylidene)spiro[2.3]hexane-1-carbohydrazide, an optionally substituted 2-[4-(allyloxy)-6-methyl-2-pyrimidinyl]phenol, an optionally substituted 2-[6-phenyl-2-(1-piperazinyl)-4-pyrimidinyl]phenol, an optionally substituted 4-{[(9-ethyl-9H-carbazol-3-yl)methylene]amino}benzamide, an optionally substituted ethyl 1-amino-3-isopropyl-3,4-dihydro-2-naphthalenecarboxylate, an optionally substituted ethyl [(4-oxo-3-phenyl-4,6-dihydro-3H-spiro[benzo[h]quinazoline-5,1'-cyclopentan]-2-yl)thio]acetate, an optionally substituted 1-(3,6-dichloro-9H-carbazol-9-yl)-3-(4-morpholinyl)-2-propanol, an optionally substituted 1-(3,6-dibromo-9H-carbazol-9-yl)-3-(4-morpholinyl)-2-propanol, an optionally substituted 3-[3-(3,6-dichloro-9H-carbazol-9-yl)-2-hydroxypropyl]-1,3-thiazolidine-2,4-dione, an optionally substituted 2-(benzoylamino)-N-(4-chlorophenyl)benzamide, an optionally substituted 1-(1-adamantyl)-N-mesityl-2-piperidine carboxamide hydrochloride, an optionally substituted 1-benzyl-4-(4-methoxy-3-methylbenzyl) piperazine, an optionally substituted 1-(4-methoxy-2,3-dimethylbenzyl)-4-(3-phenyl-2-propen-1-yl)piperazine, an optionally substituted 1-phenyl-1-propanone N-(3-methylphenyl)thiosemicarbazone, an optionally substituted 4-[(2-chloro-5-nitrobenzylidene) amino]phenol, an optionally substituted N-(4-nitrophenyl)-1H-indol-3-amine, an optionally substituted 4-(1H-pyrrol-1-yl)-5,6,7,8-tetrahydro[1]benzothieno[2,3-d]pyrimidine, an optionally substituted 2,2,4-trimethyl-1,2-dihydro-6-quinolinyl 3-methoxybenzoate, an optionally substituted 7-(diethylamino)-4-methyl-3-nitro-2H-chromen-2-one, an optionally substituted (4-bromo-3-chlorophenyl)(4-ethoxybenzylidene)amine, an optionally substituted 3-{[(9-ethyl-9H-carbazol-3-yl)methylene]amino}benzamide, an optionally substituted N~1~-(9-anthrylmethylene)-1H-tetrazole-1,5-diamine, an optionally substituted N-phenyl-N'-[2-(phenylethynyl)phenyl]urea, an optionally substituted (9-anthrylmethylene)(3-nitrophenyl)amine, an optionally substituted 2,4-di-tert-butyl-6-[(methylimino)methyl]phenol, an optionally substituted N'-[(2-chlorobenzoyl)oxy]benzenecarboximidamide, an optionally substituted N-(3-chloro-2-methylphenyl)-2-naphthalenesulfonamide, an optionally substituted 2-[2-(3,5-dimethyl-1H-pyrazol-1-yl)-6-phenyl-4-pyrimidinyl]phenol, an optionally substituted 2-[4-(4-methoxy-2,5-dimethylbenzyl)-1-piperazinyl]ethanol, an optionally substituted 2-(benzylthio)-5-(2-chlorophenyl)-1,3,4-oxadiazole, an optionally substituted 2-[(4-bromobenzyl)thio]-5-phenyl-1,3,4-oxadiazole, an optionally substituted 3-chloro-2-phenyl-4H-chromen-4-one, an optionally substituted N-benzyl-2,5-dichloro-N-ethylbenzenesulfonamide, an optionally substituted 4-fluoro-N-{[(2-methoxyphenyl)amino]carbonothioyl}benzamide, an optionally substituted 3-[(4-chlorobenzoyl)amino]propyl 4-chlorobenzoate, an optionally substituted methyl 3-[(4-fluorobenzoyl)amino]-2-butenoate, an optionally substituted 1-(4-methoxyphenyl)-3-(1-naphthyl)-2-propen-1-one, an optionally substituted 6-{2-[5-(3-chlorophenyl)-2-furyl]vinyl}-4-(trifluoromethyl)-2(1H)-pyrimidinone, an optionally substituted 9-amino-7H-benzimidazo[2,1-a]benzo[de]isoquinolin-7-one, an optionally substituted N-benzyl-2-phenyl-N-(3-pyridinylmethyl) ethanamine, an optionally substituted (3,4-difluorophenyl)[3-(4-methoxyphenyl)-1-methylpropyl]amine, an optionally substituted 1-(4-chlorophenyl)-3-(2-hydroxyphenyl)-1,3-propanedione, an optionally substituted N-(2-methylphenyl)-9-oxo-9H-fluorene-1-carboxamide, an optionally substituted N-[2-(4-chlorophenoxy)ethyl]-5-(3-methyl-1-piperazinyl)-2-nitroaniline, an optionally substituted 2-({[4-(benzylamino)phenyl]imino}methyl)-4-bromophenol, an optionally substituted 3-methyl-1-phenyl-1H-pyrazole-4,5-dione 4-[(3-hydroxyphenyl)hydrazone], an optionally substituted ethyl methyl 4-(4-bromophenyl)-2,6-dimethyl-1,4-dihydro-3,5-pyridinedicarboxylate, an optionally substituted benzyl 2-methyl-4-(4-methylphenyl)-5-oxo-1,4,5,6,7,8-hexahydro-3-quinolinecarboxylate, an optionally substituted 2-cyclohexyl-1H-naphtho[2,3-g]indazole-3,6,11(2H)-trione, an optionally substituted 2-phenoxyethyl 4-(3-fluorophenyl)-6-methyl-2- oxo-1,2,3,4-tetrahydro-5-pyrimidinecarboxylate, an optionally substituted 1,3-naphthalenediyl bis(2-methylpropanoate), an optionally substituted 7-methyl-3-(4-methylbenzoyl)-4H-chromen-4-one, an optionally substituted 2-[2-(2-aminophenyl)vinyl]-5,7-dimethyl-8-quinolinol, an optionally substituted 2,6-diphenyl-4H-1,3-dioxin-4-one, an optionally substituted 3-allyl-5-(2-hydroxy-3-nitrobenzylidene)-2-thioxo-1,3-thiazolidin-4-one, an optionally substituted 3,5-diphenyl-1-(trifluoroacetyl)-4,5-dihydro-1H-pyrazole, an optionally substituted 5-(2-chloro-5-nitrobenzylidene)-2-[(2-chlorophenyl)imino]-1,3-thiazolidin-4-one, an optionally substituted 2,6-di-tert-butylbenzo-1,4-quinone 4-thiosemicarbazone, an optionally substituted 2-ethyl-1-[(7-methyl-2-naphthyl)sulfonyl]piperidine, an optionally substituted 5-benzyl-3-bromo-2-hydroxybenzaldehyde, an optionally substituted 3-[5-(2-nitrophenyl)-2-furyl]-1-phenyl-2-propen-1-one, an optionally substituted 2-(1,3-benzothiazol-2-ylthio)-1-(3-nitrophenyl)ethanone, an optionally substituted isonicotinaldehyde diphenylhydrazone, an optionally substituted N'-(2-hydroxy-3-methoxybenzylidene)-2-[(2-methylphenyl)amino]acetohydrazide (non-preferred name), an optionally substituted 5-(1,3-benzodioxol-5-ylmethylene)-3-(1,5-dimethyl-3-oxo-2-phenyl-2,3-dihydro-1H-pyrazol-4-yl)-2-thioxo-1,3-thiazolidin-4-one, an optionally substituted N'-{[5-(2,3-dichlorophenyl)-2-furyl]methylene}isonicotinohydrazide, an optionally substituted 1-[3-(3,6-dibromo-9H-carbazol-9-yl)-2-hydroxypropyl]-2,5-pyrrolidinedione, an optionally substituted N'-{[5-(3-chloro-4-methoxyphenyl)-2-furyl]methylene}-2-pyridinecarbohydrazide, an optionally substituted N'-{[5-(4-bromophenyl)-2-furyl]methylene}-2-[(4-methylphenyl)amino]acetohydrazide, an optionally substituted 2-[(1-bromo-2-naphthyl)oxy]-N'-(2-hydroxy-5-methoxybenzylidene)butanohydrazide, an optionally substituted 1-[3-(3,6-dichloro-9H-carbazol-9-yl)-2-hydroxypropyl]-2,5-pyrrolidinedione, an optionally substituted N-(4-chloro-2,5-dimethoxyphenyl)-2-phenoxybutanamide, an optionally substituted N-[2-(aminocarbonyl) phenyl]-3-chloro-1-benzothiophene-2-carboxamide, an optionally substituted N-(2-furylmethyl)-4-hydroxy-1-(3-methylbutyl)-2-oxo-1,2-dihydro-3-quinolinecarboxamide, an optionally substituted methyl 5-{[(4-bromophenyl)amino]sulfonyl}-2-chlorobenzoate, an optionally substituted 3-allyl-5-{3-[(4-nitrobenzyl)oxy]benzylidene}-2-thioxo-1,3-thiazolidin-4-one, an optionally substituted 2-(2-fluorobenzylidene)-6-methoxy-3,4-dihydro-1(2H)-naphthalenone, an optionally substituted 2-(ethylthio)ethyl 4-(2-chlorophenyl)-6-methyl-2-oxo-1,2,3,4-tetrahydro-5-pyrimidinecarboxylate, an optionally substituted 2-{3-[4-(9H-fluoren-9-yl)-1-piperazinyl]-3-oxopropyl}-1H-isoindole-1,3(2H)-dione, an optionally substituted 3-(5-bromo-2-methoxyphenyl)-1-(3,4-dimethoxyphenyl)-2-propen-1-one, an optionally substituted ethyl 4-{4-[4-(4-morpholinyl) benzylidene]-3,5-dioxo-1-pyrazolidinyl}benzoate, an optionally substituted 3-methyl-6-(1-piperidinyl)-3H-naphtho[1,2,3-de]quinoline-2,7-dione, an optionally substituted 3,4-dimethylphenyl 2-chlorobenzoate, an optionally substituted spiro[cyclopentane-1,6'-isoquino[1,2-b]quinazolin]-8'(5'H)-one, an optionally substituted 1-benzoyl-5-(2-hydroxyphenyl)-3-(trifluoromethyl)-4,5-dihydro-1H-pyrazol-5-ol, an optionally substituted 1-(4-methoxybenzoyl)-3-phenyl-5-(trifluoromethyl)-4,5-dihydro-1H-pyrazol-5-ol, an optionally substituted 4-hydroxy-1-methyl-2-oxo-N-(1-phenylethyl)-1,2-dihydro-3-quinoline carboxamide, an optionally substituted 3-(4-chlorophenyl)-1-(3-pyridinylcarbonyl)-5-(trifluoromethyl)-4,5-dihydro-1H-pyrazol-5-ol, an optionally substituted 4-bromo-N'-[2-(trifluoroacetyl)-1-cyclopenten-1-yl]benzohydrazide, an optionally substituted 5-{2-[(2,4-dichlorobenzyl)oxy]-3-methoxybenzylidene}-2-imino-1,3-thiazolidin-4-one, an optionally substituted ethyl 2-{[(acetylamino) carbonothioyl]amino}-4-phenyl-3-thiophenecarboxylate, an optionally substituted N'-[1-(1,3-dioxo-2,3-dihydro-1H-inden-2-yl)ethylidene]-3-hydroxy-2-naphthohydrazide, an optionally substituted 9-methyl-2-phenyl-9H-imidazo[1,2-a]benzimidazole-3-carbaldehyde, an optionally substituted 2-(4-bromophenyl)-3-[(4-nitrophenyl)sulfonyl]-1,3-thiazolidine, an optionally substituted 9-amino-7H-benzimidazo[2,1-a]benzo[de]isoquinolin-7-one, an optionally substituted 1-(4-methoxyphenyl)-3-(1-methyl-1H-indol-3-yl)-2-propen-1-one, an optionally substituted N-methyl-N-[(6-nitro-1,3-benzodioxol-5-yl)methyl]-2-(2-pyridinyl)ethanamine, an optionally substituted 4-[(6-nitro-1,3-benzodioxol-5-yl)methyl]thiomorpholine, an optionally substituted 1,1'-(1,4-phenylene)bis[3-(1H-indol-3-yl)-2-propen-1-one], an optionally substituted 1-(4-biphenylyl)-3-(1H-indol-3-yl)-2-propen-1-one, or an optionally substituted 1-methyl-4-[(6-nitro-1,3-benzodioxol-5-yl)methyl]piperazine.

In some embodiments, a honeybee repellent is not 3-bromo-7,8-diethoxy-4-methyl-6-nitro-2H-chromen-2-one, 4-hydroxy-3-[2-(4-hydroxyphenyl)-2,3-dihydro-1,5-benzothiazepin-4-yl]-6-methyl-2H-pyran-2-one, 6-(4-iodophenyl)imidazo[2,1-b][1,3]thiazole, 4-(2-furylmethylene)-2-(4-methylphenyl)-1,3-oxazol-5(4H)-one, 2-(3-bromophenyl)-2-oxoethyl benzoate, 2-anilino-8-quinolinol, (4-amino-3-nitrophenyl)(phenyl)methanone, N-[2-(aminocarbonyl)phenyl]-2-naphthamide, N'-(2-bromo-5-methoxybenzylidene)-2-(4-ethylphenoxy)acetohydrazide, 9H-fluoren-9-one thiosemicarbazone, 5-(4-nitrophenyl)-2,3,5,6-tetrahydrobenzo[a]phenanthridin-4(1H)-one, N'-(4-bromo-5-methyl-2-oxo-1,2-dihydro-3H-indol-3-ylidene) spiro[2.3]hexane-1-carbohydrazide, 2-[4-(allyloxy)-6-methyl-2-pyrimidinyl]phenol, 2-[6-phenyl-2-(1-piperazinyl)-4-pyrimidinyl]phenol, 4-{[(9-ethyl-9H-carbazol-3-yl)methylene]amino}benzamide, ethyl 1-amino-3-isopropyl-3,4-dihydro-2-naphthalenecarboxylate, ethyl [(4-oxo-3-phenyl-4,6-dihydro-3H-spiro[benzo[h]quinazoline-5,1'-cyclopentan]-2-yl)thio]acetate, 1-(3,6-dichloro-9H-carbazol-9-yl)-3-(4-morpholinyl)-2-propanol, 1-(3,6-dibromo-9H-carbazol-9-yl)-3-(4-morpholinyl)-2-propanol, 3-[3-(3,6-dichloro-9H-carbazol-9-yl)-2-hydroxypropyl]-1,3-thiazolidine-2,4-dione, N-(3,4-dihydro-1 (2H)-quinolinylcarbonothioyl)-N-(4-chlorophenyl) benzamide, 2-(benzoylamino)-N-(4-chlorophenyl)benzamide, 1-(1-adamantyl)-N-mesityl-2-piperidinecarboxamide hydrochloride, 1-(4-methoxy-2,3-dimethylbenzyl)-4-(3-phenyl-2-propen-1-yl)piperazine, 1-phenyl-1-propanone N-(3-methylphenyl)thiosemicarbazone, N-(4-nitrophenyl)-1H-indol-3-amine, (3-amino-6-phenylthieno[2,3-b]pyridin-2-yl)(phenyl) methanone, 4-(1H-pyrrol-1-yl)-5,6,7,8-tetrahydro[1]benzothieno [2,3-d]pyrimidine, 4-[2-(4-nitrophenyl) vinyl]phenol, 2,2,4-trimethyl-1,2-dihydro-6-quinolinyl 3-methoxybenzoate, 7-(diethylamino)-4-methyl-3-nitro-2H-chromen-2-one, (4-bromo-3-chlorophenyl)(4-ethoxybenzylidene)amine, 4-[4-nitro-3-(2-phenoxyethoxy)phenyl] morpholine, 3-{[(9-ethyl-9H-carbazol-3-yl)methylene]amino}benzamide, N~1~-(9-anthrylmethylene)-1H-tetrazole-1,5-diamine, N-phenyl-N'-[2-(phenylethynyl)phenyl]urea, (9-anthrylmethylene)(3-nitrophenyl)amine, 2,4-di-tert-butyl-6-[(methylimino)methyl]phenol, N'-[(2-chlorobenzoyl)oxy]benzenecarboximidamide, N-(3-chloro-2-methylphenyl)-2-naphthalenesulfonamide, 2-[2-(3,5-dimethyl-1H-pyrazol-1-yl)-6-phenyl-4-pyrimidinyl]phenol, 2-[4-(4-methoxy-2,5-dimethylbenzyl)-1-piperazinyl]ethanol, 2-(benzylthio)-5-(2-chlorophenyl)-1,3,4-oxadiazole, 2-[(4-bromobenzyl)thio]-

5-phenyl-1,3,4-oxadiazole, 3-chloro-2-phenyl-4H-chromen-4-one, N-benzyl-2,5-dichloro-N-ethylbenzenesulfonamide, 4-fluoro-N-{[(2-methoxyphenyl)amino]carbonothioyl}benzamide, 3-[(4-chlorobenzoyl)amino]propyl 4-chlorobenzoate, methyl 3-[(4-fluorobenzoyl)amino]-2-butenoate, 1-(4-methoxyphenyl)-3-(1-naphthyl)-2-propen-1-one, 6-{2-[5-(3-chlorophenyl)-2-furyl]vinyl}-4-(trifluoromethyl)-2(1H)-pyrimidinone, 9-amino-7H-benzimidazo[2,1-a]benzo[de]isoquinolin-7-one, N-benzyl-2-phenyl-N-(3-pyridinylmethyl)ethanamine, (3,4-difluorophenyl)[3-(4-methoxyphenyl)-1-methylpropyl]amine, 1-(4-chlorophenyl)-3-(2-hydroxyphenyl)-1,3-propanedione, N-(2-methylphenyl)-9-oxo-9H-fluorene-1-carboxamide, N-[2-(4-chlorophenoxy)ethyl]-5-(3-methyl-1-piperazinyl)-2-nitroaniline, 2-({[4-(benzylamino)phenyl]imino}methyl)-4-bromophenol, 3-methyl-1-phenyl-1H-pyrazole-4,5-dione 4-[(3-hydroxyphenyl)hydrazone], ethyl methyl 4-(4-bromophenyl)-2,6-dimethyl-1,4-dihydro-3,5-pyridinedicarboxylate, benzyl 2-methyl-4-(4-methylphenyl)-5-oxo-1,4,5,6,7,8-hexahydro-3quinolinecarboxylate, 2-cyclohexyl-1H-naphtho[2,3-g]indazole-3,6,11(2H)-trione, 2-phenoxyethyl 4-(3-fluorophenyl)-6-methyl-2-oxo-1,2,3,4-tetrahydro-5-pyrimidinecarboxylate, 1,3-naphthalenediyl bis(2-methylpropanoate), 7-methyl-3-(4-methylbenzoyl)-4H-chromen-4-one, 2-[2-(2-aminophenyl)vinyl]-5,7-dimethyl-8-quinolinol, 2,6-diphenyl-4H-1,3-dioxin-4-one, 3-allyl-5-(2-hydroxy-3-nitrobenzylidene)-2-thioxo-1,3-thiazolidin-4-one, 3,5-diphenyl-1-(trifluoroacetyl)-4,5-dihydro-1H-pyrazole, 5-(2-chloro-5-nitrobenzylidene)-2-[(2-chlorophenyl)imino]-1,3-thiazolidin-4-one, 2,6-di-tert-butylbenzo-1,4-quinone 4-thiosemicarbazone, 2-ethyl-1-[(7-methyl-2-naphthyl)sulfonyl]piperidine, 5-benzyl-3-bromo-2-hydroxybenzaldehyde, 3-[5-(2-nitrophenyl)-2-furyl]-1-phenyl-2-propen-1-one, 2-(1,3-benzothiazol-2-ylthio)-1-(3-nitrophenyl)ethanone, isonicotinaldehyde diphenylhydrazone, N'-(2-hydroxy-3-methoxybenzylidene)-2-[(2-methylphenyl)amino]acetohydrazide (non-preferred name), 5-(1,3-benzodioxol-5-ylmethylene)-3-(1,5-dimethyl-3-oxo-2-phenyl-2,3-dihydro-1H-pyrazol-4-yl)-2-thioxo-1,3-thiazolidin-4-one, N'-{[5-(2,3-dichlorophenyl)-2-furyl]methylene}isonicotinohydrazide, 1-[3-(3,6-dibromo-9H-carbazol-9-yl)-2-hydroxypropyl]-2,5-pyrrolidinedione, N'-{[5-(3-chloro-4-methoxyphenyl)-2-furyl] methylene}-2-pyridinecarbohydrazide, N'-{[5-(4-bromophenyl)-2-furyl] methylene}-2-[(4-methylphenyl) amino]acetohydrazide, 2-[(1-bromo-2-naphthyl)oxy]-N'-(2-hydroxy-5-methoxybenzylidene) butanohydrazide, 1-[3-(3,6-dichloro-9H-carbazol-9-yl)-2-hydroxypropyl]-2,5-pyrrolidinedione, N-(4-chloro-2,5-dimethoxyphenyl)-2-phenoxybutanamide, N-[2-(aminocarbonyl)phenyl]-3-chloro-1-benzothiophene-2-carboxamide, N-(2-furylmethyl)-4-hydroxy-1-(3-methylbutyl)-2-oxo-1,2-dihydro-3-quinolinecarboxamide, methyl 5-{[(4-bromophenyl)amino]sulfonyl}-2-chlorobenzoate, 3-allyl-5-{3-[(4-nitrobenzyl) oxy]benzylidene}-2-thioxo-1,3-thiazolidin-4-one, N-[3-(1-piperidinylcarbonyl)-5,6,7,8-tetrahydro-4H-cyclohepta[b] thien-2-yl]benzamide, 2-(2-fluorobenzylidene)-6-methoxy-3,4-dihydro-1(2H)-naphthalenone, 2-(ethylthio)ethyl 4-(2-chlorophenyl)-6-methyl-2-oxo-1,2,3,4-tetrahydro-5-pyrimidinecarboxylate, 2-{3-[4-(9H-fluoren-9-yl)-1-piperazinyl]-3-oxopropyl}-1H-isoindole-1,3(2H)-dione, 3-(5-bromo-2-methoxyphenyl)-1-(3,4-dimethoxyphenyl)-2-propen-1-one, N-[(8-quinolinylamino)carbonothioyl]-2-thiophenecarboxamide, 1,2,3-trichloro-4-(isopropylamino) anthra-9,10-quinone, 3-methyl-6-(1-piperidinyl)-3H-naphtho[1,2,3-de]quinoline-2,7-dione, 3,4-dimethylphenyl 2-chlorobenzoate, spiro[cyclopentane-1,6'-isoquino[1,2-b]quinazolin]-8'(5'H)-one, 1-benzoyl-5-(2-hydroxyphenyl)-3-(trifluoromethyl)-4,5-dihydro-1H-pyrazol-5-ol, 1-(4-methoxybenzoyl)-3-phenyl-5-(trifluoromethyl)-4,5-dihydro-1H-pyrazol-5-ol, 4-hydroxy-1-methyl-2-oxo-N-(1-phenylethyl)-1,2-dihydro-3-quinolinecarboxamide, 3-(4-chlorophenyl)-1-(3-pyridinylcarbonyl)-5-(trifluoromethyl)-4,5-dihydro-1H-pyrazol-5-ol, 4-bromo-N'-[2-(trifluoroacetyl)-1-cyclopenten-1-yl]benzohydrazide, 5-{2-[(2,4-dichloro benzyl)oxy]-3-methoxybenzylidene}-2-imino-1,3-thiazolidin-4-one, ethyl 2-{[(acetylamino)carbonothioyl]amino}-4-phenyl-3-thiophenecarboxylate, N'-[1-(1,3-dioxo-2,3-dihydro-1H-inden-2-yl)ethylidene]-3-hydroxy-2-naphthohydrazide, 9-methyl-2-phenyl-9H-imidazo[1,2-a]benzimidazole-3-carbaldehyde, 2-(4-bromophenyl)-3-[(4-nitrophenyl)sulfonyl]-1,3-thiazolidine, 9-amino-7H-benzimidazo[2,1-a]benzo[de]isoquinolin-7-one, 1-(4-methoxyphenyl)-3-(1-methyl-1H-indol-3-yl)-2-propen-1-one, N-methyl-N-[(6-nitro-1,3-benzodioxol-5-yl)methyl]-2-(2-pyridinyl)ethanamine, 4-[(6-nitro-1,3-benzodioxol-5-yl) methyl] thiomorpholine, 1,1'-(1,4-phenylene)bis[3-(1H-indol-3-yl)-2-propen-1-one], 1-(4-biphenylyl)-3-(1H-indol-3-yl)-2-propen-1-one, 1-(1,3-benzodioxol-5-ylmethyl)-4-(4,5-dimethoxy-2-nitrobenzyl) piperazine, 1-methyl-4-[(6-nitro-1,3-benzodioxol-5-yl)methyl]piperazine, or any combination thereof.

Aspects of the present specification provide, in part, a composition comprising a honeybee repellent disclosed herein. A composition disclosed herein comprises a repellent compound disclosed herein and is useful in repelling honeybees from an individual and/or a location treated with the composition. As such, a composition disclosed herein is useful for any application that reduces bee-human interaction or a bee-location interaction. A composition may be administered to an individual or location alone, or in combination with other supplementary active ingredients, agents, or drugs.

A composition disclosed herein may comprise one or more honeybee repellents disclosed herein. In one embodiment, a composition disclosed herein may comprise only a single a honeybee repellent disclosed herein. In another embodiment, a composition disclosed herein may comprise a plurality of honeybee repellents disclosed herein. In aspects of this embodiment, a composition disclosed herein comprises at least two honeybee repellents, at least three honeybee repellents, at least four honeybee repellents, or at least five honeybee repellents. In other aspects of this embodiment, a composition disclosed herein comprises at most two honeybee repellents, at most three honeybee repellents, or at most four honeybee repellents. In yet other aspects of this embodiment, a composition disclosed herein comprises one to three honeybee repellents, two to four honeybee repellents, two to five honeybee repellents, three to five honeybee repellents, or two to three honeybee repellents.

In an embodiment, a composition disclosed herein includes a repellent of formula I, formula II, formula III, formula IV, formula V, formula VI, formula VII, formula VIII, formula IX, formula X, formula XI, formula XII, formula XIII, or any combination thereof.

In an embodiment, a composition disclosed herein has a honeybee repellency activity. In aspects of this embodiment, presence of a composition repels honeybees by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%, as compared to not having the composition present. In other aspects of this embodiment, presence of a composition repels honeybees by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%, as compared to not having the composition present.

In an embodiment, a composition disclosed herein reduces a honeybee interaction with a mammal or location. In aspects of this embodiment, a composition reduces honeybee interaction with a mammal or location by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In other aspects of this embodiment, a composition reduces honeybee interaction with a mammal or location by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a composition disclosed herein reduces an ability of a honeybee to obtain a meal from a plant. In aspects of this embodiment, a composition reduces an ability of a honeybee to obtain a meal from a plant by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In other aspects of this embodiment, a composition reduces an ability of a honeybee to obtain a meal from a plant by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A composition disclosed herein can take any of a variety of dosage forms including, without limitation, a liquid composition, such as, e.g., a solution, suspension, emulsion; a semi-solid composition, such as, e.g., a ointment, cream, balm, foam, gel, or salve or a solid composition, such as, e.g., lyophilizate, powder, granule, pellet, capsule; or any other dosage form suitable for applying a repellent compound disclosed herein to a mammal, plant, and/or location to be treated. In one embodiment, in liquid, semi-solid, and solid forms, an amount of a repellent compound disclosed herein typically is between about 0.0001% (w/v) to about 50% (w/v), about 0.001% (w/v) to about 10.0% (w/v), or about 0.01% (w/v) to about 1.0% (w/v). In another aspect embodiment, in liquid, semi-solid, and solid forms, an amount of a repellent compound disclosed herein typically is between about 0.001 µg/cm$^2$ to about 500 µg/cm$^2$, about 0.01 µg/cm$^2$ to about 100 µg/cm$^2$, or about 0.1 µg/cm$^2$ to about 10 µg/cm$^2$. In another aspect embodiment, in liquid, semi-solid, and solid forms, an amount of a repellent compound disclosed herein typically is between about 0.01 nmole/cm$^2$ to about 1000 nmole/cm$^2$, about 0.1 nmole/cm$^2$ to about 100 nmole/cm$^2$, or about 1 nmole/cm$^2$ to about 50 nmole/cm$^2$. In another embodiment, in liquid, semi-solid, and solid forms, an amount of a repellent compound disclosed herein is typically is between about 0.001 mg/L to about 500 mg/L, about 0.01 mg/L to about 100 mg/L, or about 0.1 mg/L to about 50 mg/L.

The amount of a honeybee repellent disclosed herein used in the compositions disclosed herein is an effective amount. As used herein, the term "effective amount" refers to an amount of a honeybee repellent or composition disclosed herein sufficient to repel or direct movement of honeybees to the source of repellent compound release.

In aspects of this embodiment, a composition comprises a honeybee repellent in an effective amount of, e.g., at least 0.0001%, at least 0.00025%, at least 0.0005%, at least 0.00075%, at least 0.001%, at least 0.0025%, at least 0.005%, at least 0.0075%, at least 0.01%, at least 0.025%, at least 0.05%, at least 0.075%, at least 0.1%, at least 0.25%, at least 0.5%, at least 0.75%, at least 1%, at least 2.5%, at least 5%, at least 7.5%, at least 10%, at least 25%, or at least 50%, by weight of a composition.

In other aspects of this embodiment, a composition comprises a honeybee repellent in an effective amount of between, e.g., about 0.0001% to about 0.001%, about 0.0001% to about 0.01%, about 0.0001% to about 0.1%, about 0.00025% to about 0.0025%, about 0.00025% to about 0.025%, about 0.00025% to about 0.25%, about 0.0005% to about 0.005%, about 0.0005% to about 0.05%, about 0.0005% to about 0.75%, about 0.00075% to about 0.0075%, about 0.00075% to about 0.075%, about 0.00075% to about 0.75%, about 0.001% to about 0.01%, about 0.001% to about 0.1%, about 0.001% to about 1%, about 0.0025% to about 0.025%, about 0.0025% to about 0.25%, about 0.0025% to about 2.5%, about 0.005% to about 0.05%, about 0.005% to about 0.5%, about 0.005% to about 5%, about 0.0075% to about 0.075%, about 0.0075% to about 0.75%, about 0.0075% to about 7.5%, about 0.01% to about 0.1%, about 0.01% to about 1%, about 0.01% to about 10%, about 0.025% to about 0.25%, about 0.025% to about 2.5%, about 0.025% to about 25%, about 0.05% to about 0.5%, about 0.05% to about 5%, about 0.05% to about 50%, about 0.075% to about 0.75%, about 0.075% to about 7.5%, or about 0.075% to about 75%, by weight of a composition. In yet other aspects of this embodiment, a composition comprises a honeybee repellent in an effective amount of between, e.g., about 0.005% to about 0.015%, about 0.0025% to about 0.025%, or about 0.006% to about 0.016%, by weight of a composition.

A composition disclosed herein may optionally comprise one or more additional compounds providing an additional beneficial or otherwise useful effect. Such compounds include, without limitation, an adhesive, a solvent, a wetting agent, an emulsifying agent, a carrier, a diluent, a dispersing agent an insecticide, a pesticide, a fungicide, a fertilizer of a micronutrient or macronutrient nature, a herbicide, a feeding inhibitor, an insect molting inhibitor, an insect mating inhibitor, an insect maturation inhibitor, a nematocide, a nutritional or horticultural supplement, a larvicide, a seed, or any combination thereof. Such compounds are known to a person of ordinary skill in the art.

In one aspect of this embodiment, a composition disclosed herein may optionally comprise an insecticide. In another aspect of this embodiment, a composition disclosed herein may optionally comprise a plurality of insecticides. Insecticides include oils, emulsifers, detergents, soaps, microorganisms like fungi, bacteria, bacteriophages, and viruses, abrasives, toxins, and poisons. Non-limiting examples of an insecticide include a organochlorine, such as, e.g., Aldrin, Chlordane, Chlordecone, DDT, Dieldrin, Endosulfan, Endrin, Heptachlor, Hexachlorobenzene, Lindane (gamma-hexachlorocyclohexane), Methoxychlor, Mirex, Pentachlorophenol, and TDE; an organophosphate, such as, e.g., Acephate, Azinphos-methyl, Bensulide, Chlorethoxyfos, Chlorpyrifos, Chlorpyriphos-methyl, Diazinon, Dichlorvos (DDVP), Dicrotophos, Dimethoate, Disulfoton, Ethoprop, Fenamiphos, Fenitrothion, Fenthion, Fosthiazate, Malathion, Methamidophos, Methidathion, Mevinphos, Monocrotophos, Naled, Omethoate, Oxydemeton-methyl, Parathion, Parathion-methyl, Phorate, Phosalone, Phosmet, Phostebupirim, Phoxim, Pirimiphos-methyl, Profenofos, Terbufos, Tetrachlorvinphos, Tribufos, and Trichlorfon; a carbamate, such as, e.g., Aldicarb, Bendiocarb, Carbofuran, Carbaryl, Dioxacarb, Fenobucarb, Fenoxycarb, Isoprocarb, Methomyl, and 2-(1-Methylpropyl)phenyl methylcarbamate; a pyrethroid, such as, e.g., Allethrin, Bifenthrin, Cyhalothrin, A-Cyhalothrin, Cypermethrin, Cyfluthrin, Deltamethrin, Etofenprox, Fenvalerate, Permethrin, Phenothrin, Prallethrin, Resmethrin, Tetramethrin, Tralomethrin, and Transfluthrin; a neonicotinoid, such as, e.g., Acetamiprid, Clothianidin, Imidacloprid, Nitenpyram, Nithiazine, Thiacloprid, and Thiamethoxam; and a spinosad, such as, e.g., spinosyn A and spinosyn B.

The present specification provides, in part, a composition comprising a repellent compound or a composition providing an additional beneficial or otherwise useful effect that is coated, encapsulated or otherwise covered with a honeybee repellent or a composition comprising a honeybee repellent disclosed herein. Additionally, the present specification provides, in part, a composition comprising a honeybee repellent or a composition comprising a honeybee repellent disclosed herein that is coated, encapsulated or otherwise covered with another compound or composition providing an additional beneficial or otherwise useful effect. The compositions disclosed herein are formulated to repel honeybees from a location where the compositions were intentionally or unintentionally deposited and at the same time provide an additional beneficial or otherwise useful effect.

When used to coat another substance, a honeybee repellent or composition comprising a honeybee repellent disclosed herein, or a compound or composition providing an additional beneficial or otherwise useful effect disclosed herein are formulated in a manner that will allow the repellent, compound, or compositions thereof to adhere to the other substance. Typically, a repellent, a compound, or a composition thereof are mixed with a coating material and processed into a formulation such as, e.g., a solid, a gel, a liquid, a suspension in aqueous or non-aqueous medium, an emulsion, or a foam. Such coating materials and adhering methods are known to a person of ordinary skill in the art.

For example, a honeybee repellent can be mixed with a wax and the resulting mixture is then adhered to a compound providing an additional beneficial or otherwise useful effect in a manner that ensures the compound is coated, encapsulated or otherwise covered by the mixture. In one aspect, a honeybee repellent can be mixed with a wax and the resulting mixture is then adhered to a seed in a manner that ensures the seed is coated, encapsulated or otherwise covered by the mixture. In another aspect, a honeybee repellent can be mixed with a wax and the resulting mixture is then adhered to an insecticide in a manner that ensures the insecticide is coated, encapsulated or otherwise covered by the mixture. In yet another aspect, a honeybee repellent and an insecticide can be mixed with a wax and the resulting mixture is then adhered to a seed in a manner that ensures the seed is coated, encapsulated or otherwise covered by the mixture.

In another embodiment, an appropriate amount of a honeybee repellent disclosed herein can be dissolved into an appropriate compatible solvent and the resulting mixture is then adhered to a compound providing an additional beneficial or otherwise useful effect in a manner that ensures the compound is coated, encapsulated or otherwise covered by the mixture. The solvent employed is typically a volatile solvent (i.e., having a boiling point of about 100° C. or less) that will evaporate over a periodof time. In one aspect, a honeybee repellent can be mixed with a solvent and the resulting mixture is then adhered to a seed in a manner that ensures the seed is coated, encapsulated or otherwise covered by the mixture. In another aspect, a honeybee repellent can be mixed with a solvent and the resulting mixture is then adhered to an insecticide in a manner that ensures the insecticide is coated, encapsulated or otherwise covered by the mixture. In yet another aspect, a honeybee repellent and an insecticide can be mixed with a solvent and the resulting mixture is then adhered to a seed in a manner that ensures the seed is coated, encapsulated or otherwise covered by the mixture.

In one aspect of this embodiment, one or more insecticides, pesticides, fungicides, fertilizers of a micronutrient or macronutrient nature, herbicides, feeding inhibitors, insect molting, insect mating, insect maturation inhibitors, nematocides, nutritional or horticultural supplements, larvicides, seeds, and any combination thereof is coated, encapsulated or otherwise covered with one or more honeybee repellents or compositions comprising a honeybee repellent disclosed herein.

In another aspect of this embodiment, a honeybee repellent or compositions disclosed herein is coated, encapsulated or otherwise covered with one or more insecticides, pesticides, fungicides, fertilizers of a micronutrient or macronutrient nature, herbicides, feeding inhibitors, insect molting, insect mating, insect maturation inhibitors, nematocides, nutritional or horticultural supplements, larvicides, seeds, and any combination thereof.

In yet another aspect of this embodiment, seeds are coated, encapsulated or otherwise covered with one or more honeybee repellents or compositions comprising a honeybee repellent disclosed herein. These compositions are formulated to repel honeybees from the seed, and thus from a field, yard, pot, area, or body of water onto which the seeds were intentionally or unintentionally present.

In still another aspect of this embodiment, seeds are coated, encapsulated or otherwise covered with one or more honeybee repellents or compositions comprising a honeybee repellent disclosed herein and one or more insecticides, pesticides, fungicides, fertilizers of a micronutrient or macronutrient nature, herbicides, feeding inhibitors, insect molting, insect mating, insect maturation inhibitors, nematocides, nutritional or horticultural supplements, or larvicides. These compositions are formulated to repel honeybees from the seed, and thus from a field, yard, pot, area, or body of water onto which the seeds were be intentionally or unintentionally present as well as provide an additional beneficial or otherwise useful effect.

In another embodiment, a honeybee repellent or composition disclosed herein is incorporated into a device. As used herein, the term "device" refers to any device designed to house and/or shelter, a honeybee repellent or compositions disclosed herein. A device disclosed herein may be a container, holder or other solid support onto or into which a honeybee repellent or composition disclosed herein. A device disclosed herein may be made form any biological or synthetic material, including, without limitation, paper, filter paper, wood, cork, cotton, plastic, polymer, metal, or glass.

Aspects of the present specification disclose a use of a honeybee repellent disclosed herein to repel a honeybee from a location treated with the honeybee repellent. In one embodiment, the disclosed use is a use of a honeybee repellent disclosed herein to repel a honeybee from foraging and/or collecting nectar from a flower of a plant treated with the honeybee repellent. In another embodiment, the disclosed use is a use of a honeybee repellent disclosed herein to repel a honeybee from a structure treated with the honeybee repellent.

Aspects of the present specification disclose a method of treating a location by applying a honeybee repellent disclosed herein, wherein such application repels a honeybee from the treated location. In one embodiment, the disclosed method is a method of treating a plant by applying a honeybee repellent disclosed herein, wherein such application repels a honeybee from foraging and/or collecting nectar from a flower of the treated plant. In another embodiment, the disclosed method is a method of treating a structure by applying a honeybee repellent disclosed herein, wherein such application repels a honeybee from the treated structure.

Aspects of the present specification disclose a method of reducing or preventing a honeybee foraging to a location by applying a honeybee repellent or composition disclosed herein, wherein such application repels honeybees from the location, thereby reducing or preventing the honeybee foraging. In one embodiment, the disclosed method is a method of treating a plant by applying a honeybee repellent or composition disclosed herein, wherein such application repels a honeybee from foraging for a meal in the vicinity of the treated plant, flower, or seed. In another embodiment, the disclosed method is a method of treating a structure by applying a honeybee repellent or composition disclosed herein, wherein such application repels a honeybee from foraging for a meal in the vicinity of the treated structure.

As used herein, the term "location" refers to any site to which movement of a honeybee is to be retarded. A location includes, by way of example, a plant or group of plants or part of a plant, a particular area of land, or a man-made structure, such as, e.g., a commercial building, a house, a shed, or other physical structure. As used herein, the term "plant" refers to any living organism belonging to the Kingdom Plantae. Non-limiting examples include trees, flowering plant, herbs, bushes, grasses, vines, ferns, mosses, and green algae. As used herein, the term "flower" is synonymous with "bloom" or "blossom" and refers the reproductive structure found in angiosperms. As used herein, the term "crop plant" refers to a plant that produces a crop. Non-limiting examples include are plants that produce fruits, seeds, nuts, grains, oil, wood, and fibers. As used herein, the term "crop" refers to a plant product which is of economical value. Non-limiting examples include are fruits, seeds, nuts, grains, oil, wood, and fibers.

A honeybee repellent or composition disclosed herein is applied to a location by any method that can dispense to a location an amount of honeybee repellent effective in repelling a honeybee. A method of application is not critical and many well known methods can be used. In one embodiment, an appropriate amount of a honeybee repellent or composition disclosed herein can be dissolved into an appropriate compatible solvent and dispensed as a solution onto the intended location. The solvent employed is typically a volatile solvent (i.e., having a boiling point of about 100° C. or less) that will evaporate over a period of time. In another embodiment, an appropriate amount of a honeybee repellent or composition disclosed herein can be combined with an appropriate propellant and used as a spray for application onto the intended location.

In another embodiment, a honeybee repellent or composition disclosed herein can be impregnated into a compatible matrix. As used herein, the term "compatible matrix" refers to any material in which one or more repellent compounds disclosed herein are either soluble or miscible and where the material does not significantly alter or degrade the attractant activity of the one or more repellent compound. In aspects of this embodiment, a compatible matrix does not significantly alter or degrade an attractant activity of one or more honeybee repellents over a period of, e.g., at least 7 days, at least 14 days, at least 21 days, at least 28 days, at least 35 days, at least 42 days, at least 49 days, at least 56 days, or at least 63 days. Impregnation of a repellent compound into the compatible matrix can be achieved by any well known methods known in the art. For example, a honeybee repellent can be dissolved into a compatible volatile solvent and the resulting solution added to the matrix whereupon evaporation of the solvent results in impregnation of the repellent compound into the compatible matrix. In this regard, the matrix can be cotton twine, polymers such as, e.g., polyvinyls, polyisoprenes, polyethylene, polypropylene or copolymers thereof, or polybutenes. In another example, a compatible matrix is thinned by heating and then a repellent compound is added directly thereto. The mixture can then be combined with twine or other compatible matrices. A compatible matrix disclosed herein may be employed by itself or incorporated into a device used to house the matrix.

In another embodiment, a honeybee repellent or composition disclosed herein can be incorporated into a controlled-release device which dispenses a honeybee repellent and/or other beneficial compound over time in a regulated or predictable manner. A controlled-release device disclosed herein may be employed by itself or incorporated into another device used to house the controlled-release device.

One type of controlled-release device is a "reservoir" device where a honeybee repellent or composition forms a core surrounded by an inert diffusion barrier. An inert diffusion barrier includes membranes which are non-porous, homogeneous polymeric films, through which transport occurs by a process of dissolution of the permeating species in the polymer at one interface and diffusion down a gradient in thermodynamic activity. These membranes are usually referred to as solution-diffusion membranes. Another class inert diffusion barrier includes the porous and/or fibrous barriers such as, for example, hollow fibers, porous and/or fibrous materials, in which a repellent compound diffuses mainly by capillary forces. Other less common reservoir devices are designed to enable diffusion to take place by mechanical pumping or under external forces, such as, e.g., gravity, electrical field, vacuum, or centrifugal forces. A reservoir device can exist in a variety of shapes, and can be degradable or non-degradable.

In an aspect of this embodiment, a reservoir device is a microcapsule comprising a core of a honeybee repellent or composition disclosed herein surrounded by a coating or shell of, e.g., a polyvinyl chloride (PVC)-polyvinyl acetate (PVA) plastic. Size typically varies from about 1 μm to about 1000 μm and can have irregular or geometric shapes. Core payload usually varies from 0.1 to 98 weight percent. Encapsulation processes are often loosely classified as either chemical or mechanical. Examples of chemical processes include but are not limited to complex coacervation, polymer-polymer incompatibility, interfacial polymerization in liquid media, in situ polymerization, in-liquid drying, thermal andionic gelation in liquid media, desolvation in liquid media, starch-based chemistry processes, trapping in cyclodextrins, and formation of liposomes. Examples of mechanical processes include but are not limited to spray drying, spray chilling, fluidized bed, electrostatic deposition, centrifugal extrusion, spinning disk or rotational suspension separation, annular-jet encapsulation, polymerization at liquid-gas or solid-gas interface, solvent evaporation, pressure extrusion or spraying into solvent extraction bath.

Another type of controlled-release device is a "monolithic" device where a honeybee repellent or composition is dissolved or dispersed throughout a substantially inert matrix from which the repellent compound and/or other beneficial compound is gradually released. Non-limiting examples of matrices included in a monolithic device include various gels, waxes, gelatins, natural resins, rubbers, elastomers, synthetic and natural polymers. A monolithic device can exist in a variety of shapes, and can be degradable or non-degradable. Size can vary depending on the application. For example, a monolithic device can be produced as a microcapsule having a size of about 1 μm to about 1000 μm with irregular or geometric shapes. As another example, a monolithic device can have a size of about 1 mm to about 10 cm with irregular or geometric shape.

A controlled-release device disclosed herein can be a liquid composition or a solid composition. A liquid sustained-release formulation includes a honeybee repellent or composition disclosed herein, a solvent, and typically further comprise surface active agents to render the composition readily dispersible in water, such agents include a wetting agent, an emulsifying agent, or a dispersing agent. In one embodiment, a liquid form of a sustained-release formulation is an emulsion formulation, such as, e.g., a water in oil (w/o) emulsion or oil in water (o/w) emulsion. Non-limiting examples of oils include vegetable oils and mineral oils. Droplet size can vary from the nanometer scale (colloidal dispersion) to several hundred microns. A variety of surfactants and thickeners are usually incorporated in the formulation to modify the size of the droplets, stabilize the emulsion, and modify the release.

A solid form of controlled-release device comprises a solid substrate like porous particulates such as silica, perlite, talc, clay, pyrophyllite, diatomaceous earth, gelatin and gels, polymers (e.g., polyurea, polyurethane, polyamide, polyester, etc.), polymeric particles, or cellulose. These include, for example, hollow fibers, hollow tubes ortubing which release a repellent compound disclosed herein through the walls, capillary tubing which releases the compound out of an opening in the tubing, polymeric blocks of different shapes, e.g., strips, blocks, tablets, discs, which release the compound out of the polymer matrix, membrane systems which hold the repellent compound within an impermeable container and release it through a measured permeable membrane, and combinations of the foregoing. Examples of other dispensing means are polymer laminates, polyvinyl chloride pellets, and microcapillaries.

Controlled release can also be achieved by a number of other methods such as, e.g., complexation of a honeybee repellent or composition, slowly dissolving coatings, erosion, microbial action, or use of derivatives or new compounds of reduced solubility or volatility.

In aspects of this embodiment, a controlled-release device releases a honeybee repellent or composition disclosed herein with substantially zero order release kinetics over a periodof, e.g., about 7 days, about 15 days, about 30 days, about 45 days, about 60 days, about 75 days, or about 90 days. In other aspects of this embodiment, a controlled-release device releases a honeybee repellent or composition disclosed herein with substantially zero order release kinetics over a periodof, e.g., at least 7 days, at least 15 days, at least 30 days, at least 45 days, at least 60 days, at least 75 days, or at least 90 days. In other aspects of this embodiment, a controlled-release device releases a honeybee repellent or composition disclosed herein with substantially zero order release kinetics over a periodof between, e.g., about 7 days to about 30 days, about 15 days to about 45 days, about 30 days to about 60 days, about 45 days to about 75 days, or about 60 days to about 90 days.

In aspects of this embodiment, a controlled-release device releases a honeybee repellent or composition disclosed herein with substantially first order release kinetics over a periodof, e.g., about 7 days, about 15 days, about 30 days, about 45 days, about 60 days, about 75 days, or about 90 days. In other aspects of this embodiment, a controlled-release device releases a honeybee repellent or composition disclosed herein with substantially first order release kinetics over a periodof, e.g., at least 7 days, at least 15 days, at least 30 days, at least 45 days, at least 60 days, at least 75 days, or at least 90 days. In other aspects of this embodiment, a controlled-release device releases a honeybee repellent or composition disclosed herein with substantially first order release kinetics over a periodof between, e.g., about 7 days to about 30 days, about 15 days to about 45 days, about 30 days to about 60 days, about 45 days to about 75 days, or about 60 days to about 90 days.

Regardless of the method of application, the amount of a honeybee repellent disclosed herein used is a repellent effective amount, i.e., it is an amount sufficient to retard the movement of honeybees to the selected location. In aspects of this embodiment, a honeybee repellent disclosed herein is applied at a rate of, e.g., about 0.01 mg/m$^2$, about 0.025 mg/m$^2$, about 0.05 mg/m$^2$, about 0.075 mg/m$^2$, about 0.1 mg/m$^2$, about 0.25 mg/m$^2$, about 0.5 mg/m$^2$, about 0.75 mg/m$^2$, about 1 mg/m$^2$, about 2.5 mg/m$^2$, about 5 mg/m$^2$, about 7.5 mg/m$^2$, or about 10 mg/m$^2$. In other aspects of this embodiment, a honeybee repellent disclosed herein is applied at a rate of, e.g., at least 0.01 mg/m$^2$, at least 0.025 mg/m$^2$, at least 0.05 mg/m$^2$, at least 0.075 mg/m$^2$, at least 0.1 mg/m$^2$, at least 0.25 mg/m$^2$, at least 0.5 mg/m$^2$, at least 0.75 mg/m$^2$, at least 1 mg/m$^2$, at least 2.5 mg/m$^2$, at least 5 mg/m$^2$, at least 7.5 mg/m$^2$, or at least 10 mg/m$^2$. In yet other aspects of this embodiment, a honeybee repellent disclosed herein is applied at a rate of, between e.g., about 0.01 mg/m$^2$ to about 10 mg/m$^2$, about 0.01 mg/m$^2$ to about 1 mg/m$^2$, about 0.01 mg/m$^2$ to about 0.1 mg/m$^2$, about 0.05 mg/m$^2$ to about 10 mg/m$^2$, about 0.05 mg/m$^2$ to about 1 mg/m$^2$, about 0.05 mg/m$^2$ to about 0.1 mg/m$^2$, about 0.05 mg/m$^2$ to about 5 mg/m$^2$, or about 0.05 mg/m$^2$ to about 0.5 mg/m$^2$.

Aspects of the present specification may also be described as follows:

1. A honeybee repellent that substantially mimics a repellent chemosensory cue of 2-heptanone, wherein the compound is not 2-heptanone.
2. The honeybee repellent according to embodiment 1, wherein the honeybee repellent has a repellent chemosensory cue that is at least 75%, at least 80%, at least 85%, at least 90%, at least 95%, or at least 97% that of the repellent chemosensory cue of 2-heptanone.
3. The honeybee repellent according to embodiment 1, wherein the honeybee repellent has a repellent chemosensory cue that is at least one-fold, at least two-fold, at least three-fold, at least four fold, at least five-fold, at least six-fold, at least seven-fold, at least eight-fold, at least nine-fold, at least 10-fold, at least 20-fold, at least 30-fold, at least 40-fold, at least 50-fold, at least 60-fold, at least 70-fold, at least 80-fold, at least 90-fold, at least 100-fold, at least 125-fold, at least 150-fold, at least 175-fold, or at least 200-fold that of the repellent chemosensory cue of 2-heptanone.
4. A honeybee repellent having a honeybee repellency activity, wherein the compound is not 2-heptanone.
5. The honeybee repellent according to embodiment 4, wherein the honeybee repellent repels honeybees by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%, as compared to not having the honeybee repellent present.
6. The honeybee repellent according to embodiment 4 or 5, wherein the honeybee repellent reduces a honeybee interaction with a mammal, a plant, structure, and/or location.
7. The honeybee repellent according to any one of embodiments 4-6, wherein the honeybee repellent reduces a honeybee interaction with a mammal, a plant, structure, and/or location by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.
8. The honeybee repellent according to any one of embodiments 4-7, wherein the honeybee repellent reduces an ability of a honeybee to obtain a meal and/or nectar from a plant.
9. The honeybee repellent according to any one of embodiments 4-8, wherein the honeybee repellent reduces an ability of a honeybee to obtain a meal and/or nectar from a plant by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.
10. The honeybee repellent according to any one of embodiments 1-9, wherein the honeybee repellent is more stable than 2-heptanone.
11. The honeybee repellent according to any one of embodiments 1-10, wherein the honeybee repellent is less volatile than 2-heptanone.
12. The honeybee repellent according to any one of embodiments 1-11, wherein the honeybee repellent has a half-life of at least one day, at least three days, at least five days, at least one week, at least two weeks, at least three weeks, at least one month, at least two months, or at least three months.
13. The honeybee repellent according to embodiments 1-11, wherein the honeybee repellent has a half-life about one day to about seven days, about three days to about seven days, about five days to about seven days, about one week to about four weeks, about two weeks to about four weeks, about three weeks to about four weeks, about one month to about four months, about two months to about four months, or about three months to about four months.
14. The honeybee repellent according to any one of embodiments 1-13, wherein the honeybee repellent has a binding affinity for a honeybee OBP that is substantially the same as the binding affinity of 2-heptanone, wherein the compound is not 2-heptanone.
15. The honeybee repellent according to any one of embodiments 1-14, wherein the honeybee repellent has a binding affinity for a honeybee OBP that is at least 75%, at least 80%, at least 85%, at least 90%, at least 95%, or at least 97% that of the binding affinity of 2-heptanone for that honeybee OBP.
16. The honeybee repellent according to any one of embodiments 1-15, wherein the honeybee repellent has a dissociation equilibrium constant that is greater than the dissociation equilibrium constant of 2-heptanone for that honeybee OBP by at least one-fold, at least two-fold, at least three-fold, at least four fold, at least five-fold, at least six-fold, at least seven-fold, at least eight-fold, at least nine-fold, at least 10-fold, at least 20-fold, at least 30-fold, at least 40-fold, at least 50-fold, at least 60-fold, at least 70-fold, at least 80-fold, at least 90-fold, at least 100-fold, at least 125-fold, at least 150-fold, at least 175-fold, or at least 200-fold.
17. The honeybee repellent according to any one of embodiments 1-16, wherein the honeybee repellent has an association rate constant of less than $1 \times 10^5$ $M^{-1}$ $s^{-1}$, less than $1 \times 10^6$ $M^{-1}$ $s^{-1}$, less than $1 \times 10^7$ $M^{-1}$ $s^{-1}$, or less than $1 \times 10^8$ $M^{-1}$ $s^{-1}$.
18. The honeybee repellent according to any one of embodiments 1-16, wherein the honeybee repellent has an association rate constant of more than $1 \times 10^5$ $M^{-1}$ $s^{-1}$, more than $1 \times 10^6$ $M^{-1}$ $s^{-1}$, more than $1 \times 10^7$ $M^{-1}$ $s^{-1}$.
19. The honeybee repellent according to any one of embodiments 1-18, wherein the honeybee repellent has a disassociation rate constant of less than $1 \times 10^{-3}$ $s^{-1}$, less than $1 \times 10^{-4}$ $s^{-1}$, or less than $1 \times 10^{-5}$ $s^{-1}$.
20. The honeybee repellent according to any one of embodiments 1-18, wherein the honeybee repellent has a disassociation rate constant of more than $1 \times 10^{-3}$ $s^{-1}$, more than $1 \times 10^{-4}$ $s^{-1}$, or more than $1 \times 10^{-5}$ $s^{-1}$.
21. The honeybee repellent according to any one of embodiments 1-20, wherein the honeybee repellent has an equilibrium disassociation constant of less than 0.500 nM, less than 0.450 nM, less than 0.400 nM, less than 0.350 nM, less than 0.300 nM, less than 0.250 nM, less than 0.200 nM, less than 0.150 nM, less than 0.100 nM, or less than 0.050 nM.
22. The honeybee repellent according to any one of embodiments 1-20, wherein the honeybee repellent has an equilibrium disassociation constant of more than 0.500 nM, more than 0.450 nM, more than 0.400 nM, more than 0.350 nM, more than 0.300 nM, more than 0.250 nM, more than 0.200 nM, more than 0.150 nM, more than 0.100 nM, or more than 0.050 nM.
23. The honeybee repellent according to any one of embodiments 1-22, wherein the honeybee repellent has a structure of formula I disclosed herein.

24. The honeybee repellent according to any one of embodiments 1-23, wherein the honeybee repellent has a structure of formula II disclosed herein.
25. The honeybee repellent according to any one of embodiments 1-23, wherein the honeybee repellent has a structure of formula III disclosed herein.
26. The honeybee repellent according to any one of embodiments 1-23, wherein the honeybee repellent has a structure of formula IV disclosed herein.
27. The honeybee repellent according to any one of embodiments 1-23, wherein the honeybee repellent has a structure of formula V disclosed herein.
28. The honeybee repellent according to any one of embodiments 1-22, wherein the honeybee repellent has a structure of formula VI, formula VIa, formula VIb, formula VIc, formula VId, formula VIe, formula VIf, and/or formula VIg disclosed herein.
29. The honeybee repellent according to any one of embodiments 1-22, wherein the honeybee repellent has a structure of formula VII, formula VIIa, formula VIIb, formula VIIc, formula VIId, and/or formula VIIe disclosed herein.
30. The honeybee repellent according to any one of embodiments 1-22, wherein the honeybee repellent has a structure of formula VIII, formula VIIIa, formula VIIIb, formula VIIIc, formula VIIId, and/or formula VIIIe disclosed herein.
31. The honeybee repellent according to any one of embodiments 1-22, wherein the honeybee repellent has a structure of formula IX, formula IXa, formula IXb, formula IXc, formula IXd, formula IXe, formula IXf, and/or formula IXg disclosed herein.
32. The honeybee repellent according to any one of embodiments 1-22, wherein the honeybee repellent has a structure of formula X, formula Xa, formula Xb, formula Xc, formula Xd, formula Xe, formula Xf, formula Xg, formula Xh, and/or formula Xi disclosed herein.
33. The honeybee repellent according to any one of embodiments 1-22, wherein the honeybee repellent has a structure of formula XI, formula XIa, formula XIb, formula XIc, formula XId, formula XIe, formula XIf, and/or formula XIg disclosed herein.
34. The honeybee repellent according to any one of embodiments 1-22, wherein the honeybee repellent has a structure of formula XII, formula XIIa, formula XIIb, and/or formula XIIc disclosed herein.
35. The honeybee repellent according to any one of embodiments 1-22, wherein the honeybee repellent has a structure of formula XIII, formula XIIIa, formula XIIIb, formula XIIIc, formula XIIId, and/or formula XIIIe disclosed herein.
36. The honeybee repellent according to any one of embodiments 1-22, wherein the honeybee repellent has a structure of formula XIV, formula XIVa, formula XIVb, and/or formula XIVc disclosed herein.
37. The honeybee repellent according to any one of embodiments 1-22, wherein the honeybee repellent has a structure of formula XV, formula XVa, formula XVb, and/or formula XVc disclosed herein.
38. The honeybee repellent according to any one of embodiments 1-22, wherein the honeybee repellent has a structure of formula XVI, formula XVIa, formula XVIb, formula XVIc, formula XVId, and/or formula XVIe disclosed herein.
39. The honeybee repellent according to any one of embodiments 1-38, wherein the honeybee repellent is an optionally substituted 1-{[(4-iodophenyl)imino]methyl}-2-naphthol, an optionally substituted (2,5-dimethylphenyl) [(2-methoxy-1-naphthyl)methylene]amine, an optionally substituted 2-hydroxy-1-naphthaldehyde 2-pyridinylhydrazone, an optionally substituted 1,2-naphthalenedione 1-(2,3-dihydro-1,4-benzodioxin-6-ylhydrazone), an optionally substituted N-{3-[(diethylamino)carbonyl]-5,6,7,8-tetrahydro-4H-cyclohepta[b]thien-2-yl}-2-furamide, an optionally substituted N-(3-{[(4-methylphenyl)amino]carbonyl}-5,6,7,8-tetrahydro-4H-cyclohepta[b]thien-2-yl)-2-furamide, an optionally substituted N-[3-(1-piperidinylcarbonyl)-5,6,7,8-tetrahydro-4H-cyclohepta[b]thien-2-yl]benzamide, an optionally substituted 4-(4,6-diphenyl-1,2-dihydro-1,3,5-triazin-2-yl)-2-methoxyphenol, an optionally substituted 4-phenoxy-2-phenyl-6-(1H-pyrazol-1-yl)pyrimidine, an optionally substituted 2-bromo-4-chloro-6-[(2-pyridinylimino)methyl]phenol, an optionally substituted 1-(4-bromophenyl)-3-[(2-hydroxyphenyl)amino]-2-propen-1-one, an optionally substituted 5-[4-(4-morpholinyl)-3-nitrobenzylidene]-2-thioxo-1,3-thiazolidin-4-one, an optionally substituted 5-(5-bromo-2-methoxybenzylidene)-3-ethyl-2-thioxo-1,3-thiazolidin-4-one, an optionally substituted [3-amino-6-(3-pyridinyl)thieno[2,3-b]pyridin-2-yl](phenyl)methanone, an optionally substituted 3-iodo-N'-[(2-methyl-1H-indol-3-yl)methylene]benzohydrazide, an optionally substituted N,N'-bis(2-acetylphenyl)tetrahydro-2,5-thiophenedicarboxamide, an optionally substituted 2-[2-(4-chlorophenyl)-2-oxoethylidene]-1,3-thiazolidin-4-one, an optionally substituted ethyl 4-{4-[4-(4-morpholinyl)benzylidene]-3,5-dioxo-1-pyrazolidinyl}benzoate, an optionally substituted 3-iodo-1-[(1H-1,2,4-triazol-3-ylimino)methyl]-6,7,8,9-tetrahydrodibenzo[b,d]furan-2-ol, an optionally substituted 10-hydroxy-1,2-dihydro-12H-benzo[4,5]isoquino[2,1-a]cyclopenta[gh]perimidin-12-one, or an optionally substituted 1-benzoyl-3-phenyl-5-(trifluoromethyl)-4,5-dihydro-1H-pyrazol-5-ol.
40. The honeybee repellent according to any one of embodiments 1-38, wherein the honeybee repellent is an optionally substituted 3-bromo-7,8-diethoxy-4-methyl-6-nitro-2H-chromen-2-one, an optionally substituted 4-hydroxy-3-[2-(4-hydroxyphenyl)-2,3-dihydro-1,5-benzothiazepin-4-yl]-6-methyl-2H-pyran-2-one, an optionally substituted 6-(4-iodophenyl)imidazo[2,1-b][1,3]thiazole, an optionally substituted 4-(2-furylmethylene)-2-(4-methylphenyl)-1,3-oxazol-5(4H)-one, an optionally substituted 2-(3-bromophenyl)-2-oxoethyl benzoate, an optionally substituted 2-anilino-8-quinolinol, an optionally substituted (4-amino-3-nitrophenyl)(phenyl)methanone, an optionally substituted N-[2-(aminocarbonyl)phenyl]-2-naphthamide, an optionally substituted N,N'-bis(2-acetylphenyl)tetrahydro-2,5-thiophene dicarboxamide, an optionally substituted 3-iodo-N'-[(2-methyl-1H-indol-3-yl)methylene]benzohydrazide, an optionally substituted N'-(2-bromo-5-methoxybenzylidene)-2-(4-ethylphenoxy)acetohydrazide, an optionally substituted 9H-fluoren-9-one thiosemicarbazone, an optionally substituted 5-(4-nitrophenyl)-2,3,5,6-tetrahydrobenzo[a]phenanthridin-4(1H)-one, an optionally substituted N'-(4-bromo-5-methyl-2-oxo-1,2-dihydro-3H-indol-3-ylidene)spiro[2.3]hexane-1-carbohydrazide, an optionally substituted 2-[4-(allyloxy)-6-methyl-2-pyrimidinyl]phenol, an optionally substituted 2-[6-phenyl-2-(1-piperazinyl)-4-pyrimidinyl]phenol, an optionally substituted 4-{[(9-ethyl-9H-carbazol-3-yl)methylene]amino}benzamide, an optionally substituted ethyl 1-amino-3-isopropyl-3,4-dihydro-2-naphthalenecarboxylate, an optionally substituted ethyl [(4-oxo-3-phenyl-4,6-dihydro-3H-spiro[benzo[h]quinazoline-5,1'-cyclopentan]-2-yl)thio]acetate, an optionally substituted 1-(3,6-dichloro-9H-carbazol-9-yl)-3-(4- morpholinyl)-2-propanol, an optionally substituted 1-(3,6-dibromo-9H-carbazol-9-yl)-3-(4-morpholinyl)-2-propanol, an optionally substituted 3-[3-(3,6-dichloro-9H-carbazol-9-yl)-2-hydroxypropyl]-1,3-thiazolidine-2,4-dione, an optionally substituted 2-(benzoylamino)-N-(4-chlorophenyl)benzamide, an optionally substituted 1-(1-adamantyl)-N-mesityl-2-piperidine carboxamide hydrochloride, an optionally substituted 1-benzyl-4-(4-methoxy-3-methylbenzyl) piperazine, an optionally substituted 1-(4-methoxy-2,3-dimethylbenzyl)-4-(3-phenyl-2-propen-1-yl)piperazine, an optionally substituted 1-phenyl-1-propanone N-(3-methylphenyl)thiosemicarbazone, an optionally substituted 4-[(2-chloro-5-nitrobenzylidene) amino]phenol, an optionally substituted N-(4-nitrophenyl)-1H-indol-3-amine, an optionally substituted 4-(1H-pyrrol-1-yl)-5,6,7,8-tetrahydro[1]benzothieno[2,3-d]pyrimidine, an optionally substituted 2,2,4-trimethyl-1,2-dihydro-6-quinolinyl 3-methoxybenzoate, an optionally substituted 7-(diethylamino)-4-methyl-3-nitro-2H-chromen-2-one, an optionally substituted (4-bromo-3-chlorophenyl)(4-ethoxybenzylidene)amine, an optionally substituted 3-{[(9-ethyl-9H-carbazol-3-yl)methylene]amino}benzamide, an optionally substituted N~1~-(9-anthrylmethylene)-1H-tetrazole-1,5-diamine, an optionally substituted N-phenyl-N'-[2-(phenylethynyl)phenyl]urea, an optionally substituted (9-anthrylmethylene)(3-nitrophenyl)amine, an optionally substituted 2,4-di-tert-butyl-6-[(methylimino)methyl]phenol, an optionally substituted N'-[(2-chlorobenzoyl)oxy]benzenecarboximidamide, an optionally substituted N-(3-chloro-2-methylphenyl)-2-naphthalenesulfonamide, an optionally substituted 2-[2-(3,5-dimethyl-1H-pyrazol-1-yl)-6-phenyl-4-pyrimidinyl]phenol, an optionally substituted 2-[4-(4-methoxy-2,5-dimethylbenzyl)-1-piperazinyl]ethanol, an optionally substituted 2-(benzylthio)-5-(2-chlorophenyl)-1,3,4-oxadiazole, an optionally substituted 2-[(4-bromobenzyl)thio]-5-phenyl-1,3,4-oxadiazole, an optionally substituted 3-chloro-2-phenyl-4H-chromen-4-on e, an optionally substituted N-benzyl-2,5-dichloro-N-ethylbenzenesulfonamide, an optionally substituted 4-fluoro-N-{[(2-methoxyphenyl)amino]carbonothioyl}benzamide, an optionally substituted 3-[(4-chlorobenzoyl)amino]propyl 4-chlorobenzoate, an optionally substituted methyl 3-[(4-fluorobenzoyl)amino]-2-butenoate, an optionally substituted 1-(4-methoxyphenyl)-3-(1-naphthyl)-2-propen-1-one, an optionally substituted 6-{2-[5-(3-chlorophenyl)-2-furyl]vinyl}-4-(trifluoromethyl)-2(1H)-pyrimidinone, an optionally substituted 9-amino-7H-benzimidazo[2,1-a]benzo[de]isoquinolin-7-one, an optionally substituted N-benzyl-2-phenyl-N-(3-pyridinylmethyl) ethanamine, an optionally substituted (3,4-difluorophenyl)[3-(4-methoxyphenyl)-1-methylpropyl]amine, an optionally substituted 1-(4-chlorophenyl)-3-(2-hydroxyphenyl)-1,3-propanedione, an optionally substituted N-(2-methylphenyl)-9-oxo-9H-fluorene-1-carboxamide, an optionally substituted N-[2-(4-chlorophenoxy)ethyl]-5-(3-methyl-1-piperazinyl)-2-nitroaniline, an optionally substituted 2-({[4-(benzylamino)phenyl]imino}methyl)-4bromophenol, an optionally substituted 3-methyl-1-phenyl-1H-pyrazole-4,5-dione 4-[(3-hydroxyphenyphydrazone], an optionally substituted ethyl methyl 4-(4-bromophenyl)-2,6-dimethyl-1,4-dihydro-3,5-pyridinedicarboxylate, an optionally substituted benzyl 2-methyl-4-(4-methylphenyl)-5-oxo-1,4,5,6,7,8-hexahydro-3-quinolinecarboxylate, an optionally substituted 2-cyclohexyl-1H-naphtho[2,3-g]indazole-3,6,11(2H)-trione, an optionally substituted 2-phenoxyethyl 4-(3-fluorophenyl)-6-methyl-2-oxo-1,2,3,4-tetrahydro-5-pyrimidinecarboxylate, an optionally substituted 1,3-naphthalenediyl bis(2-methylpropanoate), an optionally substituted 7-methyl-3-(4-methylbenzoyl)-4H-chromen-4-one, an optionally substituted 2-[2-(2-aminophenyl)vinyl]-5,7-dimethyl-8-quinolinol, an optionally substituted 2,6-diphenyl-4H-1,3-dioxin-4-one, an optionally substituted 3-allyl-5-(2-hydroxy-3-nitrobenzylidene)-2-thioxo-1,3-thiazolidin-4-one, an optionally substituted 3,5-diphenyl-1-(trifluoroacetyl)-4,5-dihydro-1H-pyrazole, an optionally substituted 5-(2-chloro-5-nitrobenzylidene)-2-[(2-chlorophenyl)imino]-1,3-thiazolidin-4-one, an optionally substituted 2,6-di-tert-butylbenzo-1,4-quinone 4-thiosemicarbazone, an optionally substituted 2-ethyl-1-[(7-methyl-2-naphthyl)sulfonyl]piperidine, an optionally substituted 5-benzyl-3-bromo-2-hydroxpenzaldehyde, an optionally substituted 3-[5-(2-nitrophenyl)-2-furyl]-1-phenyl-2-propen-1-one, an optionally substituted 2-(1,3-benzothiazol-2-ylthio)-1-(3-nitrophenyl)ethanone, an optionally substituted isonicotinaldehyde diphenylhydrazone, an optionally substituted N'-(2-hydroxy-3-methoxybenzylidene)-2-[(2-methylphenyl)amino]acetohydrazide (non-preferred name), an optionally substituted 5-(1,3-benzodioxol-5-ylmethylene)-3-(1,5-dimethyl-3-oxo-2-phenyl-2,3-dihydro-1H-pyrazol-4-yl)-2-thioxo-1,3-thiazolidin-4-one, an optionally substituted N'-{[5-(2,3-dichlorophenyl)-2-furyl]methylene}isonicotinohydrazide, an optionally substituted 1-[3-(3,6-dibromo-9H-carbazol-9-yl)-2-hydroxypropyl]-2,5-pyrrolidinedione, an optionally substituted N'-{[5-(3-chloro-4-methoxyphenyl)-2-furyl]methylene}-2-pyridinecarbohydrazide, an optionally substituted N'-{[5-(4-bromophenyl)-2-furyl]methylene}-2-[(4-methylphenyl)amino]acetohydrazide, an optionally substituted 2-[(1-bromo-2-naphthyl)oxy]-N'-(2-hydroxy-5-methoxybenzylidene)butanohydrazide, an optionally substituted 1-[3-(3,6-dichloro-9H-carbazol-9-yl)-2-hydroxypropyl]-2,5-pyrrolidinedione, an optionally substituted N-(4-chloro-2,5-dimethoxyphenyl)-2-phenoxybutanamide, an optionally substituted N-[2-(aminocarbonyl)phenyl]-3-chloro-1-benzothiophene-2-carboxamide, an optionally substituted N-(2-furylmethyl)-4-hydroxy-1-(3-methylbutyl)-2-oxo-1,2-dihydro-3-quinolinecarboxamide, an optionally substituted methyl 5-{[(4-bromophenyl)amino]sulfonyl}-2-chlorobenzoate, an optionally substituted 3-allyl-5-{3-[(4-nitrobenzyl)oxy]benzylidene}-2-thioxo-1,3-thiazolidin-4-one, an optionally substituted 2-(2-fluorobenzylidene)-6-methoxy-3,4-dihydro-1(2H)-naphthalenone, an optionally substituted 2-(ethylthio)ethyl 4-(2-chlorophenyl)-6-methyl-2-oxo-1,2,3,4-tetrahydro-5-pyrimidinecarboxylate, an optionally substituted 2-{3-[4-(9H-fluoren-9-yl)-1-piperazinyl]-3-oxopropyl}-1H-isoindole-1,3(2H)-dione, an optionally substituted 3-(5-bromo-2-methoxyphenyl)-1-(3,4-dimethoxyphenyl)-2-propen-1-one, an optionally substituted ethyl 4-{4-[4-(4-morpholinyl) benzylidene]-3,5-dioxo-1-pyrazolidinyl}benzoate, an optionally substituted 3-methyl-6-(1-piperidinyl)-3H-naphtho[1,2,3-de]quinoline-2,7-dione, an optionally substituted 3,4-dimethylphenyl 2-chlorobenzoate, an optionally substituted spiro[cyclopentane-1,6'-isoquino[1,2-b]quinazolin]-8'(5'H)-one, an optionally substituted 1-benzoyl-5-(2-hydroxyphenyl)-3-(trifluoromethyl)-4,5-dihydro-1H-pyrazol-5-ol, an optionally substituted 1-(4-methoxpenzoyl)-3-phenyl-5-(trifluoromethyl)-4,5-dihydro-1H-pyrazol-5-ol, an optionally substituted 4-hydroxy-1-methyl-2-oxo-N-(1-phenylethyl)-1,2-dihydro-3-quinoline carboxamide, an optionally substituted 3-(4-chlorophenyl)-1-(3-pyridinylcarbonyl)-5-(trifluoromethyl)-4,5-dihydro-1H-pyrazol-5-ol, an optionally substituted 4-bromo-N'-[2-(trifluoroacetyl)-1-cyclopenten-1-yl]benzohydrazide, an optionally substituted 5-{2-[(2,4-dichlorobenzyl)oxy]-3-methoxybenzylidene}-2-imino-1,3-thiazolidin-4-one, an optionally substituted ethyl 2-{[(acetylamino) carbonothioyl]amino}-4-phenyl-3-thiophenecarboxylate, an optionally substituted N'-[1-(1,3-dioxo-2,3-dihydro-1H-inden-2-yl)ethylidene]-3-hydroxy-2-naphthohydrazide, an optionally substituted 9-methyl-2-phenyl-9H-imidazo[1,2-a]benzimidazole-3-carbaldehyde, an optionally substituted 2-(4-bromophenyl)-3-[(4-nitrophenyl)sulfonyl]-1,3-thiazolidine, an optionally substituted 9-amino-7H-benzimidazo[2,1-a]benzo[de]isoquinolin-7-one, an optionally substituted 1-(4-methoxyphenyl)-3-(1-methyl-1H-indol-3-yl)-2-propen-1-one, an optionally substituted N-methyl-N-[(6-nitro-1,3-benzodioxol-5-yl)methyl]-2-(2-pyridinyl)ethanamine, an optionally substituted 4-[(6-nitro-1,3-benzodioxol-5-yl)methyl]thiomorpholine, an optionally substituted 1,1'-(1,4-phenylene)bis[3-(1H-indol-3-yl)-2-propen-1-one], an optionally substituted 1-(4-biphenylyl)-3-(1H-indol-3-yl)-2-propen-1-one, or an optionally substituted 1-methyl-4-[(6-nitro-1,3-benzodioxol-5-yl)methyl]piperazine.

41. The honeybee repellent according to any one of embodiments 1-39, wherein the honeybee repellent is not 1-{[(4-iodophenyl)imino]methyl}-2-naphthol, (2,5-dimethylphenyl)[(2-methoxy-1-naphthyl)methylene]amine, 2-hydroxy-1-naphthaldehyde 2-pyridinylhydrazone, 1,2-naphthalenedione 1-(2,3-dihydro-1,4-benzodioxin-6-yl)hydrazone), N-{3-[(diethylamino)carbonyl]-5,6,7,8-tetrahydro-4H-cyclohepta[b]thien-2-yl}-2-furamide, N-(3-{[(4-methylphenyl)amino]carbonyl}-5,6,7,8-tetrahydro-4H-cyclohepta[b]thien-2-yl)-2-furamide, N-[3-(1-piperidinylcarbonyl)-5,6,7,8-tetrahydro-4H-cyclohepta[b]thien-2-yl]benzamide, 4-(4,6-diphenyl-1,2-dihydro-1,3,5-triazin-2-yl)-2-methoxyphenol, 4-phenoxy-2-phenyl-6-(1H-pyrazol-1-yl)pyrimidine, 2-bromo-4-chloro-6-[(2-pyridinylimino)methyl]phenol, 1-(4-bromophenyl)-3-[(2-hydroxyphenyl)amino]-2-propen-1-one, 5-[4-(4-morpholinyl)-3-nitrobenzylidene]-2-thioxo-1,3-thiazolidin-4-one, 5-(5-bromo-2-methoxybenzylidene)-3-ethyl-2-thioxo-1,3-thiazolidin-4-one, [3-amino-6-(3-pyridinyl)thieno[2,3-b]pyridin-2-yl](phenyl)methanone, 3-iodo-N'-[(2-methyl-1H-indol-3-yl)methylene]benzohydrazide, N,N'-bis(2-acetylphenyl)tetrahydro-2,5-thiophenedicarboxamide, 2-[2-(4-chlorophenyl)-2-oxoethylidene]-1,3-thiazolidin-4-one, ethyl 4-{4-[4-(4-morpholinyl)benzylidene]-3,5-dioxo-1-pyrazolidinyl}benzoate, 3-iodo-1-[(1H-1,2,4-triazol-3-ylimino)methyl]-6,7,8,9-tetrahydrodibenzo[b,d]furan-2-ol, 10-hydroxy-1,2-dihydro-12H-benzo[4,5]isoquino[2,1-a]cyclopenta[gh]perimidin-12-one, or 1-benzoyl-3-phenyl-5-(trifluoromethyl)-4,5-dihydro-1H-pyrazol-5-ol.

42. The honeybee repellent according to any one of embodiments 1-39, wherein the honeybee repellent is not 3-bromo-7,8-diethoxy-4-methyl-6-nitro-2H-chromen-2-one, 4-hydroxy-3-[2-(4-hydroxyphenyl)-2,3-dihydro-1,5-benzothiazepin-4-yl]-6-methyl-2H-pyran-2-one, 6-(4-iodophenyl)imidazo[2,1-b][1,3]thiazole, 4-(2-furylmethylene)-2-(4-methylphenyl)-1,3-oxazol-5(4H)-one, 2-(3-bromophenyl)-2-oxoethyl benzoate, 2-anilino-8-quinolinol, (4-amino-3-nitrophenyl)(phenyl)methanone, N-[2-(aminocarbonyl)phenyl]-2-naphthamide, N'-(2-bromo-5-methoxybenzylidene)-2-(4-ethylphenoxy)acetohydrazide, 9H-fluoren-9-one thiosemicarbazone, 5-(4-nitrophenyl)-2,3,5,6-tetrahydrobenzo[a]phenanthridin-4(1H)-one, N'-(4-bromo-5-methyl-2-oxo-1,2-dihydro-3H-indol-3-ylidene)spiro[2.3]hexane-1-carbohydrazide, 2-[4-(allyloxy)-6-methyl-2-pyrimidinyl]phenol, 2-[6-phenyl-2-(1-piperazinyl)-4-pyrimidinyl]phenol, 4-{[(9-ethyl-9H-carbazol-3-yl)methylene]amino}benzamide, ethyl 1-amino-3-isopropyl-3,4-dihydro-2-naphthalenecarboxylate, ethyl [(4-oxo-3-phenyl-4,6-dihydro-3H-spiro[benzo[h]quinazoline-5,1'-cyclopentan]-2-yl)thio]acetate, 1-(3,6-dichloro-9H-carbazol-9-yl)-3-(4-morpholinyl)-2-propanol, 1-(3,6-dibromo-9H-carbazol-9-yl)-3-(4-morpholinyl)-2-propanol, 3-[3-(3,6-dichloro-9H-carbazol-9-yl)-2-hydroxypropyl]-1,3-thiazolidine-2,4-dione, N-(3,4-dihydro-1(2H)-quinolinylcarbonothioyl) benzamide, 2-(benzoylamino)-N-(4-chlorophenyl)benzamide, 1-(1-adamantyl)-N-mesityl-2-piperidinecarboxamide hydrochloride, 1-(4-methoxy-2,3-dimethylbenzyl)-4-(3-phenyl-2-propen-1-yl)piperazine, 1-phenyl-1-propanone N-(3-methylphenyl)thiosemicarbazone, N-(4-nitrophenyl)-1H-indol-3-amine, (3-amino-6-phenylthieno[2,3-b]pyridin-2-yl)(phenyl) methanone, 4-(1H-pyrrol-1-yl)-5,6,7,8-tetrahydro[1]benzothieno [2,3-d]pyrimidine, 4-[2-(4-nitrophenyl) vinyl]phenol, 2,2,4-trimethyl-1,2-dihydro-6-quinolinyl 3-methoxybenzoate, 7-(diethylamino)-4-methyl-3-nitro-2H-chromen-2-one, (4-bromo-3-chlorophenyl)(4-ethoxybenzylidene)amine, 4-[4-nitro-3-(2-phenoxyethoxy)phenyl]morpholine, 3-{[(9-ethyl-9H-carbazol-3-yl)methylene]amino}benzamide, N~1~-(9-anthrylmethylene)-1H-tetrazole-1,5-diamine, N-phenyl-N'-[2-(phenylethynyl)phenyl]urea, (9-anthrylmethylene)(3-nitrophenyl)amine, 2,4-di-tert-butyl-6-[(methylimino)methyl]phenol, N'-[(2-chlorobenzoyl)oxy]benzenecarboximidamide, N-(3-chloro-2-methylphenyl)-2-naphthalenesulfonamide, 2-[2-(3,5-dimethyl-1H-pyrazol-1-yl)-6-phenyl-4-pyrimidinyl] phenol, 2-[4-(4-methoxy-2,5-dimethylbenzyl)-1-piperazinyl]ethanol, 2-(benzylthio)-5-(2-chlorophenyl)-1,3,4-oxadiazole, 2-[(4-bromobenzyl)thio]-5-phenyl-1,3,4-oxadiazole, 3-chloro-2-phenyl-4H-chromen-4-one, N-benzyl-2,5-dichloro-N-ethylbenzenesulfonamide, 4-fluoro-N-{[(2-methoxyphenyl)amino]carbonothioyl}benzamide, 3-[(4-chlorobenzoyl)amino]propyl 4-chlorobenzoate, methyl 3-[(4-fluorobenzoyl)amino]-2-butenoate, 1-(4-methoxyphenyl)-3-(1-naphthyl)-2-propen-1-one, 6-{2-[5-(3-chlorophenyl)-2-furyl]vinyl}-4-(trifluoromethyl)-2(1H)-pyrimidinone, 9-amino-7H-benzimidazo[2,1-a]benzo[de]isoquinolin-7-one, N-benzyl-2-phenyl-N-(3-pyridinylmethyl)ethanamine, (3,4-difluorophenyl)[3-(4-methoxyphenyl)-1-methylpropyl]amine, 1-(4-chlorophenyl)-3-(2-hydroxyphenyl)-1,3-propanedione, N-(2-methylphenyl)-9-oxo-9H-fluorene-1-carboxamide, N-[2-(4-chlorophenoxy)ethyl]-5-(3-methyl-1-piperazinyl)-2-nitroaniline, 2-({[4-(benzylamino)phenyl]imino}methyl)-4-bromophenol, 3-methyl-1-phenyl-1H-pyrazole-4,5-dione 4-[(3-hydroxyphenyl)hydrazone], ethyl methyl 4-(4-bromophenyl)-2,6-dimethyl-1,4-dihydro-3,5-pyridinedicarboxylate, benzyl 2-methyl-4-(4-methylphenyl)-5-oxo-1,4,5,6,7,8-hexahydro-3-quinolinecarboxylate, 2-cyclohexyl-1H-naphtho[2,3-g]indazole-3,6,11(2H)-trione, 2-phenoxyethyl 4-(3-fluorophenyl)-6-methyl-2-oxo-1,2,3,4-tetrahydro-5-pyrimidinecarboxylate, 1,3-naphthalenediyl bis(2-methylpropanoate), 7-methyl-3-(4-methylbenzoyl)-4H-chromen-4-one, 2-[2-(2-aminophenyl)vinyl]-5,7-dimethyl-8-quinolinol, 2,6-diphenyl-4H-1,3-dioxin-4-one, 3-allyl-5-(2-hydroxy-3-nitrobenzylidene)-2-thioxo-1,3-thiazolidin-4-one, 3,5-diphenyl-1-(trifluoroacetyl)-4,5-dihydro-1H-pyrazole, 5-(2-chloro-5-nitrobenzylidene)-2-[(2-chlorophenyl)imino]-1,3-thiazolidin-4-one, 2,6-di-tert-butylbenzo-1,4-quinone 4-thiosemicarbazone, 2-ethyl-1-[(7-methyl-2-naphthyl)sulfonyl]piperidine, 5-benzyl-3-bromo-2-hydroxybenzaldehyde, 3-[5-(2-nitrophenyl)-2-furyl]-1-phenyl-2-propen-1-one, 2-(1,3-benzothiazol-2-ylthio)-1-(3-nitrophenyl)ethanone, isonicotinaldehyde diphenylhydrazone, N'-(2-hydroxy-3-methoxybenzylidene)-2-[(2-methylphenyl)amino] acetohydrazide (non-preferred name), 5-(1,3- benzodioxol-5-ylmethylene)-3-(1,5-dimethyl-3-oxo-2-phenyl-2,3-dihydro-1H-pyrazol-4-yl)-2-thioxo-1,3-thiazolidin-4-one, N'-{[5-(2,3-dichlorophenyl)-2-furyl]methylene}isonicotinohydrazide, 1-[3-(3,6-dibromo-9H-carbazol-9-yl)-2-hydroxypropyl]-2,5-pyrrolidinedione, N'-{[5-(3-chloro-4-methoxyphenyl)-2-furyl]methylene}-2-pyridinecarbohydrazide, N'-{[5-(4-bromophenyl)-2-furyl]methylene}-2-[(4-methylphenyl)amino]acetohydrazide, 2-[(1-bromo-2-naphthyl)oxy]-N'-(2-hydroxy-5-methoxybenzylidene) butanohydrazide, 1-[3-(3,6-dichloro-9H-carbazol-9-yl)-2-hydroxypropyl]-2,5-pyrrolidinedione, N-(4-chloro-2,5-dimethoxyphenyl)-2-phenoxybutanamide, N-[2-(aminocarbonyl)phenyl]-3-chloro-1-benzothiophene-2-carboxamide, N-(2-furylmethyl)-4-hydroxy-1-(3-methylbutyl)-2-oxo-1,2-dihydro-3-quinolinecarboxamide, methyl 5-{[(4-bromophenyl)amino]sulfonyl}-2-chlorobenzoate, 3-allyl-5-{3-[(4-nitrobenzyl) oxy]benzylidene}-2-thioxo-1,3-thiazolidin-4-one, N-[3-(1-piperidinylcarbonyl)-5,6,7,8-tetrahydro-4H-cyclohepta[b]thien-2-yl]benzamide, 2-(2-fluorobenzylidene)-6-methoxy-3,4-dihydro-1(2H)-naphthalenone, 2-(ethylthio)ethyl 4-(2-chlorophenyl)-6-methyl-2-oxo-1,2,3,4-tetrahydro-5-pyrimidinecarboxylate, 2-{3-[4-(9H-fluoren-9-yl)-1-piperazinyl]-3-oxopropyl}-1H-isoindole-1,3(2H)-dione, 3-(5-bromo-2-methoxyphenyl)-1-(3,4-dimethoxyphenyl)-2-propen-1-one, N-[(8-quinolinylamino)carbonothioyl]-2-thiophenecarboxamide, 1,2,3-trichloro-4-(isopropylamino) anthra-9,10-quinone, 3-methyl-6-(1-piperidinyl)-3H-naphtho[1,2,3-de]quinoline-2,7-dione, 3,4-dimethylphenyl 2-chlorobenzoate, spiro[cyclopentane-1,6'-isoquino[1,2-b]quinazolin-8'(5'H)-one, 1-benzoyl-5-(2-hydroxyphenyl)-3-(trifluoromethyl)-4,5-dihydro-1H-pyrazol-5-ol, 1-(4-methoxybenzoyl)-3-phenyl-5-(trifluoromethyl)-4,5-dihydro-1H-pyrazol-5-ol, 4-hydroxy-1-methyl-2-oxo-N-(1-phenylethyl)-1,2-dihydro-3-quinolinecarboxamide, 3-(4-chlorophenyl)-1-(3-pyridinylcarbonyl)-5-(trifluoromethyl)-4,5-dihydro-1H-pyrazol-5-ol, 4-bromo-N'[2-(trifluoroacetyl)-1-cyclopenten-1-yl]benzohydrazide, 5-{2-[(2,4-dichlorobenzyl)oxy]-3-methoxybenzylidene}-2-imino-1,3-thiazolidin-4-one, ethyl 2-{[(acetylamino)carbonothioyl]amino}-4-phenyl-3-thiophenecarboxylate, N'-[1-(1,3-dioxo-2,3-dihydro-1H-inden-2-yl)ethylidene]-3-hydroxy-2-naphthohydrazide, 9-methyl-2-phenyl-9H-imidazo[1,2-a]benzimidazole-3-carbaldehyde, 2-(4-bromophenyl)-3-[(4-nitrophenyl)sulfonyl]-1,3-thiazolidine, 9-amino-7H-benzimidazo[2,1-a]benzo[de]isoquinolin-7-one, 1-(4-methoxyphenyl)-3-(1-methyl-1H-indol-3-yl)-2-propen-1-one, N-methyl-N-[(6-nitro-1,3-benzodioxol-5-yl)methyl]-2-(2-pyridinyl)ethanamine, 4-[(6-nitro-1,3-benzodioxol-5-yl)methyl] thiomorpholine, 1,1'-(1,4-phenylene)bis[3-(1H-indol-3-yl)-2-propen-1-one], 1-(4-biphenylyl)-3-(1H-indol-3-yl)-2-propen-1-one, 1-(1,3-benzodioxol-5-ylmethyl)-4-(4,5-dimethoxy-2-nitrobenzyl) piperazine, 1-methyl-4-[(6-nitro-1,3-benzodioxol-5-yl)methyl]piperazine, or any combination thereof.

43. A composition comprising a compound according to any one of embodiments 1-42.
44. The composition according to embodiment 43, wherein the composition comprises a two or more different compound according to any one of embodiments 1-42, three or more different compound according to any one of embodiments 1-42, four or more different compound according to any one of embodiments 1-42, or five or more different compound according to any one of embodiments 1-42.
45. The composition according to embodiments 43 and 44, wherein the composition further comprises a solvent, a wetting agent, an emulsifying agent, a carrier, a diluent, or a dispersing agent.
46. The composition according to embodiments 43-45, wherein the composition is a liquid form or a solid form.
47. The composition according to embodiments 43-46, wherein the composition further comprises one or more an adhesive, a solvent, a wetting agent, an emulsifying agent, a carrier, a diluent, a dispersing agent an insecticide, a pesticide, a fungicide, a fertilizer of a micronutrient or macronutrient nature, a herbicide, a feeding inhibitor, an insect molting inhibitor, an insect mating inhibitor, an insect maturation inhibitor, a nematocide, a nutritional or horticultural supplement, a larvicide, a seed, or any combination thereof.
48. The composition according to embodiment 47, wherein the composition further comprises an insecticide.
49. The composition according to embodiment 48, wherein the insecticide is an organochlorine, an organophosphate, a carbamate, a pyrethroid, or a neonicotinoid.
50. The composition according to embodiment 49, wherein the neonicotinoid is Acetamiprid, Clothianidin, Imidacloprid, Nitenpyram, Nithiazine, Thiacloprid, or Thiamethoxam.
51. A use of a honeybee repellent according to any one of embodiments 1-42 or a composition according to any one of embodiments 43-50 to repel a honeybee from a location by applying the compound or the composition to the location.
52. A use of a honeybee repellent according to any one embodiments 1-42 or a composition according to any one of embodiments 43-50 to repel a honeybee from foraging and/or collecting nectar from a flower of a plant by applying the compound or the composition to the plant or in a location in the vicinity of the plant.
53. A use of a honeybee repellent according to any one of embodiments 1-42 or a composition according to any one of embodiments 43-50 to repel a honeybee from a structure by applying the compound or the composition to the structure or in a location in the vicinity of the structure.
54. A method of repelling a honeybee from a location, the method comprising the step of applying a honeybee repellent according to any one of embodiments 1-42 or a composition according to any one of embodiments 43-50 to a location, wherein application of the compound or the composition to the location repels a honeybee from the location.
55. A method of repelling a honeybee from a plant, the method comprising the step of applying a honeybee repellent according to any one of embodiments 1-42 or a composition according to any one of embodiments 43-50 to a plant or in a location in the vicinity of the plant, wherein application of the compound or the composition to the location repels a honeybee from foraging and/or collecting nectar from a flower of the treated plant.
56. A method of repelling a honeybee from a structure, the method comprising the step of applying a honeybee repellent according to any one of embodiments 1-42 or a composition according to any one of embodiments 43-50 to a structure or in a location in the vicinity of the structure, wherein application of the compound or the composition to the structure repels a honeybee from the structure.

57. A seed composition comprising a seed and a honeybee repellent according to any one of embodiments 1-42 or a composition according to any one of embodiments 43-50.
58. A seed composition of embodiment 57, wherein the composition further comprises one or more of an insecticide, a pesticide, a fungicide, a fertilizer of a micronutrient or macronutrient nature, a herbicide, a feeding inhibitor, an insect molting inhibitor, an insect mating inhibitor, an insect maturation inhibitor, a nematocide, a nutritional or horticultural supplement, a larvicide, a seed, or any combination thereof
59. A device comprising a honeybee repellent according to any one of embodiments 1-42 or a composition according to any one of embodiments 43-50.

EXAMPLES

The following non-limiting examples are provided for illustrative purposes only in order to facilitate a more complete understanding of the disclosed subject matter. These examples should not be construed to limit any of the embodiments described in the present specification, including those pertaining to the compounds, compositions, pharmaceutical kits, methods or uses of repelling honeybees.

Example 1

Testing of Candidate Compounds Using Binding Assay

To identify a honeybee repellent disclosed herein, candidate compounds were screened based upon the fact that 2-heptanone is an established repellent of bees. 2-heptanone is thought to mediate its behavioral response through binding to a specific odorant-binding protein called OBP2. Therefore compounds that bind OBP2 have the potential to act as odor "mimics" of 2-heptanone. By utilizing a fluorescent-quench, ligand-protein-binding assay, 30,000 compounds from the DIVERSET® library (ChemBridge Corp., San Diego, Calif.), a chemical library, were screened and over 150 candidate compounds were isolated that bind OBP2 (Table 1). Such assays are generally known in the art. See, e.g., Briand, et al., Ligand-Binding Properties and Structural Characterization of a Novel Rat Odorant-Binding Protein Variant, Eur. J. Biochem. 267(10): 3079-3089 (2000); Briand, et al., Ligand Binding and Physico-Chemical Properties of ASP2, A Recombinant Odorant-Binding Protein From Honeybee (*Apis mellifera* L.), Eur. J. Biochem. 268(3): 752-760 (2001); Briand, et al., Characterization of a Chemosensory Protein (ASP3c) from Honeybee (*Apis mellifera* L.) as a Brood Pheromone Carrier, Eur. J. Biochem. 269(18): 4586-4596 (2002), each of which is hereby incorporated by reference in its entirety.

Example 2

Testing of Candidate Compounds Using the PER Assay

To determine whether a living honeybee can recognize a candidate compound, these compounds were tested using a proboscis extension response (PER) assay using classical conditioning approaches. Proboscis extension response conditioning is a case of appetitive learning, in which bees learn to associate odor stimuli with sucrose reward in the laboratory. In this case, bees were conditioned to produce a PER to 2-heptanone as the conditioned stimulus and a sugar reward as the unconditioned stimulus. These trained bees were then exposed to an odor pulse of a candidate compound to test whether a candidate compound would also produce a PER. If the candidate compound "mimics" 2-heptanone then the honeybee will extend its proboscis.

For conditioning procedures, *Apis mellifera* Carniolan foraging worker honeybees were obtained from a local apiary (typically 60 bees per shipment). The honeybees were held overnight in insect cages with food and water freely available, in an environmentally controlled room on a light cycle similar to the ambient cycle at the time of the assay.

For conditioning procedures, all tests were done in an odorant delivery apparatus set inside a fume hood. The apparatus comprised a set of open-ended, horizontal, 3 cm diameter by 10 cm long plastic tubes. Each tube was designed where a honeybee could be positioned at the distal end of a tube, with the opening at the other end of the tube located proximal to an inlet of the fume hood. To deliver an odorant, room air was pumped by a diaphragm pump through a particle filter via 0.25 inch plastic tubing at approximately 0.7 m/sec. The air flow passes into the headspace above an odorant (0.5% [v/v] 2-heptanone dissolved in odorless light paraffin oil) contained in a 100 mL bottle. The headspace air then passes through another plastic tube to a manifold of 4-way valves, each of which was attached near the proximal end of a plastic tube containing a bee. Each bee was exposed separately for a desired time period to the odorant by opening and closing the appropriate valve. When each valve was closed, the odor was flushed away immediately by the continuous fume hood air stream.

To train a honeybee to respond to a conditioned and unconditioned stimuli, bees were placed, without anesthesia, in individual 1.5 mL micro-centrifuge holding tubes and held overnight without access to food or water. The holding tubes containing the starved bees were placed in racks in groups of eight. One rack at a time was placed behind the odorant delivery apparatus so that each bee's head is centered at the distal end of a horizontal plastic tube. Each bee was exposed to the 2-heptanone odorant alone for four seconds, and then while being fed an 80% sucrose solution for and additional three seconds. The sucrose solution was delivered on a piece of saturated filter paper held in forceps. The wet paper was touched to the bee's antennae if the bee did not immediately extend its proboscis (which usually happens in a fraction of a second after the sucrose solution comes near the bee's head). Positive and negative responses were recorded. A positive PER was scored when a bee extended its proboscis before the sucrose appeared. In a typical trial, 48 individual bees were subjected to conditioning. Six rounds of training were done before testing began, and typically a majority of the bees were successfully conditioned by the second or third round of training.

After conditioning, honeybees were tested with the candidate compounds the same day or on the following day or, most commonly, both. When held overnight, bees were fed with sucrose and kept in their holding tubes. When tested the day after training, bees were given one or more rounds of conditioning with 2-heptatone to refresh their memories. Candidate compounds stocks were made at 5% (w/v) in polyoxyethylene octyl phenyl ether (TRITON® X-100), a non-ionic detergent/surfactant, and stored at 4° C. This detergent is similar to substances used as carriers for a variety of commercial pest-control agents, can act as a solvent for both hydrophilic and hydrophobic substances, and is itself nearly odorless. Test solutions were made fresh daily by mixing stock solutions with water for a final compound concentration of 0.5%. A solution of 0.5% 2-heptanone in paraffin oil was used as a positive control. Both water and 15% polyoxyethylene octyl phenyl ether (TRITON® X-100) in water served as negative controls to eliminate false positives.

For candidate compound testing experiments, a single 3 cm length of 3 cm diameter plastic tube is positioned horizontally in a holder so that air is drawn through it at about 0.7 m/sec. Holding tubes containing a trained honeybee were positioned in racks as for the conditioning procedure. The rack was then moved sequentially behind the tube so that each bee's head was directly behind the rear end of tube for the test. The test compounds and controls were presented on a saturated piece of filter paper held at the front end of the 3 cm tube. Bees in each rack were exposed sequentially to a given candidate compound or control for four seconds and the results recorded. After bees were tested with one compound, the process was repeated for the next candidate compound using a clean tube and testing implements. The order of testing was randomized for each day's test and generally 5-6 different candidate compounds were tested in a single day along with 3 controls. Only bees giving a PER with 2-heptanone, but not with the negative controls were counted in calculating the percent of bees testing positive to each compound (Table 2). Generally about half of the total bees subjected to conditioning exhibited a PER with the 2-heptanone positive control, and only a very small number of these respond to the negative controls. If a given cohort of bees were tested for two consecutive days, they were tested with two separate sets of candidate compounds to maximize the number of individual bees tested with each compound. In a few cases where a single cohort of bees was tested twice with the same compounds. In this case, the results were averaged and the average was used in the calculation of the percent of positives. Table 2 shows the results from the PER assay for 66 candidate compounds. Compounds are ranked in order of the percent 2-heptanone-positive honeybees that were positive to the test compound and negative to both water and 15% polyoxyethylene octyl phenyl ether (TRITON® X-100) controls.

TABLE 2

| OBP2 Binding and Proboscis Extension Response (PER) Assay | | | | |
|---|---|---|---|---|
| | Candidate Compound | 2-heptanone positive bees | 2-heptanone positive bees testing positive | OBP2 binding characteristic |
| No. | Name | (n) | to compound | of compound |
| 66 | 2-hydroxy-1-naphthaldehyde 2-pyridinylhydrazone | >20 | 24.4% | Moderate |
| 67 | 4-(4,6-diphenyl-1,2-dihydro-1,3,5-triazin-2-yl)-2-methoxyphenol | >20 | 26.5% | Moderate |
| 68 | N,N'-bis(2-acetylphenyl)tetrahydro-2,5-thiophenedicarboxamide | >20 | 20.8% | Moderate |
| 71 | ethyl [(4-oxo-3-phenyl-4,6-dihydro-3H-spiro[benzo[h]quinazoline-5,1'-cyclopentan]-2-yl)thio]acetate | >20 | 19.1% | Moderate |
| 72 | 3-[3-(3,6-dichloro-9H-carbazol-9-yl)-2-hydroxypropyl]-1,3-thiazolidine-2,4-dione | >20 | 2.3% | Moderate |
| 73 | 1-benzoyl-5-(2-hydroxyphenyl)-3-(trifluoromethyl)-4,5-dihydro-1H-pyrazol-5-ol | >20 | 8.3% | Moderate |
| 74 | 1-{[(4-iodophenyl)imino]methyl}-2-naphthol | >20 | 25.0% | Moderate |
| 75 | [3-amino-6-(3-pyridinyl)thieno[2,3-b]pyridin-2-yl](phenyl)methanone | >20 | 25.0% | Moderate |
| 77 | 4-(1H-pyrrol-1-yl)-5,6,7,8-tetrahydro[1]benzothieno[2,3-d]pyrimidine | >20 | 14.3% | Moderate |
| 78 | ethyl 2-{[(acetylamino)carbonothioyl]amino}-4-phenyl-3-thiophenecarboxylate | >20 | 7.7% | Moderate |
| 79 | 2-[(2-ethoxybenzylidene)amino]-1H-isoindole-1,3(2H)-dione | >20 | 23.1% | Moderate |
| 80 | 4-phenoxy-2-phenyl-6-(1H-pyrazol-1-yl)pyrimidine | >20 | 20.0% | Moderate |
| 81 | ethyl 2-(benzoylamino)-5-ethyl-3-thiophenecarboxylate | >20 | 37.5% | Moderate |
| 82 | 2-[(2-hydroxy-3,5-diiodobenzylidene)amino]-4,6-dimethylphenol | >20 | 6.4% | Moderate |
| 83 | 2-bromo-4-chloro-6-[(2-pyridinylimino)methyl]phenol | >20 | 47.7% | Moderate |
| 84 | (2,5-dimethylphenyl)[(2-methoxy-1-naphthyl)methylene]amine | >20 | 27.9% | Moderate |
| 85 | 5-[4-(4-morpholinyl)-3-nitrobenzylidene]-2-thioxo-1,3-thiazolidin-4-one | >20 | 18.0% | Moderate |
| 86 | 5-[4-(4-morpholinyl)-3-nitrobenzylidene]-2-thioxo-1,3-thiazolidin-4-one | >20 | 38.1% | Moderate |
| 87 | 2-({[4-(benzylamino)phenyl]imino}methyl)-4-bromophenol | >20 | 9.5% | Moderate |
| 88 | 2-cyclohexyl-1H-naphtho[2,3-g]indazole-3,6,11(2H)-trione | >20 | 14.3% | Moderate |
| 89 | 2-{[(5-ethyl-2-hydroxyphenyl)imino]methyl}-4,6-diiodophenol | >20 | 33.3% | Moderate |
| 90 | 2-[2-(2-aminophenyl)vinyl]-5,7-dimethyl-8-quinolinol | >20 | 17.0% | Moderate |
| 91 | 3-allyl-5-(2-hydroxy-3-nitrobenzylidene)-2-thioxo-1,3-thiazolidin-4-one | >20 | 17.3% | Moderate |

TABLE 2-continued

OBP2 Binding and Proboscis Extension Response (PER) Assay

| Candidate Compound | | 2-heptanone positive bees (n) | 2-heptanone positive bees testing positive to compound | OBP2 binding characteristic of compound |
|---|---|---|---|---|
| No. | Name | | | |
| 92 | isonicotinaldehyde diphenylhydrazone | >20 | 7.0% | Moderate |
| 93 | 1-[3-(3,6-dibromo-9H-carbazol-9-yl)-2-hydroxypropyl]-2,5-pyrrolidinedione | >20 | 14.0% | Moderate |
| 94 | N-[2-(aminocarbonyl)phenyl]-3-chloro-1-benzothiophene-2-carboxamide | >20 | 16.7% | Moderate |
| 95 | N-(2-furylmethyl)-4-hydroxy-1-(3-methylbutyl)-2-oxo-1,2-dihydro-3-quinolinecarboxamide | >20 | 7.3% | Moderate |
| 96 | 3-iodo-1-[(1H-1,2,4-triazol-3-ylimino)methyl]-6,7,8,9-tetrahydrodibenzo[b,d]furan-2-ol | >20 | 28.6% | Moderate |
| 97 | N-{3-[(diethylamino)carbonyl]-5,6,7,8-tetrahydro-4H-cyclohepta[b]thien-2-yl}-2-furamide | >20 | 21.1% | Moderate |
| 98 | N-(3-{[(4-methylphenyl)amino]carbonyl}-5,6,7,8-tetrahydro-4H-cyclohepta[b]thien-2-yl)-2-furamide | >20 | 21.6% | Moderate |
| 99 | N-[3-(1-piperidinylcarbonyl)-5,6,7,8-tetrahydro-4H-cyclohepta[b]thien-2-yl]benzamide | >20 | 29.0% | Moderate |
| 100 | 2-{3-[4-(9H-fluoren-9-yl)-1-piperazinyl]-3-oxopropyl}-1H-isoindole-1,3(2H)-dione | >20 | 10.4% | Moderate |
| 101 | ethyl 4-{4-[4-(4-morpholinyl)benzylidene]-3,5-dioxo-1-pyrazolidinyl}benzoate | >20 | 20.9% | Moderate |
| 102 | 2-{3-[4-(9H-fluoren-9-yl)-1-piperazinyl]-3-oxopropyl}-1H-isoindole-1,3(2H)-dione | >20 | 10.5% | Moderate |
| 103 | 3-iodo-N'-[(2-methyl-1H-indol-3-yl)methylene]benzohydrazide | >20 | 32.4% | Moderate |
| 105 | 1,2-naphthalenedione 1-(2,3-dihydro-1,4-benzodioxin-6-ylhydrazone) | >20 | 24.3% | Moderate |
| 106 | 2-(benzylthio)-5-(2-chlorophenyl)-1,3,4-oxadiazole | >20 | 7.3% | Moderate |
| 107 | 4-fluoro-N-{[(2-methoxyphenyl)amino]carbonothioyl}benzamide | >20 | 5.1% | Moderate |
| 108 | 6-{2-[5-(3-chlorophenyl)-2-furyl]vinyl}-4-(trifluoromethyl)-2(1H)-pyrimidinone | >20 | 16.2% | Moderate |
| 109 | 9-amino-7H-benzimidazo[2,1-a]benzo[de]isoquinolin-7-one | >20 | 12.1% | Moderate |
| 110 | 1-(4-bromophenyl)-3-[(2-hydroxyphenyl)amino]-2-propen-1-one | >20 | 31.4% | Moderate |
| 111 | 2-[2-(4-chlorophenyl)-2-oxoethylidene]-1,3-thiazolidin-4-one | >20 | 30.6% | Moderate |
| 112 | 10-hydroxy-1,2-dihydro-12H-benzo[4,5]isoquino[2,1-a]cyclopenta[gh]perimidin-12-one | >20 | 44.4% | Moderate |
| 113 | N'-{[5-(2,3-dichlorophenyl)-2-furyl]methylene}isonicotinohydrazide | >20 | 11.1% | Moderate |
| 114 | N'-{[5-(3-chloro-4-methoxyphenyl)-2-furyl]methylene}-2-pyridinecarbohydrazide | >20 | 22.2% | Moderate |
| 115 | 5-(5-bromo-2-methoxybenzylidene)-3-ethyl-2-thioxo-1,3-thiazolidin-4-one | >20 | 40.0% | Moderate |
| 116 | 5-(5-bromo-2-hydroxybenzylidene)-3-ethyl-2-thioxo-1,3-thiazolidin-4-one | >20 | 25.0% | Moderate |
| 117 | N-[(8-quinolinylamino)carbonothioyl]-2-thiophenecarboxamide | >20 | ND | Moderate |
| 118 | 5-{2-[(2,4-dichlorobenzyl)oxy]-3-methoxybenzylidene}-2-imino-1,3-thiazolidin-4-one | >20 | ND | Moderate |
| 119 | 1-benzoyl-3-phenyl-5-(trifluoromethyl)-4,5-dihydro-1H-pyrazol-5-ol | >20 | 60.0% | Moderate |

Low, indicates no detectable binding to OBP2.
Moderate, indicates that 50% or less of the compound bound to OBP2.
Strong, indicates that 51% or more of the compound bound to OBP2.
ND, Not determined.

Example 3

Testing of Candidate Compounds Using Choice Test

To determine whether living honeybees will choice to move towards a source of a candidate compound, these compounds will be assayed using a choice test in a free-flight box apparatus.

All tests will be done in a free-flight box apparatus. The apparatus comprises a 244 cm long×46 cm deep×30 cm high clear plastic box including two equally-sized independent testing chambers, each with 10 cm diameter air inlets that admit filtered room air, separated by a smaller central chamber with a screened air outlet to each testing chamber. Air can be pulled through the sealed box via a 10 cm diameter duct from the air outlet using an AQE Fume Fighter 500 fume extractor (BPA Air Quality Solutions, LLC, Charleston, S.C.), which removes the test odors using activated charcoal and HEPA filters. The box is housed in an environmentally controlled room with overhead illumination timed to correspond to the current ambient light cycle including 2 additional sets of lights timed to approximate crepuscular lighting conditions. The bottom of the apparatus will be lined with clean absorbent paper marked with a 4×9 grid pattern, forming 12 cm×12 cm squares with marked coordinates.

*Apis mellifera* Carniolan foraging worker honeybees will be obtained from a local apiary (typically 60 bees per shipment). Thirty honeybees will be put into each testing chamber and will be allowed to acclimate for 24 hours with food and water freely available. At the beginning of each test day all food will be removed from the test chamber, but water will be continually available throughout all tests. For each test, approximately 0.3 g of organic, raw orange blossom honey will be added to each clean small plastic weigh boat (Cole-Palmer). The honey boats will be placed in small plastic culture dishes, which will be distributed in the marked squares in the chambers. The positions of the dishes on the grid for a set of trials will be chosen to avoid the bees' preferred resting area so that they will have to find the food actively, but the same dish positions will be maintained for a given set of trials. We will use seven dishes of honey: six to which the bees will have access and a seventh that will have a screened lid. The honey in each boat will be weighed on an analytical balance before and after the test, with the screened sample as a control for evaporative loss. The fume extractor will be left off during the experimental trails, and will be turned on to clear the air after the test dishes are covered and removed from the chamber at the end of each trial.

Based on the observation that bees tend to return to dishes in the same position where they have fed before, each set of trials with each group of bees began with "Pattern Identification" tests to see which dishes lose the most weight, reflecting the most feeding. Once bees are consuming an acceptable amount in 10-15 min, typically in 1-2 trials, a set of test compound trials will begin. The test compound will be pipetted onto pieces of filter paper placed on the dish bottom below the boat containing a fresh, weighed honey sample so that the test compound will be inaccessible to the bees. We used 2 µL of a candidate compound at a concentration of 0.05-0.5%, in Triton X-100 or paraffin oil, on each of four pieces of filter paper per dish. The test-solution dishes will be set at the same positions as the one or two dishes favored in the preceding Pattern Identification trial. To eliminate interference from the solvent, the other dishes without the test substance will contain the same volume of the appropriate solvent on filter papers as the test solution dishes. The bees will be allowed to feed for 10-15 minutes. Bee movements will be recorded by a small, wide-angle digital video camcorder (HD Hero 960; GoPro, Halfmoon Bay, Calif.) placed on a tripod in front of the test chamber. The bees will be given a brief rest while the honey will be weighed and a second test will be begin with fresh dishes, except that the test compound-containing dish or dishes will be placed at whichever positions were most visited in the preceding test. Tests will be continued until the bees' feeding slowed significantly, typically in 2-4 trials. The bees will be then rested for 1-3 hours and a subsequent set of trials begun with another Pattern Identification. Tests were performed in both chambers simultaneously, with the same test compounds. Groups of bees can perform as many as nine tests in one day, with an average of about seven on the first day and somewhat fewer on subsequent days, usually for three days.

To validate the test system, the known honeybee repellent, 2-heptanone, at the concentration used in the PER assays was used as a positive control for repellency. In addition, neroli oil, a component of commercial honeybee attractants (swarm lures), will be used as a positive control for an attractant. Lastly, a dish containing food alone will be used as a control for the components in the solution minus the candidate compound. Candidate compounds with high PER scores as well as compounds with lower PER scores will be examined in order to correlated the results from the choice test. Using the criterion of reduction of feeding at dishes that are most visited in the preceding test, candidate compounds with high PER scores attracted honeybees as well as, or better, than 2-heptanone as repellents, while weaker performers in the PER assay are generally less effective repellents. The attractant effect of neroli oil will also be detected.

To determine whether a compound has an effect on the bees in the free flight box, we calculated the likelihood of bees returning to a dish that they had exhibited a preference for in the immediately preceding experiment. For each individual experiment, we considered a dish to be preferred if it was one of the two dishes from which the most honey was consumed. If two consecutive experiments were run in which no compounds were present, bees showed a 47.5% likelihood of returning to a preferred dish. We then calculated the likelihoods of bees returning to their preferred dishes with the compounds. These likelihoods were compared to the control likelihood of 47.5% using the Z-test (alpha=10%), where n is the total number of tests a honeybee returned to any test dish, nP is the number of tests a honeybee returned to a preferred test dish and P is the probability that a honeybee will return to a test dish and is calculated by dividing nP with n. Table 3 show the results obtained on selected candidate compounds. 2-heptone was used as a positive control for a honeybee repellant.

TABLE 3

Choice Test Assay

Candidate Compound

| No. | Name | n | nP | P | Z-score |
|---|---|---|---|---|---|
| — | 2-heptone | 510 | 217 | 0.425 | −2.256 |
| 66 | 2-hydroxy-1-naphthaldehyde 2-pyridinylhydrazone | 58 | 22 | 0.379 | −1.465 |
| 67 | 4-(4,6-diphenyl-1,2-dihydro-1,3,5-triazin-2-yl)-2-methoxyphenol | 28 | 9 | 0.321 | −1.631 |
| 68 | N,N'-bis(2-acetylphenyl)tetrahydro-2,5-thiophenedicarboxamide | 4 | 2 | 0.5 | 0.099 |
| 74 | 1-{[(4-iodophenyl)imino]methyl}-2-naphthol | 40 | 18 | 0.45 | −0.321 |
| 75 | [3-amino-6-(3-pyridinyl)thieno[2,3-b]pyridin-2-yl](phenyl)methanone | 24 | 13 | 0.542 | 0.650 |
| 79 | 2-[(2-ethoxybenzylidene)amino]-1H-isoindole-1,3(2H)-dione | 2 | 2 | 1 | 1.486 |
| 80 | 4-phenoxy-2-phenyl-6-(1H-pyrazol-1-yl)pyrimidine | 6 | 2 | 0.333 | −0.697 |
| 81 | ethyl 2-(benzoylamino)-5-ethyl-3-thiophenecarboxylate | 18 | 6 | 0.333 | −1.207 |
| 83 | 2-bromo-4-chloro-6-[(2-pyridinylimino)methyl]phenol | 36 | 10 | 0.278 | −2.374 |
| 86 | 5-[4-(4-morpholinyl)-3-nitrobenzylidene]-2-thioxo-1,3-thiazolidin-4-one | 32 | 8 | 0.25 | −2.553 |
| 89 | 2-{[(5-ethyl-2-hydroxyphenyl)imino]methyl}-4,6-diiodophenol | 18 | 5 | 0.278 | −1.679 |

Critical Z-score is 1.282, with a positive value indicative of an attractant and a negative score indicative of a repellant.

Example 4

Use of Honeybee Repellent in Conjunction with Insecticide

This example illustrates how to use a honeybee repellent disclosed herein to repel honeybees from an area where insecticides have also been applied in order to reduce honeybee mortality and avoid insecticide contamination of honey, beeswax, and other hive products.

At the start of a growing season, an almond tree grower delays the use of a nicotine-based insecticide like Clothianidin and Imidacloprid in order to minimize harmful effects of this insecticide on honeybees while these insects enter his almond tree orchards. While gathering nectar from the flowers of the almond trees, the honeybees pollinate the trees. Subsequently the grower does apply a nicotine-based insecticide like Clothianidin and Imidacloprid to his orchards. At the same or similar time, the grower also applies a honeybee repellent disclosed herein. The grower may periodically applies the repellant using the same schedule as that for the insecticide, or one based on the half-life of the honeybee repellent. The grower realizes typical yields of almonds, while at the same time his neighbor, who is a beekeeper, reports that his bee colonies are healthy and he has harvested an excellent yield of honey.

Example 5

Use of Honeybee Repellent to Increase Yields of Seedless Crops

This example illustrates how to use a honeybee repellent disclosed herein to prevent unwanted pollination of crop plants by honeybees where such pollination reduces the market value due to the resulting seeded crop.

At the start of a growing season, a mandarin orange grower applies a nicotine-based insecticide like Clothianidin and Imidacloprid. At the same or similar time, the grower also applies a honeybee repellent disclosed herein. The grower may periodically applies the repellant using the same schedule as that for the insecticide, or one based on the half-life of the honeybee repellent. The grower realizes excellent yields of seedless mandarin oranges. A beekeeper nearby reports that his bee colonies are healthy.

Example 6

Use of Honeybee Repellent to Increase Yields of Seedless Crops

This example illustrates how to use a honeybee repellent disclosed herein to prevent unwanted pollination of crop plants by honeybees where such pollination reduces the market value due to the resulting seeded crop.

At the start of a growing season, a tangerine grower applies a honeybee repellent disclosed herein. The grower may periodically apply the repellant based on its half-life. The grower realizes excellent yields of seedless tangerine. A beekeeper nearby reports that his bee colonies are healthy.

Example 7

Use of Honeybee Repellent to Control Honeybee Presence in Outdoor Area

This example illustrates how to use a honeybee repellent disclosed herein to keep away honeybees from outdoor areas where human activities are occurring and would be disrupted by honeybee presence, such as, e.g., an outdoor activity like a sporting event or picnic.

At the start of a Fourth of July picnic, a mother applies a honeybee repellent disclosed herein in the area where her family is setting up table and grill. The mother realizes that, unlike previous events of this nature, honeybees did not seem to bother her family while they were eating their lunch.

Example 8

Use of Honeybee Repellent to Control Honeybee Presence in Structure

This example illustrates how to use a honeybee repellent disclosed herein to keep away honeybees from man-made structures in order to prevent infestation of a colony, such as, e.g., a commercial building, a house, a shed, or other structure.

A man recently had an exterminator remove a bee colony that established a hive inside one of the ways of his house. This was a reoccurring problem as it had happened three previous two years as well. After removal, the exterminator applied a honeybee repellent disclosed herein and also explained to the homeowner that he should periodically apply the repellent in order to prevent a further infestation. The homeowner did as instructed. The next year honeybees did not establish a hive in the man's house.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A composition comprising a honeybee repellent and one or more of an adhesive, an insecticide, a pesticide, a fungicide, a fertilizer of a micronutrient or macronutrient nature, a herbicide, a feeding inhibitor, an insect molting inhibitor, an insect mating inhibitor, an insect maturation inhibitor, a nematocide, a nutritional or horticultural supplement, a larvicide, a seed, or any combination thereof, wherein the honeybee repellent is 2-hydroxy-1-naphthaldehyde 2-pyridinylhydrazone, 1-{[(4-iodophenyl)

imino]methyl}-2-naphthol, ethyl 2-(benzoylamino)-5-ethyl-3-thiophenecarboxylate, or a salt, polymorph, solvate, hydrate, or tautomer thereof.

2. The composition according to claim 1, wherein the composition further comprises a solvent, a wetting agent, an emulsifying agent, a carrier, a diluent, or a dispersing agent.

3. The composition according to claim 1, wherein the insecticide is an organochlorine, an organophosphate, a carbamate, a pyrethroid, or a neonicotinoid.

4. The composition according to claim 3, wherein the neonicotinoid is Acetamiprid, Clothianidin, Imidacloprid, Nitenpyram, Nithiazine, Thiacloprid, or Thiamethoxam.

5. The composition according to claim 1, wherein the honeybee repellent is

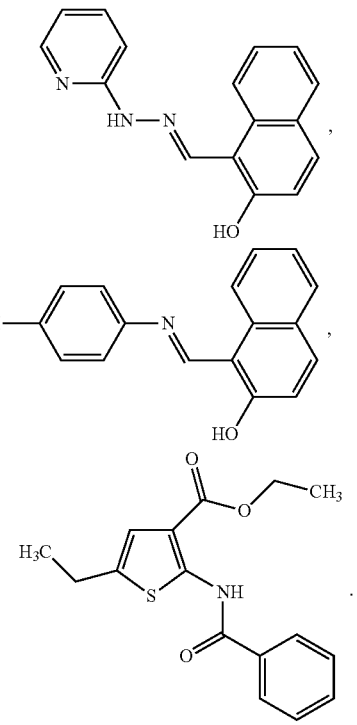

or

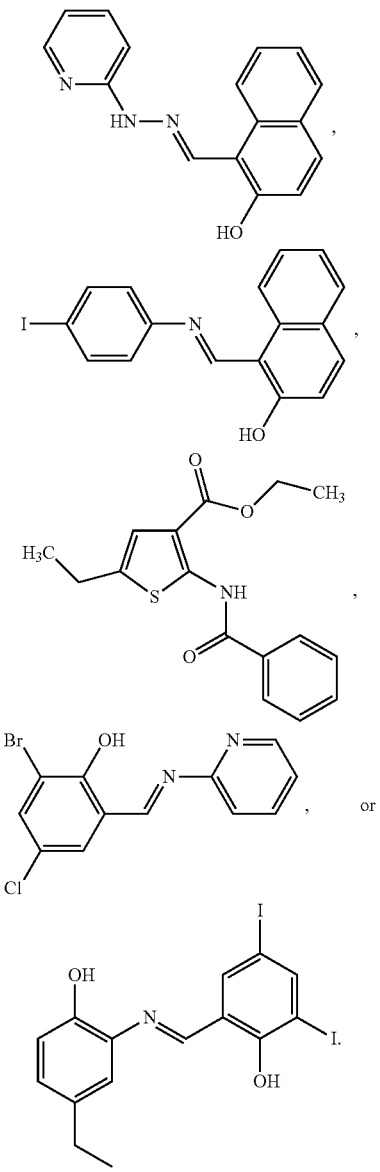

6. A method of repelling a honeybee from a structure or location, the method comprising the step of applying an effective amount of a honeybee repellent to the structure or the location, wherein application of the honeybee repellent to the structure or the location repels a honeybee from the structure or the location, wherein the honeybee repellent comprises 2-hydroxy-1-naphthaldehyde 2-pyridinylhydrazone, 1-{[(4-iodophenyl)imino]methyl}-2-naphthol, ethyl 2-(benzoylamino)-5-ethyl-3-thiophenecarboxylate, 2-bromo-4-chloro-6-[(2-pyridinylimino)methyl]phenol, 2-{[(5-ethyl-2-hydroxyphenyl)imino]methyl}-4,6-diiodophenol, or a salt, polymorph, solvate, hydrate, or tautomer thereof.

7. The method according to claim 6, wherein the honeybee repellent is

8. A method of repelling a honeybee from a structure or location, the method comprising the step of applying an effective amount of a composition to the structure or the location, wherein application of the composition to the structure or the location repels a honeybee from the structure or the location, wherein the composition comprises a honeybee repellent comprising 2-hydroxy-1-naphthaldehyde 2-pyridinylhydrazone, 1-{[(4-iodophenyl)imino]methyl}-2-naphthol, ethyl 2-(benzoylamino)-5-ethyl-3-thiophenecarboxylate, 2-bromo-4-chloro-6-[(2-pyridinylimino)methyl]phenol, 2-{[(5-ethyl-2-hydroxyphenyl)imino]methyl}-4,6-diiodophenol, or a salt, polymorph, solvate, hydrate, or tautomer thereof.

9. The method according to claim 8, wherein the honeybee repellent is

109

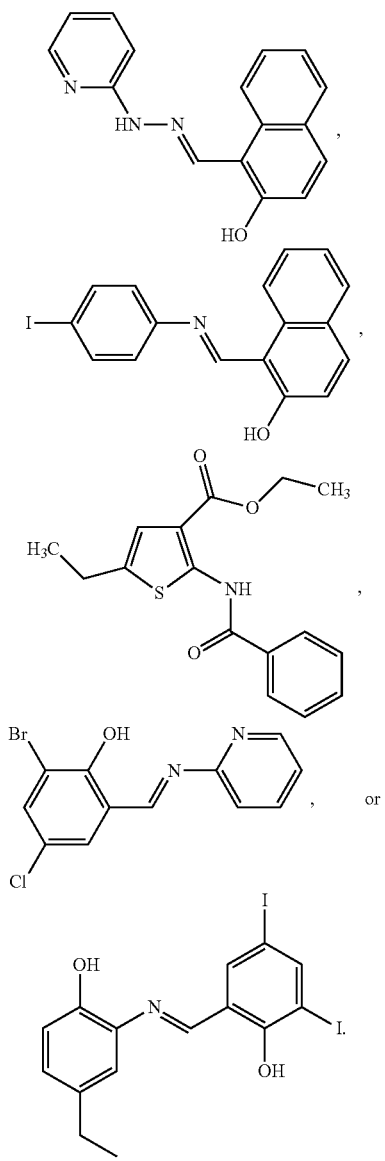

110

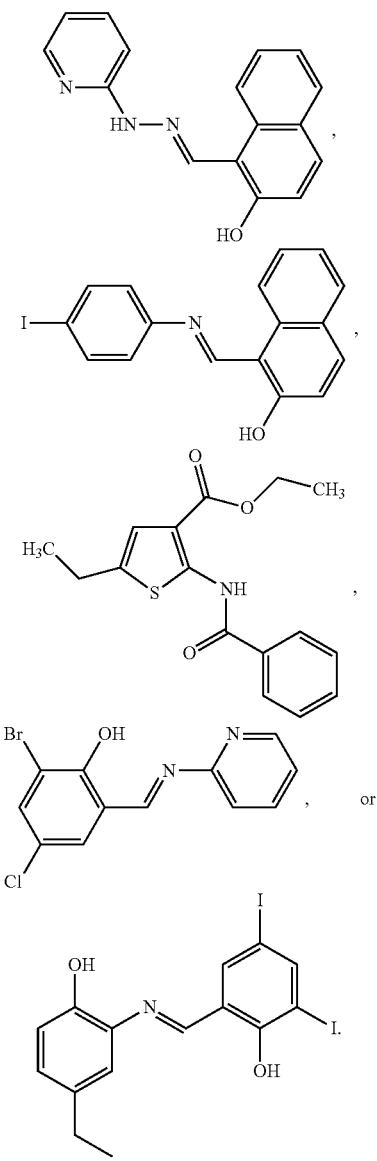

10. A method of repelling a honeybee from a plant, the method comprising the step of applying an effective amount of a honeybee repellent to the plant or in a location in the vicinity of the plant, wherein application of the honeybee repellent to the plant or the location repels a honeybee from foraging and/or collecting nectar from a flower of the treated plant or from a flower in the vicinity of the treated location, wherein the honeybee repellent comprises 2-hydroxy-1-naphthaldehyde 2-pyridinylhydrazone, 1-{[(4-iodophenyl)imino]methyl}-2-naphthol, ethyl 2-(benzoylamino)-5-ethyl-3-thiophenecarboxylate, 2-bromo-4-chloro-6-[(2-pyridinylimino)methyl]phenol, 2-{[(5-ethyl-2-hydroxyphenyl)imino]methyl}-4,6-diiodophenol, or a salt, polymorph, solvate, hydrate, or tautomer thereof.

11. The method according to claim 10, wherein the honeybee repellent is

12. A method of repelling a honeybee from a plant, the method comprising the step of applying an effective amount of a composition to the plant or in a location in the vicinity of the plant, wherein application of the honeybee repellent to the plant or the location repels a honeybee from foraging and/or collecting nectar from a flower of the treated plant or from a flower in the vicinity of the treated location, wherein the composition comprises a honeybee repellent comprising 2-hydroxy-1-naphthaldehyde 2-pyridinylhydrazone, 1{[(4-iodophenyl)imino]methyl}-2-naphthol, ethyl 2-(benzoylamino)-5-ethyl-3-thiophenecarboxylate, 2-bromo-4-chloro-6-[(2-pyridinylimino)methyl]phenol, 2-{[(5-ethyl-2-hydroxyphenyl)imino]methyl}-4,6-diiodophenol, or a salt, polymorph, solvate, hydrate, or tautomer thereof.

13. The method according to claim 12, wherein the honeybee repellent is

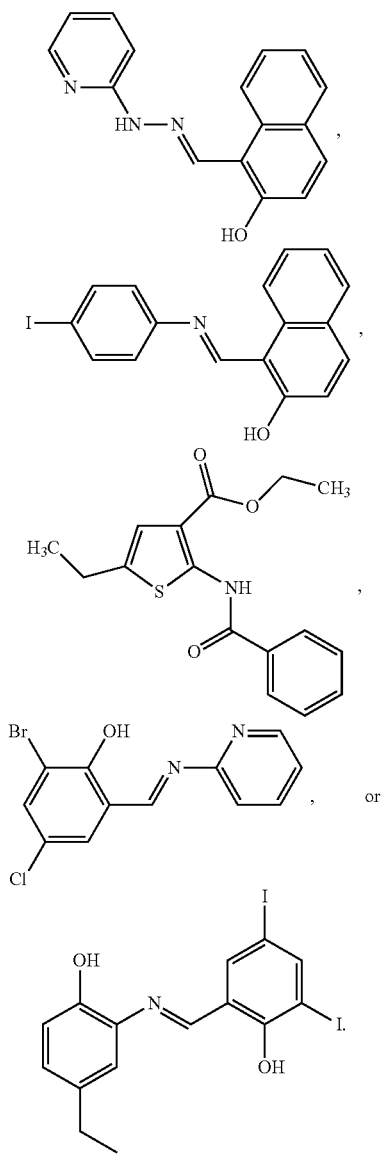

14. A seed composition comprising a seed and a honeybee repellent, the honeybee repellent comprising 2-hydroxy-1-naphthaldehyde 2-pyridinylhydrazone, 1-{[(4-iodophenyl)imino]methyl}-2-naphthol, ethyl 2-(benzoylamino)-5-ethyl-3-thiophenecarboxylate, 2-bromo-4-chloro-6-[(2-pyridinylimino)methyl]phenol, 2-{[(5-ethyl-2-hydroxyphenyl)imino]methyl}-4,6-diiodophenol, or a salt, polymorph, solvate, hydrate, or tautomer thereof.

15. The seed composition of claim 14, wherein the composition further comprises one or more of an insecticide, a pesticide, a fungicide, a fertilizer of a micronutrient or macronutrient nature, a herbicide, a feeding inhibitor, an insect molting inhibitor, an insect mating inhibitor, an insect maturation inhibitor, a nematocide, a nutritional or horticultural supplement, a larvicide, a seed, or any combination thereof.

16. The seed composition according to claim 15, wherein the insecticide is an organochlorine, an organophosphate, a carbamate, a pyrethroid, or a neonicotinoid.

17. The seed composition according to claim 16, wherein the neonicotinoid is Acetamiprid, Clothianidin, Imidacloprid, Nitenpyram, Nithiazine, Thiacloprid, or Thiamethoxam.

18. The seed composition according to claim 14, wherein the honeybee repellent is

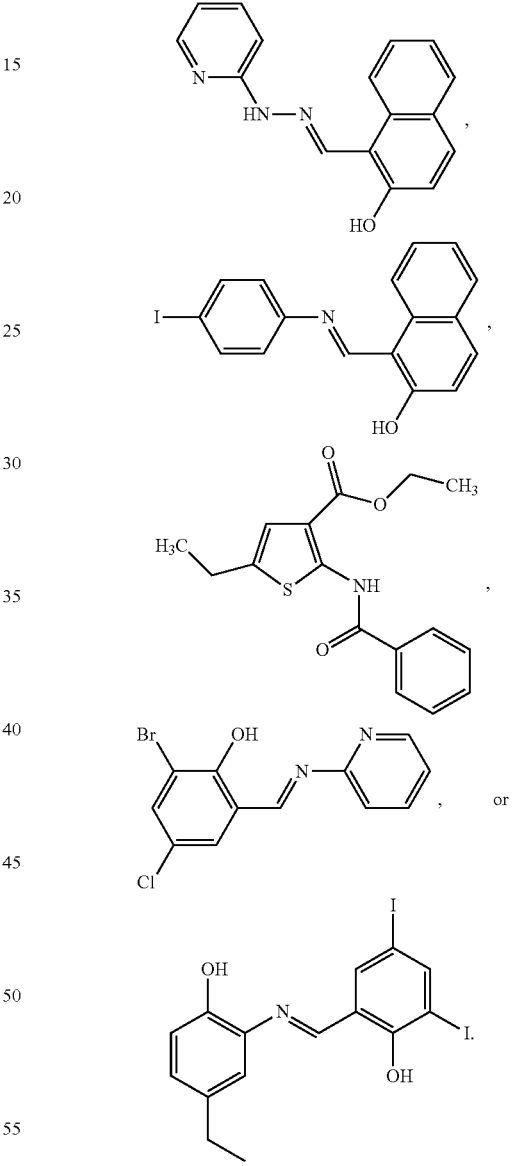

19. A housing or dispensing device comprising a composition as defined in claim 1.

* * * * *